United States Patent
Kwok

(10) Patent No.: US 7,217,864 B2
(45) Date of Patent: May 15, 2007

(54) SHADE RESPONSIVE PROMOTER, PROMOTER CONTROL ELEMENTS, AND COMBINATIONS, AND USES THEREOF

(75) Inventor: Shing Kwok, Woodland Hills, CA (US)

(73) Assignee: Ceres, Inc, Thousand Oaks, CA (US)

( * ) Notice: Subject to any disclaimer, the term of this patent is extended or adjusted under 35 U.S.C. 154(b) by 0 days.

(21) Appl. No.: 11/114,406

(22) Filed: Apr. 25, 2005

(65) Prior Publication Data

US 2005/0266559 A1    Dec. 1, 2005

Related U.S. Application Data

(60) Provisional application No. 60/564,658, filed on Apr. 23, 2004, provisional application No. 60/564,678, filed on Apr. 23, 2004.

(51) Int. Cl.
*A01H 5/00* (2006.01)
*C07H 21/04* (2006.01)
*C12N 5/04* (2006.01)
*C12N 15/09* (2006.01)

(52) U.S. Cl. .................. 800/295; 435/320.1; 435/419; 435/6; 435/69.1; 435/468; 536/24.1; 800/278

(58) Field of Classification Search .................... None
See application file for complete search history.

(56) References Cited

OTHER PUBLICATIONS

Kim et al. (Plant Molecular Biology, 24:105-117, 1994).*
Sato et al. (NCBI, GenBank, Sequence Accession No. AB009055, pp. 1-30, Published Aug. 9, 2000).*
Sato et al. (DNA Research 5:41-54, 1998).*
Valvekens et al. (PNAS, 85:5536-5540, 1988).*
Devlin et al. (Plant Physiol., 133:1617-1629, 2003).*
NCBI Database, AL021811, Arabidopsis thaliana, Jan. 2006.
NCBI Database, AL161580, Arabidopsis thaliana, Jan. 2006.

* cited by examiner

*Primary Examiner*—Phuong T Bui
*Assistant Examiner*—Vinod Kumar
(74) *Attorney, Agent, or Firm*—Birch Stewart Kolasch & Birch

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

20 Claims, 1 Drawing Sheet

Figure 1:
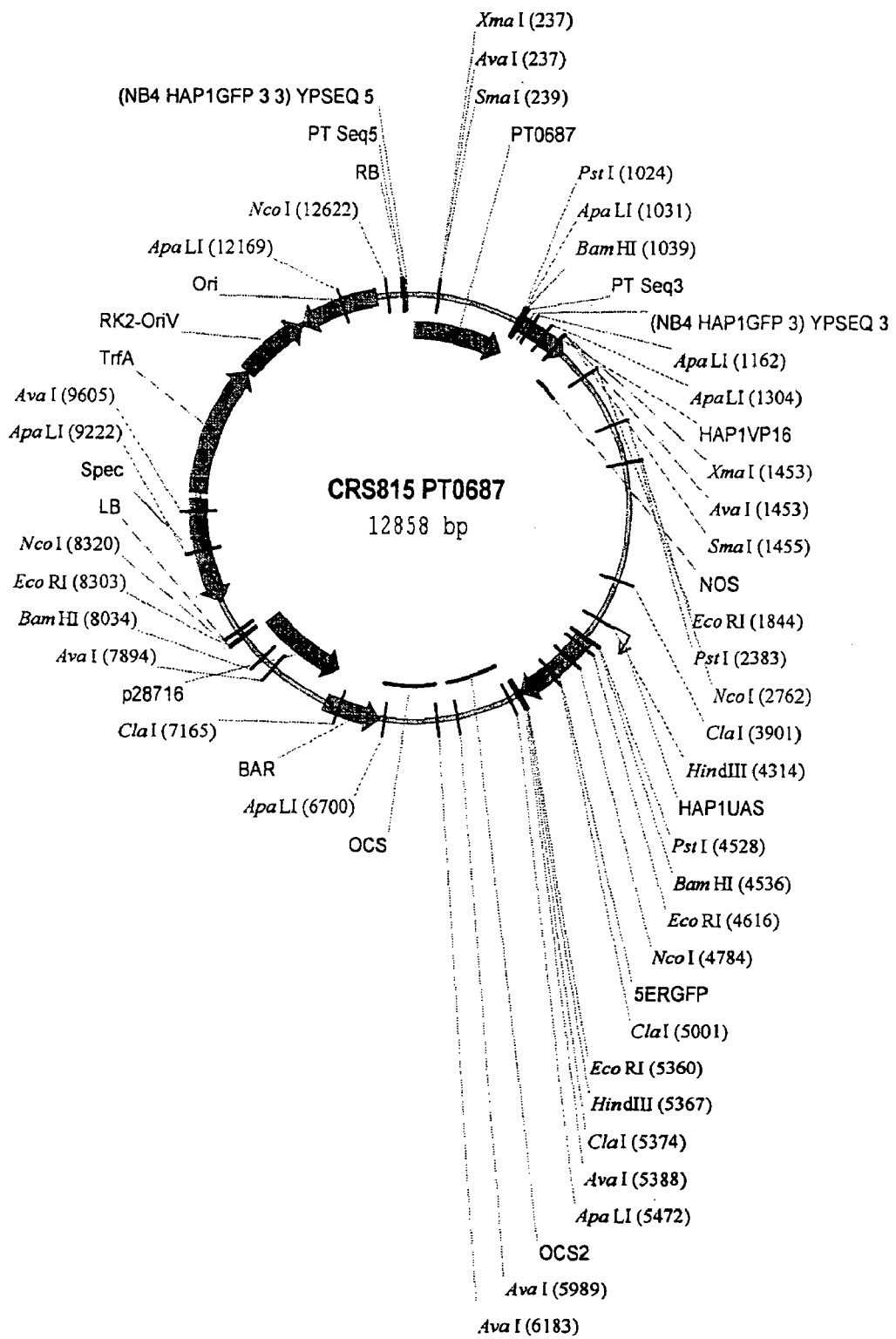

SEQUENCE LISTING

<160> NUMBER OF SEQ ID NOS: 30

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 1
tttttttttt tttttttv                                                    19

<210> SEQ ID NO 2
<211> LENGTH: 60
<212> TYPE: DNA
<213> ORGANISM: Arabidopsis thaliana
<220> FEATURE:

```
<221> NAME/KEY: misc_feature
<222> LOCATION: (24)..(37)
<223> OTHER INFORMATION: n is a, c, g, or t

<400> SEQUENCE: 2
ccagtcgatt ggcccgatcg gccnnnnnnn nnnnnnnggc ctgcagggcc agtgcactgg      60

<210> SEQ ID NO 3
<211> LENGTH: 1000
<212> TYPE: DNA
<213> ORGANISM: Arabidopsis thaliana

<400> SEQUENCE: 3
attattcaat ttaataaaaa ttgagtcggc caatttaatg cgagacttct gtacaacgac      60
cctaaaagtg ggtttgataa atgaaacata ttgcaacaaa aaaatactag taataatgat     120
aaaatagtaa catgtcgtgg cgcattgaat atcctacgaa ggtttagtgt ttacttttaa     180
aaaatcctaa tatgatacta gtacatatag ctagcttgcc ttgcttatgc tattgcatag     240
tctgtattaa taaatgatgt tatacatttc gatagagtaa cattttggga acatgagtga     300
acgtgcttga atcttcgtgc ccttgacgtc agaagctagt aattttaaat actaattaac     360
attcatacaa attaacagat acaatgtact atatcataat tcgtttccgt aacacaacgc     420
aacaatttga agtagatgt actttagtac ttagttagtg tgcaccaaaa aaaaaagatg     480
tagttagtta gtaaggggtt aaatgttta atttattaag aaaacttaaa ttcattaaat     540
gttagaaaaa gtctaattag tttatattcg aacactgtgc tcaaaattaa aaagtcaact     600
attttagact atagagttta ttaattaata ataaattcga taaatcaccg tattattttc     660
ttcaacgaca agtagccgtg aagacacggg agcgaagaga gataaacaga agatgaagaa     720
gaagatcaat gtcataatct tcagggagat aaatccgtaa tctttattaa tcaaggttaa     780
tccttttttt tttcttcatc ttaattcttt gcgtcttcct tttctattta tcacgagatc     840
tgtctttctt tttcctcttc tttctctctc ttctctctga agacagtact tgtttctgtc     900
cggcgttaaa agcttcggtg gtggtctctt gacttctctg agaagaagaa aaggaagctg     960
agtctcattt tagattcagc tcacgaggaa gtgacgacga                         1000

<210> SEQ ID NO 4
<211> LENGTH: 1098
<212> TYPE: DNA
<213> ORGANISM: Arabidopsis thaliana

<400> SEQUENCE: 4
tcgattggcc cgatcggcca ttattcaatt taataaaaat tgagtcggcc aatttaatgc      60
gagacttctg tacaacgacc ctaaaagtgg gtttgataaa tgaaacatat tgcaacaaaa     120
aaatactagt aataatgata aaatagtaac atgtcatggc gcattgaata tcctacgaag     180
gtttagtgtt tacttttaaa aaatcctaat atgatactag tacatatagc tagcttgcct     240
tgcttatgct attgcatagt ctgtattaat aaatgatgtt atacatttcg atagagtaac     300
attttgggaa catgagtgaa cgtgcttgaa tcttcgtgcc cttgacgtca gaagctagta     360
attttaaata ctaattaaca ttcatacaaa ttaacagata caatgtacta tatcataatt     420
cgtttccgta acacaacgca acaatttgaa gtagatgta ctttagtact tagttagtgt     480
gcaccaaaaa aaaagatgta gttagttagt aagggggttaa atgtttaat ttattaagaa     540 aacttaaatt cattaaatgt tagaaaagt ctaattagtt tatattcgaa cactgtgctc     600
aaaattaaaa agtcaactat tttagactat agagtttatt aattaataat aaattcgata     660
```

| | |
|---|---|
| aatcaccgta ttattttctt caacgacaag tagccgtgaa gacacgggag cgaagagaga | 720 |
| taaacagaag atgaagaaga agatcaatgt cataatcttc agggagataa atccgtaatc | 780 |
| tttattaatc aaggttaatc ctttttttt tcttcatctt aattctttgc gtcttccttt | 840 |
| tctatttatc acgagatctg tctttctttt tcctcttctt tctctctctt ctctctgaag | 900 |
| acagtacttg tttctgtccg gcgttaaaag cttcggtggt ggtctcttga cttctctgag | 960 |
| aagaagaaaa ggaagctgag tctcatttta gattcagctc acgaggaagt gacgacgagg | 1020 |
| cctgcagggc cagtgcactg ggatccaaca atgtcctccg actcgtccaa gatcaagagg | 1080 |
| aagcggaacc gcatcccg | 1098 |

<210> SEQ ID NO 5
<211> LENGTH: 1000
<212> TYPE: DNA
<213> ORGANISM: Arabidopsis thaliana

<400> SEQUENCE: 5

| | |
|---|---|
| cagccgtaaa tccttccata aatttatttt gcaagttttg ctcattatat aatgagcgga | 60 |
| atttatgata taatcgtttg taataatgtt atgttttgat caaaatttga aattaaaagt | 120 |
| aggtgagaac ttgttataca gtgtagataa ggtggatctt gaatataaaa ataaaattta | 180 |
| taagatgtat ttaaagcaga aaagcataaa actttagata aaataatgta aaaatgtgtt | 240 |
| agcatcaatg ttgggatatt ggccgacccg aacttaatca atgtcggaag ccattacttc | 300 |
| tctcccaaaa gacctttttc cttcggagaa ctaggaactt cctcactacc tttcgcttaa | 360 |
| cgtgaaagcc ataaatttca tatattcata aaaatcagaa aatctaaaac tgtttagtat | 420 |
| cacctgtttt tggtatagac tattggtttt gtgttacttc ctaaactata tgatttcgta | 480 |
| cttcattgga tcttatagag atgaatattc gtaaaaagat aagttatctg gtgaaacgtt | 540 |
| acttcagtca tgttgggtct agatttacat actactatga acatttttaa gataataatt | 600 |
| atcctagcca actatatgtt ctatattatg ggccaagaag atatagaact aaaagttcag | 660 |
| aatttaacga tataaattac tagtatattc taatacttga atgattactg ttttagttgt | 720 |
| ttagaataaa tagtagcgtg ttggttaaga taccatctat ccacatctat atttgtgtgg | 780 |
| gttacataaa atgtacataa tattatatac atatatatgt atattttga taaagccata | 840 |
| tattactcct tgacctctgc ccccatttcc ttttactata aataggaata ctcatgatcc | 900 |
| tctaattcag caatcaacac caacgaacac aacctttttcc aaagccaata ataaaagaac | 960 |
| aaaagctttt agtttcatca aagacgaagc tgccttagaa | 1000 |

<210> SEQ ID NO 6
<211> LENGTH: 999
<212> TYPE: DNA
<213> ORGANISM: Arabidopsis thaliana

<400> SEQUENCE: 6

| | |
|---|---|
| cagccgtaaa tcctccataa atttattttg caagttttgc tcattatata atgagcggaa | 60 |
| tttatgatat aatcgtttgt aataatgtta tgttttgatc aaaatttgaa attaaaagta | 120 |
| ggtgagaact tgttatacag tgtagataag gtggatcttg aatataaaaa taaaatttat | 180 |
| aagatgtatt taaagcagaa aagcataaaa ctttagataa aataatgtaa aaatgtgtta | 240 |
| gcatcaatgt tgggatattg gccgacccga acttaatcaa tgtcggaagc cattacttct | 300 |
| ctcccaaaag accttttttcc ttcggagaac taggaacttc tcactacct ttcgcttaac | 360 |

| | |
|---|---|
| gtgaaagcca taaatttcat atattcataa aaatcagaaa atctaaaact gtttagtatc | 420 |
| acctgttttt ggtatagact attggttttg tgttacttcc taaactatat gatttcgtac | 480 |
| ttcattggat cttatagaga tgaatattcg taaaaagata agttatctgg tgaaacgtta | 540 |
| cttcagtcat gttgggtcta gatttacata ctactatgaa acattttaag ataataatta | 600 |
| tcctagccaa ctatatgttc tatattatgg gccaagaaga tatagaacta aaagttcaga | 660 |
| atttaacgat ataaattact agtatattct aatacttgaa tgattactgt tttagttgtt | 720 |
| tagaataaat agtagcgtgt tggttaagat accatctatc cacatctata tttgtgtggg | 780 |
| ttacataaaa tgtacataat attatataca tatatatgta tattttttgat aaagccatat | 840 |
| attactcctt gacctctgcc cccatttcct tttactataa ataggaatac tcatgatcct | 900 |
| ctaattcagc aatcaacacc aacgaacaca acctttccca aagccaataa taaaagaaca | 960 |
| aaagcttta gtttcatcaa agacgaagct gccttagaa | 999 |

<210> SEQ ID NO 7
<211> LENGTH: 1000
<212> TYPE: DNA
<213> ORGANISM: Arabidopsis thaliana

<400> SEQUENCE: 7

| | |
|---|---|
| tgtttttcat tttttttca tttcgttact actaacagaa cttttcattt atatcttgaa | 60 |
| attttgttgt ataactcaaa taagattga aactaacatg atgatacttg taattatctg | 120 |
| attatttcct tccatgtaaa ccgatcaaca tctagtcgta aaacagaaaa caaaaaagac | 180 |
| actgatcgac actcatagca taacaaccga tcttagtata catatgtgtg atatgttacg | 240 |
| tcatatttag ctcatgcaaa ctagaatttc ttgccgtatt tcagttccat atatctcgga | 300 |
| tatgcatatc aaatttacga caagaatcta aattttgtga atatattacca aagattcctt | 360 |
| tatatataga aaagagataa attaaccaca caaacataat aaaatggaaa agaagaaga | 420 |
| gattcgaaaa tgtggaccca tttttttaaaa attctaacat tcaaactgaa taaatttccc | 480 |
| acgctaattt tgatttattt atctccttgc atatcggaat aagtataaca ttcttcaaag | 540 |
| accaaaaaaa gaagaaagta taatattctt tcaatcaatt tccatagaaa agatatggca | 600 |
| tttcaattac gtcccaaata tgacgatcga atcatctta tataactcaa agtatttaac | 660 |
| tacatatagt ttcgaatcag aaaaatagct ttggtttac ggattttgag ttatgctctt | 720 |
| gtgtcaaaat atgataaata aattgttggt agattgatag ataagattct tccttttcga | 780 |
| aaattctgga attctgcatt taatatatat atatatatca tataatataa tgataatcta | 840 |
| cttgtcagtc tacacacccc tttaccaaca tatatatata tatatagcac acactctaca | 900 |
| cggtttcctt atcctcatca aaattaacaa actcattttt gaatacccaa aaaaaaacct | 960 |
| agctagctcg aatttttta aatatataat aacatcaaca | 1000 |

<210> SEQ ID NO 8
<211> LENGTH: 1000
<212> TYPE: DNA
<213> ORGANISM: Arabidopsis thaliana

<400> SEQUENCE: 8

| | |
|---|---|
| tgtttttcat tttttttca tttcgttact actaacagaa cttttcattt atatcttgaa | 60 |
| attttgttgt ataactcaaa taagattga aactaacatg atgatacttg taattatctg | 120 |
| attatttcct tccatgtaaa ccgatcaaca tccagtcgta aaacagaaaa caaaaaagac | 180 |
| actgatcgac actcatagca taacaaccga tcttagtata catatgtgtg atatgttacg | 240 |

```
tcatatttag ctcatgcaaa ctagaatttc ttgccgtatt tcagttccat atatctcgga        300
tatgcatatc aaatttacga caagaatcta aattttgtga aatattacca aagattcctt        360
tatatataga aaagagataa attaaccaca caaacataat aaaatggaaa agaagaaga         420 gattcgaaaa tgtggaccca tttttaaaa attctaacat tcaaactgaa taaatttccc         480
acgctaattt tgatttattt atctccttgc atatcggaat aagtataaca ttcttcaaag        540
accaaaaaaa gaagaaagta taatattctt tcaatcaatt tccatagaaa agatatggca       600
tttcaattac gtcccaaata tgacgatcga aatcatctta taaactcaa agtatttaac       660 tacatatagt ttcgaatcag aaaaatagct ttggttttac ggattttgag ttatgctctt       720
gtgtcaaaat atgataaata aattgttggt agattgatag ataagattct tccttttcga      780
aaattctgga attctgcatt aatatatat atatatatca taatataa tgataatcta          840 cttgtcagtc tacacacccc tttaccaaca tatatatata tatatagcac acactctaca       900
cggtttcctt atcctcatca aaattaacaa actcatttt gaatacccaa aaaaaaacct        960
agctagctcg aatttttta aatatataat aacatcaaca                               1000

<210> SEQ ID NO 9
<211> LENGTH: 1000
<212> TYPE: DNA
<213> ORGANISM: Arabidopsis thaliana

<400> SEQUENCE: 9 gactttttt ttatggagaa caaattatcc agtagatgtt ttttttatt gctcagtaat         60 tgagaaatgg gcacgaggat gaagatattc cattgatgtg attccaatct taataacatt       120
gcaatttcgt agctatataa atcatttcat gtgtaatatt atccatcttg ttaaattttc       180
taatctctaa aatttcatac cgtttgtgtt taacatagtt tccgatccaa tccaatccag       240
caaagtgaaa taatttcgaa tgataaggct gttttgcaaa atgccaaata tggcggaaca       300 attttttattt aagaaacaag ataaggatta ttaatgatca gatatgcttg atgaagttgt      360
ggtccattct tacttctctt ctgcatattt atcacatcgg tttctcatta tctctatgca       420
ttcgggacta ctaatacaac aatagcacaa aaatacaacg tgacaacaaa acaaccgag        480 tagaaaacta taaagacaac aacatttcaa attctctgtt gccactaata ctgaaaatcc      540
atttaaattt tcttttttgtg ggttgaattt gcaccatata aaaatccaat aatacaaaag     600
aaagcaaata tacatgattg gatattcttc gattatgatg tcgaacaaca acaattatta     660
acatgtgtat agtttggcaa aaaatgaata tgaggtaaag agggctggac ccattggccc     720
tataagcatt aatgggcctg aaagcaacaa cagaaattgg aattaaataa cgttgggtat     780
ctgtctgtca catgcaacac agacaacttg agaatggatc aatcaacatt cacgtgccat     840
gatcctctct tcctcttatt ttgtctcctt ccaccaatcc catatctttc tctattatac    900
atctctaatt atctcacttt taacatatag ttttttata catctttaat gactatataa     960
accaaacact gatcttttc aggttgcgaa taaaccaaga                              1000

<210> SEQ ID NO 10
<211> LENGTH: 1000
<212> TYPE: DNA
<213> ORGANISM: Arabidopsis thaliana

<400> SEQUENCE: 10 gactttttt ttatggagaa caaattatcc agtagatgtt ttttttatt gctcagtaat         60
```

-continued

| | |
|---|---|
| tgagaaatgg gcacgaggat gaagatattc cattgatgtg attccaatct taataacatt | 120 |
| gcaatttcgt agctatataa atcatttcat gtgtaatatt atccatcttg ttaaattttc | 180 |
| taatctctaa aatttcatac cgtttgtgtt aacatagtt tccgatccaa tccaatccag | 240 |
| caaagtgaaa taatttcgaa tgataaggct gttttgcaaa atgccaaata tggcggaaca | 300 |
| attttattt aagaaacaag ataaggatta ttaatgatca gatatgcttg atgaagttgt | 360 |
| ggtccattct tacttctctt ctgcatattt atcacatcgg tttctcatta tctctatgca | 420 |
| ttcgggacta ctaatacaac aatagcacaa aaatacaacg tgacaacaaa acaaccgag | 480 |
| tagaaaacta taaagacaac aacatttcaa attctctgtt gccactaata ctgaaaatcc | 540 |
| atttaaattt tcttttttgtg ggttgaattt gcaccatata aaaatccaat aatacaaaag | 600 |
| aaagcaaata tacatgattg gatattcttc gattatgatg tcgaacaaca acaattatta | 660 |
| acatgtgtat agtttggcaa aaaatgaata tgaggtaaag agggctggac ccattggccc | 720 |
| tataagcatt aatgggcctg aaagcaacaa cagaaattgg aattaaataa cgttgggtat | 780 |
| ctgtctgtca catgcaacac agacaacttg agaatggatc aatcaacatt cacgtgccat | 840 |
| gatcctctct tcctcttatt ttgtctcctt ccaccaatcc catatctttc tctattatac | 900 |
| atctctaatt atctcacttt taacatatag ttttttttata catctttaat gactatataa | 960 |
| accaaacact gatctttttc aggttgcgaa taaaccaaga | 1000 |

<210> SEQ ID NO 11
<211> LENGTH: 1046
<212> TYPE: DNA
<213> ORGANISM: Arabidopsis thaliana

<400> SEQUENCE: 11

| | |
|---|---|
| ccagtcgatt ggcccgatcg gcctagctag atttctatat aaacagaaga aagttaaaaa | 60 |
| gcaaataaaa attcacaaat agaaatcgaa caaaaagcta tgaaaatata ataccataa | 120 |
| ccttatggaa aaacgatgaa atgcttaaca aaaaaaactt tggcaatggc atgcatgtgc | 180 |
| ctgtaacaga aggccccat aagctgttag tgatatacaa cttaagcaaa tgtgcactct | 240 |
| tcacgcactt cccgctttc taaatttcaa tttatttgtc tacattttg tccaaattat | 300 |
| tgatataatt ctaccacgac ttcccccaca tgtccctcca aagagatccg tactacacag | 360 |
| tctaccgaca gcacatgcat ggattttcca aaccatcttc tttaaggata tccttgaca | 420 |
| ttttaatat taaaaaaata acaaaaaatt caatatataa ataacatcct aaatctatgt | 480 |
| tttggtagaa aacaagttct aaagttcaca tttggacagt ggttagtact tggtaatcaa | 540 |
| aatatttgtt taagaatctt gactacttac ttagtctaaa ccctaacgta catggttaga | 600 |
| catattagac acaattctat tctatagctt cttaacaaac gtttagcata tccgaaatt | 660 |
| ggttttacca atatttatta ccgtacgtgt gttttttttct gtaagaaagg aaaaaaagcc | 720 |
| aactcatgat tcttctgata ttgcatgtaa tatatttgcc aaataagctt acgacacaaa | 780 |
| cacaatgaca ctatgacagt aagatatcat ttcaaaatac ggatatacccc ccaaattggt | 840 |
| ggcaatgaca agaaaaaaa gagttcttca cagtggcaca ttcgtaatac atatgaactt | 900 |
| tggtggttgt ttcgtaatat agatcgtact taaaacctct aaacaccgtt ctctttatt | 960 |
| gccatcttct tcattatcat catctccatc tctctctctc tctctctcat tttcttgaaa | 1020 |
| aagggcctgc agggccagtg cactgg | 1046 |

<210> SEQ ID NO 12
<211> LENGTH: 999

-continued

<212> TYPE: DNA
<213> ORGANISM: Arabidopsis thaliana

<400> SEQUENCE: 12

| tagctagatt | tctatataaa | cagaagaaag | ttaaaaagca | aataaaaatt | cacaaataga | 60 |
| aatcgaacaa | aaagctatga | aaatataaat | accataacct | tatggaaaaa | cgatgaaatg | 120 |
| cttaacaaaa | aaaactttgg | caatggcatg | catgtgcctg | taacagaagg | cccccataag | 180 |
| ctgttagtga | tatacaactt | aagcaaatgt | gcactcttca | cgcacttccc | gcttttctaa | 240 |
| atttcaattt | atttgtctac | attttttgtcc | aaattattga | taattcta | ccacgacttc | 300 |
| ccccacatgt | ccctccaaag | agatccgtac | tacacagtct | accgacagca | catgcatgga | 360 |
| ttttccaaac | catcttcttt | aaggataatc | cttgacattt | ttaatattaa | aaataacaa | 420 |
| aaaattcaat | atataaataa | catcctaaat | ctatgttttg | gtagaaaaca | agttctaaag | 480 |
| ttcacatttg | gacagtggtt | agtacttggt | aatcaaaata | tttgtttaag | aatcttgact | 540 |
| acttacttag | tctaaacccct | aacgtacatg | gttagacata | ttagacacaa | ttctattcta | 600 |
| tagcttctta | acaaacgttt | agcataatcc | gaaattggtt | ttaccaatat | ttattaccgt | 660 |
| acgtgtgttt | ttttctgtaa | gaaaggaaaa | aaagccaact | catgattctt | ctgatattgc | 720 |
| atgtaatata | tttgccaaat | aagcttacga | cacaaacaca | atgacactat | gacagtaaga | 780 |
| tatcatttca | aaatacggat | ataccccccaa | attggtggca | atgacaaaga | aaaaagagt | 840 |
| tcttcacagt | ggcacattcg | taatacatat | gaactttggt | ggttgtttcg | taatatagat | 900 |
| cgtacttaaa | acctctaaac | accgttctct | ttatttgcca | tcttcttcat | tatcatcatc | 960 |
| tccatctctc | tctctctctc | tctcattttc | ttgaaaaag | | | 999 |

<210> SEQ ID NO 13
<211> LENGTH: 1046
<212> TYPE: DNA
<213> ORGANISM: Arabidopsis thaliana

<400> SEQUENCE: 13

| ccagtcgatt | ggcccgatcg | gccaattaaa | tgaaactcgc | ccctaaatta | ggagggattt | 60 |
| gggtaagtgg | taacacattc | actggaaaca | tgtgaagaaa | ggaggatgtc | aagtagctga | 120 |
| aaactcagta | tagtaaccaa | cggcttctca | ccaacctttc | attaataatt | tggtcatccc | 180 |
| tatatttta | ttcaacattt | tgttttcaa | tagcttagag | caccttaata | cctttcagtg | 240 |
| tttttttata | aaaaaaaca | aaaattggga | ttaatcatca | atccccaaat | gtaacgttta | 300 |
| cttagattat | gttcattttt | ctatacacac | aaatcatatt | cttttgtttt | aatcttcgaa | 360 |
| aaacgagagg | acattaaata | cccctaaaaa | aggaggggac | attactacca | acgtacatta | 420 |
| acatgtttga | tagcaaacga | tttatttgt | tcgttttgaa | aaggggaaag | taatgtgtaa | 480 |
| attatgtaaa | gattaataaa | cttttatggt | atagtaacat | tttcgaataa | taagagaggg | 540 |
| aaaacactcg | ccattgtcgg | caatttagaa | ccaatattag | aagggtttt | ttagagaaaa | 600 |
| aggacttaaa | agtttagaga | ccttaacaac | aacttattta | gaaatagaca | tgcttaagtt | 660 |
| gacaacagcg | agtttatttt | ctatatcgaa | gaaaaatacg | aacttttct | taattagatt | 720 |
| tcgaatgcat | gcactatcga | gaatcgaccg | tcacaagaaa | aaactaatat | acatactgta | 780 |
| catatctata | ttcaatattg | gtggggatgg | gtttaatgtg | tatttataat | tcatggataa | 840 |
| attcacacaa | taaggtccat | gaaactagaa | ggtaccaaaa | ataagcatta | atgactcttt | 900 |
| gccacttata | tatatgattc | tctcatagta | ccatttatt | ctcccaaacc | tatcttcttc | 960 |

-continued

```
ttcctctctt gtctctctcg ctctctctct tctacattgt ttcttgaggt caatctatta    1020
aaaggccgat cgggccaatc gactgg                                         1046
```

<210> SEQ ID NO 14
<211> LENGTH: 998
<212> TYPE: DNA
<213> ORGANISM: Arabidopsis thaliana

<400> SEQUENCE: 14

```
aattaaatga aaccgcccct aaattaggag ggatttgggt aagtggtaac acattcactg      60
gaaacatgtg aagaaggag gatgtcaagt agctgaaaac tcagtatagt aaccaacggc     120
ttctcaccaa cctttcatta ataatttggt catccctata tttttattca acattttgtt    180
tttcaatagc ttagagcacc ttaataacctt tcagtgtttt tttataaaaa aaacaaaaat    240
tgggattaat catcaatccc caaatgtaac gtttacttag attatgttca tttttctata    300
cacacaaatc atattctttt gttttaatct tcgaaaaacg agaggacatt aaatacccct    360 aaaaaggag gggacattac taccaacgta cattaacatg tttgatagca acgatttat     420 tttgttcgtt ttgaaaaggg gaaagtaatg tgtaaattat gtaaagatta ataaactttt    480
atggtatagt aacattttcg aataataaga gagggaaaac actcgccatt gtcggcaatt    540
tagaaccaat attagaaggg tttttttaga gaaaaaggac ttaaaagttt agagaccta     600 acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg gataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                            998
```

<210> SEQ ID NO 15
<211> LENGTH: 604
<212> TYPE: DNA
<213> ORGANISM: Arabidopsis thaliana

<400> SEQUENCE: 15

```
acagatcaca ccaacataag gaacaaagcc aaaactatta atcatggttc aaaggcagtt     60
ggttaatcac ttttttcattt tcatgaaatg ttaaattaat taatcatcaa aagaggttat    120
ttaatttaca tagagtttag agcaatacca aaaaaaaaa aaaagaggtt ctaaaagaca    180
gttccaggaa caaataatt caaatttgtt aaattcctca tgttttacga cgtcatgtac    240
gtgtacgtca tgtacgtgac gaaagccatt tctgcaacaa accatttctc actttcatct    300
caaccatagg tatcgctttc ctctgcccctt gtgcatttca aacaatatca tttgctttat    360
ctctgcaatt atatatgtgt tggatataac caaaaaacct agacctacca cttcgctaag    420
gtaggtctgt ccgtgagttg tctgtgatta gatgttttta ttgttcaata ttgactcttc    480
tttcttttat ataatgaata atgtaaaaaa tttcctaata tttgtctacc ttataaatta    540
gaagcacaac actctctcct cttcacaaat ctcacatcct cactcctcag ctcctcaaat    600
caga                                                                 604
```

<210> SEQ ID NO 16
<211> LENGTH: 604

-continued

```
<212> TYPE: DNA
<213> ORGANISM: Arabidopsis thaliana

<400> SEQUENCE: 16
acagatcaca ccaacataag gaacaaagcc aaaactatta atcatggttc aaaggcagtt      60
ggttaatcac ttttcattt tcatgaaatg ttaaattaat taatcatcaa agaggttat      120
ttaatttaca tagagtttag agcaataccc aaaaaaaaaa aaaagaggtt ctaaaagaca    180
gttccaggaa caaataatt caatttgtt aaattcctca tgttttacga cgtcatgtac       240
gtgtacgtca tgtacgtgac gaaagccatt tctgcaacaa accatttctc actttcatct    300
caaccatagg tatcgctttc ctctgccctt gtgcatttca acaatatca tttgctttat     360
ctctgcaatt atatatgtgt tggatataac caaaaaacct agacctacca cttcgctaag   420
gtaggtctgt ccgtgagttg tctgtgatta gatgttttta ttgttcaata ttgactcttc    480
tttcttttat ataatgaata atgtaaaaaa tttcctaata tttgtctacc ttataaatta    540
gaagcacaac actctctcct cttcacaaat ctcacatcct caccctcag ctcctcaaat    600
caga                                                                  604

<210> SEQ ID NO 17
<211> LENGTH: 1046
<212> TYPE: DNA
<213> ORGANISM: Arabidopsis thaliana

<400> SEQUENCE: 17
ccagtcgatt ggcccgatcg gcctaagaaa aactgtaggc ttgttgtcag aacaaacatg      60
gacccatgtt ctctatgtcc ctaagatgtg taccaatctc aattcacttc ttttgttgca    120
ctatttttta aaaataact tttatttat attttgagat ctccattgcc cctgctgcac     180
tagacattac agctcatttt ttccttataa ttcaatccct agctattttt ctttcttatt     240
agtttaaact aatcatattt gggtaattag cgttgaaact atctatcata tcaattttaa    300
tgatacatat gcaatacttt atgtgagtat atgcatgtat gcatgttcca acatccagat     360
taatgactaa cgtttaagcc ctgatttttt cagagaaatt ttgtgttgta cctatgtttg    420
tattacacac aatatttacc attgtttaac atgtacacat gtgtttataa atctccgtac    480
actataatgc atatttgaac catatatgac agaaagttttt ccactagttc taattacatt   540
ttgttgccct ttcctactcg tctattgcct atagaaatat tatttagtt atgattaaga     600
attgggatgc acattccgaa attaattatt aaatgccact atgaagaacc cttgaacata    660
gtctaattca attttaagat cataaggaac attaacagtg acaatagcta aggtctctcg    720
acaatgagac aatccgcttt ttaaatatat acatataaga gataccatat tgtatacata    780
tgcagataca attcaacttt gaccaaattt attcaatttc tccttctctt tatatcaata   840
agaaactatt catgatactg gaccagcctg tttgaatctt gtcccatcca caaatctccc    900
aatatataaa taagaaccct tcacccgtaa aaccaaaacc atcaacaact tcaaagcttt    960
ctaagcaaga gattgagaga aatcggattt tctttctaag actcaaaata tctaaaaaca   1020
ataggcctgc agggccagtg cactgg                                         1046

<210> SEQ ID NO 18
<211> LENGTH: 1000
<212> TYPE: DNA
<213> ORGANISM: Arabidopsis thaliana

<400> SEQUENCE: 18
```

-continued

| | |
|---|---|
| taagaaaaac tgtaggcttg ttgtcagaac aaacatggac ccatgttctc tatgtcccta | 60 |
| agatgtgtac caatctcaat tcacttcttt tgttgcacta ttttttaaaa ataactttt | 120 |
| attttatatt ttgagatctc cattgcccct gctgcactag acattacagc tcatttttc | 180 |
| cttataattc aatccctagc tattttcttt tcttattagt ttaaactaat catatttggg | 240 |
| taattagcgt tgaaactatc tatcatatca attttaatga tacatatgca atactttatg | 300 |
| tgagtatatg catgtatgca tgttccaaca tccagattaa tgactaacgt ttaagccctg | 360 |
| attttttcag agaaattttg tgttgtacct atgtttgtat tacacacaat atttaccatt | 420 |
| gtttaacatg tacacatgtg tttataaatc tccgtacact ataatgcata tttgaaccat | 480 |
| atatgacaga aagttttcca ctagttctaa ttacattttg ttgccctttc ctactcgtct | 540 |
| attgcctata gaaatattat tttagttatg attaagaatt gggatgcaca ttccgaaatt | 600 |
| aattattaaa tgccactatg aagaaccctt gaacatagtc taattcaatt ttaagatcat | 660 |
| aaggaacatt aacagtgaca atagctaagg tctctcgaca atgagacaat ccgcttttta | 720 |
| aatatataca tataagagat accatattgt atacatatgc agatacaatt acaacttgac | 780 |
| caaatttatt caatttctcc ttctctttat atcaataaga aactattcat gatactggac | 840 |
| cagcctgttt gaatcttgtc ccatccacaa atctcccaat atataaataa agaaccttca | 900 |
| cccgtaaaac caaaccatc aacaacttca aagctttcta agcaagagat tgagagaaat | 960 |
| cggattttct ttctaagact caaaatatct aaaaacaata | 1000 |

<210> SEQ ID NO 19
<211> LENGTH: 1000
<212> TYPE: DNA
<213> ORGANISM: Arabidopsis thaliana

<400> SEQUENCE: 19

| | |
|---|---|
| ttgtttaaca cctcaaacct gttaagacta atcacaatgt tcgaagataa tgccatttct | 60 |
| atatatattt agtatagcat cacacatgcg ttctgtgttg caaagtttac tctagagtta | 120 |
| tcactgagtc atgactcatg atgaccatta ttatagtatt agtactttta agttttaggt | 180 |
| cgagaatatg aagctaatac atgcatgtaa tgatgtaaat atgcctacct taaaaaatat | 240 |
| cgaattattc agaaacaatg actcgatatc cgtaagaaac cgccagctcc tgctgaattg | 300 |
| catgaaccta tcttaatatt ctttcgccac gaactcttcc cttttgtctc cttcttataa | 360 |
| ctctacacat catcatttct tttccactaa ataacttaca atacgtatac cttttctttt | 420 |
| tttgtcaatt taaatcaaca ctaagatata ctttaaatac gaatcattta aatgaatata | 480 |
| atgtactaat tgtttcagat tttatttcct gtttaaaaat atactcatga actaaaacta | 540 |
| attaataaaa tgtggataaa ttaaagcctt ttaacaaaaa aaaatgtgg ataaattaat | 600 |
| atcaatatgt ttccttttta ttttattta tctatttcaa aaaataagt tattcaatac | 660 |
| atatgttgat attttgacta tttttaatca taatttaaat caattgttgt gttcttaagc | 720 |
| aaaatatcta aaaacgaata taaccacgtc caccatagaa gcactgcaat tttagcattc | 780 |
| taaaacatcc ttgatatttt tttgtcaacg tcttattatc ttttatctca aaccatgtat | 840 |
| atggatgtat ccactaacgc atatatag agacaattag gcatctatca ttttatccca | 900 |
| cacttatctc ttcctatctc tctctcattc aaacccaaat aggaaacaaa tacacaaaag | 960 |
| tataataaaa agtctttctc tcatctttcg ccacgtagac | 1000 |

<210> SEQ ID NO 20
<211> LENGTH: 1000

<212> TYPE: DNA
<213> ORGANISM: Arabidopsis thaliana

<400> SEQUENCE: 20

| | | | | | |
|---|---|---|---|---|---|
| ttgtttaaca | cctcaaacct | gttaagacta | atcacaatgt | tcgaagataa | tgccatttct | 60 |
| atatatattt | agtatagcat | cacacatgcg | ttctgtgttg | caaagtttac | tctagagtta | 120 |
| tcactgagtc | atgactcatg | atgaccatta | ttatagtatt | agtacttttta | agttttaggt | 180 |
| cgagaatgtg | aagctaatac | atgcatgtaa | tgatgtaaat | atgcctacct | aaaaaatat | 240 |
| cgaattattc | agaaacaatg | actcgatatc | cgtaagaaac | cgccagctcc | tgctgaattg | 300 |
| catgaaccta | tcttaatatt | ctttcgccac | gaactcttcc | cttttgtctc | cttcttataa | 360 |
| ctctacacat | catcatttct | tttccactaa | ataacttaca | atacgtatac | cttttttctt | 420 |
| tttgtcaatt | taaatcaaca | ctaagatata | ctttaaatac | gaatcattta | aatgaatata | 480 |
| atgtactaat | tgtttcagat | tttatttcct | gtttaaaaat | atactcatga | actaaaacta | 540 |
| attaataaaa | tgtggataaa | ttaaagcctt | ttaacaaaaa | aaaaatgtgg | ataaattaat | 600 |
| atcaatatgt | ttccttttta | tttttatttta | tctatttcaa | aaaaataagt | tattcaatac | 660 |
| atatgttgat | attttgacta | tttttaatca | taatttaaat | caattgttgt | gttcttaagc | 720 |
| aaaatatcta | aaaacgaata | taaccacgtc | caccatagaa | gcactgcaat | tttagcattc | 780 |
| taaaacatcc | ttgatatttt | tttgtcaacg | tcttattatc | ttttatctca | gaccatgtat | 840 |
| atggatgtat | ccactaacgc | atatatatag | agacaattag | gcatctatca | ttttatccca | 900 |
| cacttatctc | ttcctatctc | tctctcattc | aaacccaaat | aggaaacaaa | tacacaaaag | 960 |
| tataataaaa | agtctttctc | tcatctttcg | ccacgtagac | | | 1000 |

<210> SEQ ID NO 21
<211> LENGTH: 1000
<212> TYPE: DNA
<213> ORGANISM: Arabidopsis thaliana

<400> SEQUENCE: 21

| | | | | | |
|---|---|---|---|---|---|
| aagatagtac | agtttcagtg | ttttgagaaa | aaaagctgaa | ctaaaactaa | aatgtttaag | 60 |
| gacacaatat | ttagtttcaa | ttagataatt | caacagtttg | aacaatttt | tttttttttt | 120 |
| tttgaagtca | tttatttata | caatgtttta | aaacgcatta | agcatttagg | cagccgacaa | 180 |
| acgcctattg | tctaactgta | aataggcgct | tccacttagg | ttcatattgc | atatttacta | 240 |
| tatgtgtata | gtgacaaaaa | ccaatatttc | tcttattttg | gatgaaggta | tagtagttgt | 300 |
| taaatgttca | atataattaa | gcattaatga | caaataaaat | aaaattaatt | tagttgataa | 360 |
| aaagataatc | ttataaaaag | atcgatgaat | agatataatg | gtttactgaa | ttctatagct | 420 |
| cttaccttgc | acgactatgt | cccaaggaga | ggaagtacct | taactataat | tctgaacata | 480 |
| attttgtcta | tcttggtgag | tattatatga | cctaaaccct | ttaataagaa | aaagtataat | 540 |
| actggcgtaa | cgtaataaat | taacacaatc | ataagttgtt | gacaagcaaa | aaaacataca | 600 |
| taatttgttt | aatgagatat | attagttata | gttcttatgt | caaagtacaa | ttatgcctac | 660 |
| caaaattaat | taatgatttc | aacaggaagt | ctgagatgat | gggccgacgt | gtagttacgt | 720 |
| ttcttgaattt | gtgagagatg | gtatttatta | tactgaagaa | acattatttt | actaaataaa | 780 |
| ttttcatttc | acatcttctg | taatcaatgc | gggtagatga | agaagttgtt | aatacgatgg | 840 |
| ccaaccatat | ggatctcttt | tttggcgttt | ctatatatag | taacctcgac | tccaaaggca | 900 |
| ttacgtgact | caataaaatc | aagtcttttg | tttcctttta | tccaaaaaaa | aaaaaaagtc | 960 |

-continued

| | |
|---|---|
| ttgtgtttct cttaggttgg ttgagaatca tttcatttca | 1000 |

<210> SEQ ID NO 22
<211> LENGTH: 1000
<212> TYPE: DNA
<213> ORGANISM: Arabidopsis thaliana

<400> SEQUENCE: 22

| | |
|---|---|
| aagatagtac agtttcagtg ttttgagaaa aaaagctgaa ctaaaactaa aatgtttaag | 60 |
| gacacaatat ttagtttcaa ttagataatt caacagtttg aacaattttt tttttttttt | 120 |
| tttgaagtca tttatttata caatgtttta aaacgcatta agcatttagg cagccgacaa | 180 |
| acgcctattg tctaactgta aataggcgct tccacttagg ttcatattgc atatttacta | 240 |
| tatgtgtata gtgacaaaaa ccaatatttc tcttattttg gatgaaggta tagtagttgt | 300 |
| taaatgttca atataattaa gcattaatga caaataaaat aaaattaatt tagttgataa | 360 |
| aaagataatc ttataaaaag atcgatgaat agatataatg gtttactgaa ttctatagct | 420 |
| cttaccttgc acgactatgt cccaaggaga ggaagtacct taactataat tctgaacata | 480 |
| attttgtcta tcttggtgag tattatatga cctaaacccct ttaataagaa aaagtataat | 540 |
| actggcgtaa cgtaataaat taacacaatc ataagttgtt gacaagcaaa aaaacataca | 600 |
| taatttgttt aatgagatat attagttata gttcttatgt caaagtacaa ttatgcctac | 660 |
| caaaattaat taatgatttc aacaggaagt ctgagatgat gggccgacgt gtagttacgt | 720 |
| ttcttgaatt gtgagagatg gtatttatta tactgaagaa acattatttt actaaataaa | 780 |
| ttttcatttc acatcttctg taatcaatgc gggtagatga agaagttgtt aatacgatgg | 840 |
| ccaaccatat ggatctcttt tttggcgttt ctatatatag taacctcgac tccaaaggca | 900 |
| ttacgtgact caataaaatc aagtctttg tttccttta tccaaaaaaa aaaaaaagtc | 960 |
| ttgtgtttct cttaggttgg ttgagaatca tttcatttca | 1000 |

<210> SEQ ID NO 23
<211> LENGTH: 1000
<212> TYPE: DNA
<213> ORGANISM: Arabidopsis thaliana

<400> SEQUENCE: 23

| | |
|---|---|
| aaaatgttat ttgagacagc atatcacatg gccttaccat acttcctgca tccattattc | 60 |
| cattaagaac actcttcacc ctcatccaca tgcatctccc tccccaattt atttactatt | 120 |
| gatcataatt gtacaaacct atacttacaa tttatatatg tgtctacgag aaaataaata | 180 |
| atattttaca gtgttttgtc tattattttg ttctatagtt tcttgcaaac aaaacattac | 240 |
| ttttcacgca aaaactgtcg aaatatttat aaaaggaaat tgttaattct tcgatacaaa | 300 |
| ttgaccatta atatttgatc atctattcta gacatctact ctaccatata ccaaaccttt | 360 |
| acacaaaaat gaaatatttt catgaaaact accccacaac tggggtgatc gaaaaagctt | 420 |
| gatctatatg atcaacatgt ccaacactag tttcattttt tctactatga tatccgatga | 480 |
| tccaatctga actatacaaa atgtatctag atattttctt gaatcaatcc gaataacgaa | 540 |
| tagttgcaaa acataaacct agcgtgatcg tgtggtagaa ggacgaaggt cgagaagttc | 600 |
| tcttactctt atgattttct ctttactcat ttgaccgtaa gagaaagaaa cggctaggat | 660 |
| ctcgcgtacg caactggcgg agacaaatca ggaccgttga aaataagaaa gaagccgcgt | 720 |
| ccaaaatctt tgtgtcccac ctttgtcccc ttgcctctaa cttgcctcct catgctcccc | 780 |
| gacaacgtca taattcatat ctctctctct ctctcgttaa ccctaatttc aaagcatctt | 840 |

| | |
|---|---|
| tccttatata aatctctctc tctccctcac cattacacaa cacacacaag cattttcaag | 900 |
| gatatcaaat cacaatccca agaagagcaa taacaagaga agaagaagta gttcaagaat | 960 |
| taaggaagag agcttctccg ttaaagtata gtgagagaat | 1000 |

<210> SEQ ID NO 24
<211> LENGTH: 1000
<212> TYPE: DNA
<213> ORGANISM: Arabidopsis thaliana

<400> SEQUENCE: 24

| | |
|---|---|
| aaaatgttat ttgagacagc atatcacatg gccttaccat acttcctgca tccattattc | 60 |
| cattaagaac actcttcacc ctcatccaca tgcatctccc tccccaattt atttactatt | 120 |
| gatcataatt gtacaagcct atacttacaa tttatatatg tgtctacgag aaaataaata | 180 |
| atattttaca gtgttttgtc tattattttg ttctatagct tcttgcaaac aagacattac | 240 |
| ttttcacgca aaaactgtcg aaatatttat aaaaggaaat tgttaattct tcgatacaaa | 300 |
| ttgaccatta atatttgatc atctattcta gacatctact ctaccatata ccaaaccttt | 360 |
| acacaaaaat gaaatatttt catgaaaact accccacaac tggggtgatc gaaaaagctt | 420 |
| gatctatatg atcaacatgt ccaacactag tttcattttt tctactatga tatccgatga | 480 |
| tccaatctga actatacaaa atgtatctag atattttctt gaatcaatcc gaataacgaa | 540 |
| tagttgcaaa acataaacct agcgtgatcg tgtggtagaa ggacgaaggt cgagaagttc | 600 |
| tcttactctt atgatgttct ctttactcat ttgaccgtaa gagaaagaaa cggctaggat | 660 |
| ctcgcgtacg caactggcgg agacaaatca ggaccgttga aaataagaaa gaagccgcgt | 720 |
| ccaaaatctt tgtgtcccac cttgtcccc ttgcctctaa cttgcctcct catgctcccc | 780 |
| gacaacgtca taattcatat ctctctctct ctctcgttaa ccctaatttc aaagcatctt | 840 |
| tccttatata aatctctctc tctccctcac cattacacaa cacacacaag cattttcaag | 900 |
| gatatcaaat cacaatccca agaagagcaa taacaagaga agaagaagta gttcaagaat | 960 |
| taaggaagag agcttctccg ttaaagtata gtgagagaat | 1000 |

<210> SEQ ID NO 25
<211> LENGTH: 1000
<212> TYPE: DNA
<213> ORGANISM: Arabidopsis thaliana

<400> SEQUENCE: 25

| | |
|---|---|
| cactacacac gtgtgacctc atcctctccc acgtgaatat ccacgtggcg ttcttccgtt | 60 |
| ccgtttctcc catccctccc atgcctctcc ccatgactct atttatccca atcctctctt | 120 |
| cctttcatta atttatcagt taaaattcct ctttttttcct agtagtattt ggagttttca | 180 |
| tatcaaaaag tttagactaa ccctaaaaac attgatagaa aaacttatca ttttaaacgt | 240 |
| tcttggggac caatcaaaat ggttaattgt ctagtgcctg ttcttgattc ttcagacatg | 300 |
| gttgcaaaag tccatagtca aatcaaggtt atatgtagct tcaacactga taacacgttt | 360 |
| attaacaaaa ccatatcaaa atggttgttt tttgcatttt cagtcttgac gtatacactg | 420 |
| ccattttga attagtcaaa tcgttacgta gttggtctac gatgtctcgc tgaaacaaat | 480 |
| acatacgtgt gtatatacac tatgcaagta gtatagttaa catcataatt gaccctaagg | 540 |
| aaaaaagtta atgtaaacag tgacacgtag atatcacacg gttcttttttt ggttttgtt | 600 |
| aaagatgaac ttgttaataa agaatatgac gtgatcttct ccggtacaac tctttgtcct | 660 |

```
ataaatagag aactcttgtc ttcatattct cgacacacac atataaacgc acaaactcgt    720
taaatttgta cgaatataat ttttttttaaa acactcgtta taatatatta aagtttcacc    780
caaaccgaaa aaagagagaa tctgtgcatg ttgctcagaa atcttcaaa gcgtaatctg      840 ggcttacgtt agctctcacg aaccccccaag gatcttctat atatgttttt tcatttcccc    900
ataaaatctt tcattatcta aaaaatatta ttatcgtatc tttttttcttc tatatattct   960 tcctcctcaa tcttgattct tgtttcttga gtattctttg                         1000
```

<210> SEQ ID NO 26
<211> LENGTH: 998
<212> TYPE: DNA
<213> ORGANISM: Arabidopsis thaliana

<400> SEQUENCE: 26

```
cactaaacac gtgtgacctc atcctctccc acgtgaatat ccacgtggcg ttcttccgtt    60
ccgtttctcc catccctccc atgcctctcc ccatgactct atttatccca atcctctctt    120
cctttcatta atttatcagt taaaattcct ctttttttcct agtagtattt ggagttttca   180
tatcaaaaag tttagactaa ccctaaaaac attgatagaa aaacttatca ttttaaacgt    240
tcttggggac caatcaaaat ggttaattgt ctagtgcctg ttcttgattc ttcagacatg    300
gttgcaaaag tccatagtca aatcaaggtt atatgtagct tcaacactga taacacgttt    360
attaacaaac catatcaaaa tggttgtttt ttgcattttc agtcttgacg tatacactgc    420
catttttgaa ttagtcaaat cgttacgtag ttggtctacg atgtctcgct gaaacaaata    480
catacgtgtg tatatacact atgcaagtag tatagttaac atcataattg accctaagga   540 aaaagtttaat gtaaacagtg acacgtagat atcacacggt tcttttttgg ttttttgttaa  600 agatgaactt gttaataaag aatatgacgt gatcttctcc ggtacaactc tttgtcctat   660
aaatagagaa ctcttgtctt catattctcg acacacacat ataaacgcac aaactcgtta   720
aatttgtacg aatataattt tttttaaaac actcgttata atatattaaa gtttcaccca   780
aaccgaaaaa agagagaatc tgtgcatgtt gctcagaaaa tcttcaaagc gtaatctggg   840
cttacgttag ctctcacgaa ccccccaagga tcttctatat atgttttttc atttccccat   900
aaaatctttc attatctaaa aaatattatt atcgtatctt ttttcttcta tatattcttc   960
ctcctcaatc ttgattcttg tttcttgagt attctttg                          998
```

<210> SEQ ID NO 27
<211> LENGTH: 1000
<212> TYPE: DNA
<213> ORGANISM: Arabidopsis thaliana

<400> SEQUENCE: 27

```
gattgaatga tgagtgtgca cccttgtatt actaataaaa aatttagcaa cagttataag    60
ctaacgtcat ccatgagtca ttcattagat tcactatttg cgttctcaaa aatcgaattg   120
ttaaaatttg agaagctcta atatacgagt caatgagatg tggcaaaagc atgtccttga   180
ccataaaatt tcgaggggtc aactcattag ataaggacaa gaatcaacca attgaaggcg   240
tcttctataa caagtttctt tattactaat attaaagtcc aatggggtga gggggagaag   300
aacttaaata aaaggaaata attggtaagt gaataaaatc taaatacgat actagatgat   360
tgatttgtgc tagtgcatgg tattagatca gatatgtgtt actattcgaa ttcaaattgg   420
catattccat gttgttgata agaaaattgt agaagtgtaa aagctgagtt actatattca   480
aactagtggt ttacataaag tgagacaaca actgtttcac aaaaatgact ataaaatagt   540
```

-continued

| | |
|---|---|
| aagtagtatt aggtcaattg attttaaaat tttaatcaaa ttcaaatttg tgatataatc | 600 |
| aaatttgttt atagaaaatg ttaagaaatc aattttggca gaactaattc agtgagaaac | 660 |
| aatcatttac aaaaacaatt ttaacattat ttaacagtaa gatttgacat ttaacccgtt | 720 |
| cgtgtgaacc catcatatct aacatggctc tacccatgac gcctccatgc catggacaat | 780 |
| tttgacagat cagaagttct gaacgtggac gaggtaagaa caccatgatg atacgattgg | 840 |
| agttagttat gtcgccaccg acatcactgc caatctcatt aataaaagtg gtactaaatc | 900 |
| tctaatctct attaactata aatataacaa agaaccaaaa gaaagtttct tatctctctt | 960 |
| atctttcata atttccaaga aacacaaacc ttttctacta | 1000 |

<210> SEQ ID NO 28
<211> LENGTH: 1000
<212> TYPE: DNA
<213> ORGANISM: Arabidopsis thaliana

<400> SEQUENCE: 28

| | |
|---|---|
| gattgaatga tgagtgtgca cccttgtatt actaataaaa aatttagcaa cagttataag | 60 |
| ctaacgtcat ccatgagtca ttcattagat tcactatttg cgttctcaaa aatcgaattg | 120 |
| ttaaaatttg agaagctcta atatacgagt caatgagatg tggcaaaagc atgtccttga | 180 |
| ccataaaatt tcgagggggtc aactcattag ataaggacaa gaatcaacca attgaaggcg | 240 |
| tcttctataa caagtttctt tattactaat attaaagtcc aatggggtga gggggagaag | 300 |
| aacttaaata aaaggaaata attggtaagt gaataaaatc taaatacgat actagatgat | 360 |
| tgatttgtgc tagtgcatgg tattagatca gatatgtgtt actattcgaa ttcaaattgg | 420 |
| catattccat gttgttgata agaaaattgt agaagtgtaa aagctgagtt actatattca | 480 |
| aactagtggt ttacataaag tgagacaaca actgtttcac aaaaatgact ataaaatagt | 540 |
| aagtagtatt aggtcaattg attttaaaat tttaatcaaa ttcaaatttg tgatataatc | 600 |
| aaatttgttt atagaaaatg ttaagaaatc aattttggca gaactaattc agtgagaaac | 660 |
| aatcatttac aaaaacaatt ttaacattat ttaacagtaa gatttgacat ttaacccgtt | 720 |
| cgtgtgaacc catcatatct aacatggctc tacccatgac gcctccatgc catggacaat | 780 |
| tttgacagat cagaagttct gaacgtggac gaggtaagaa caccatgatg atacgattgg | 840 |
| agttagttat gtcgccaccg acatcactgc caatctcatt aataaaagtg gtactaaatc | 900 |
| tctaatctct attaactata aatataacaa agaaccaaaa gaaagtttct tatctctctt | 960 |
| atctttcata atttccaaga aacacaaacc ttttctacta | 1000 |

<210> SEQ ID NO 29
<211> LENGTH: 1046
<212> TYPE: DNA
<213> ORGANISM: Arabidopsis thaliana

<400> SEQUENCE: 29

| | |
|---|---|
| ccagtcgatt ggcccgatcg gcccaacaaa cattcccttg gagatttgag agattcatat | 60 |
| cattaaatgc acttctcaat atacggagta ttactaatta aaaccttatt tcgagttctc | 120 |
| tcaaacgtaa cccatgcaaa aatggcccca gagataagac tttgatgagt ctccacgtca | 180 |
| ctttctgatt tcggcttttg tcccctaatc tttcgacaac attcgtctcg caccccgaca | 240 |
| tttcccggga cctctgtctc tcccctctc tttctcctct cctctcccat ttctcaactt | 300 |
| ttttccttat tcacgaaata gactttttttt attttagttt tcttttctcc catttgtaac | 360 |

```
                                                        -continued
tcgtggtcct tcttcatttg tattaatgct ctggaaattt tcttcttaaa acgttataca         420
gctatttttg cttttcccta tacatattcg tttcatagtt gtgttttctt tgtctatcaa         480
aacaattagt tccatgagat atgtgtcaat acttaacatg catcgtcttt ttctgatttg         540
tggataactc tctaaacaaa ttaaaataat catgctctag gagaggagat aacgtcattc         600
atatcatgat cttcctaatt aaaatataat tatgttgcca ccgggaatat aattaaaata         660
accctatatt cgaaaagaaa agagaaaaca aaaactaaaa aaaaaaagga aaggagtgaa         720
ggcaacagca cataatgaga ggttagtatg ggctcacaaa ctcttatgtt tcttttcttt         780
tcttttttcc ctttccaatt attaatatct attgtttctt accaaactaa ccacatatat         840
atttatatat taccgttatt aaattaaaat aaaattatgt gtatatgtcc ctctctatat         900
ataaacactg aaacatatgt tcccaattca aaaaattgtt ttgtctcaaa caaatttctc         960
tgcacacact caacaacata tcccataaca aaaaaagct attaaaaaaa aagagaagca        1020
gccggcctgc agggccagtg cactgg                                             1046

<210> SEQ ID NO 30
<211> LENGTH: 1000
<212> TYPE: DNA
<213> ORGANISM: Arabidopsis thaliana

<400> SEQUENCE: 30
caacaaacat tcccttggag atttgagaga ttcatatcat taaatgcact tctcaatata          60
cggagtatta ctaattaaaa ccttatttcg agttctctca aacgtaaccc atgcaaaaat         120
ggccccagag ataagacttt gatgagtctc cacgtcactt tctgatttcg gcttttgtcc         180
cctaatcttt cgacaacatt cgtctcgcac cccgacattt cccgggacct ctgtctctcc         240
ccctctcttt ctcctctcct ctcccatttc tcaacttttt tccttattca cgaaatagac         300
tttttttatt ttagttttct tttctcccat ttgtaactcg tggtccttct tcatttgtat         360
taatgctctg gaaattttct tcttaaaacg ttatacagct attttgctt tttcctatac         420 atattcgttt catagttgtg ttttctttgt ctatcaaaac aattagttcc atgagatatg         480
tgtcaatact taacatgcat cgtctttttc tgatttgtgg ataactctct aaacaaatta         540
aaataatcat gctctaggag aggagataac gtcattcata tcatgatctt cctaattaaa         600
atataattat gttgccaccg ggaatataat taaaataacc ctatattcga aagaaaaga         660 gaaaacaaaa actaaaaaaa aaaggaaag gagtgaaggc aacagcacat aatgagaggt         720
tagtatgggc tcacaaactc ttatgtttct tttcttttct tttttccctt tccaattatt         780
aatatctatt gtttcttacc aaactaacca catatatatt tatatattac cgttattaaa         840
ttaaaataaa attatgtgta tatgtccctc tctatatata aacactgaaa catatgttcc         900
caattcaaaa aattgttttg tctcaaacaa atttctctgc acacactcaa caacatatcc         960
cataacaaaa aaagctatt aaaaaaaaag agaagcagcc                              1000
```

SHADE RESPONSIVE PROMOTER, PROMOTER CONTROL ELEMENTS, AND COMBINATIONS, AND USES THEREOF

This Nonprovisional application claims priority under 35 U.S.C. § 119(e) on U.S. Provisional Application No(s). 60/564,658 and 60/564,678 both filed on Apr. 23, 2004, the entire contents of which are hereby incorporated by reference.

FIELD OF THE INVENTION

The present invention relates to shade responsive promoters and promoter control elements that are useful for modulating transcription of a desired polynucleotide. Such shade responsive promoters and promoter control elements can be included in polynucleotide constructs, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the shade responsive promoters and promoter control elements of the present invention are also a part of the invention.

BACKGROUND OF THE INVENTION

As every gardener knows, when plants are too close together the crowding elicits a number of developmental responses, such as stem and petiole elongation, branch suppression and accelerated flowering (Smith, H. 1982, *Light quality, photoreception and plant strategy*. Annu. Rev. Pl. Physiol. 33: 481–518 and Schmitt, J. and R., D., Wulff 1993, *Light spectral quality, phytochrome and plant competition*. Trends Ecol. Evol. 8:47–50). This shade avoidance response is triggered by the reduced ratio of red to far red wavelengths (R:FR) transmitted through or reflected from green vegetation due to selective absorption of visible wavelengths by chlorophyll (see Smith 1982, above).

It is the phytochrome family of photoreceptors that senses these environmental variations in the R:FR ratio. Phytochromes reversibly switch between R and FR-absorbing forms and interacts with multiple signaling pathways, such as the auxin pathway, to provide a dynamic response to shade (see Smith 1982 and Smith, H. 1995, *Physiological and ecological function within the phytochrome family*. Annu. Rev. Plant Physiol. Plant Mol. Biol. 46:289–315).

Shade tolerance, or the ability to tolerate extended periods of low light, varies from species to species. Photosynthesis is decreased in shade. As a consequence, in species such as turf grasses this results in decreased carbohydrate reserves and reduced root, rhizome and tiller growth. In the turf grass industry this is problematic because about 20–25% of turf grasses are grown under low light conditions and a considerable amount of time and money is spent by golf courses in an effort to maintain quality turf under shade conditions.

Shade intolerance (shade avoidance) is detrimental to crop plants because the growth and performance of crop plants depends largely on crop architecture, and plant architecture is affected by reduced light. That is, densely planted crops that shade one another tend to place energy into stem and petiole elongation to lift the leaves into the sunlight rather than putting energy into storage or reproductive structures. This negatively affects yields by reducing the amount of harvestable products such as seeds, fruits and tubers. In addition, tall spindly plants tend to be less wind resistant and fall over easily, further reducing crop yield.

Likewise, shade intolerance negatively affects forestry plantings. Here, seedlings of shade tolerate species will self-prune at a slower rate and survive for longer periods under a dense forest canopy than shade intolerant trees. Since most commercially important tree species are shade intolerant to only moderately tolerant of shade, tree plantings must be less dense and require increased acreage.

In the field of agriculture efforts are constantly being made to produce plants with an increased growth potential in order to feed the ever-increasing world population. A similar effort is underway in the field of forestry with the goal of guaranteeing a supply of reproducible raw materials. Conventionally, plant improvement has been achieved via plant breeding. The breeding process is, however, both time-consuming and labor-intensive, especially in forestry where trees may not reach reproductive maturity for decades. Furthermore, appropriate breeding programs must be performed for each relevant plant species.

The genetic manipulation of plants has expedited progress by introducing and expressing specific recombinant nucleic acid molecules. This approach has the advantage of being generally transferable among plant species rather than being limited to one plant species. For example, EP-A 0 511 979 describes the expression of a prokaryotic asparagine synthetase gene in plant cells that leads to increased biomass production. Likewise, WO 96/21737 describes plants with increased yield (growth potential) arising from an increase in the photosynthesis rate and the expression of deregulated or unregulated fructose-1,6-bisphosphatase. Nevertheless, there still is a need for generally applicable processes that improve agricultural and forest plant growth potential. Therefore, the present invention relates to a process for increasing the growth potential in plants, characterized by expression of recombinant DNA molecules stably integrated into the plant genome, particularly in combination with the shade responsive promoters of the invention.

SUMMARY OF THE INVENTION

The present invention is directed to isolated polynucleotide sequences that comprise shade responsive promoters and promoter control elements from plants, especially *Arabidopsis thaliana*, *Glycine max*, *Oryza sativa*, and *Zea mays*, and other shade responsive promoters and promoter control elements functional in plants.

Plants grown under dense canopies or at high density perceive a decrease in the ratio of red to far-red incoming light, and respond to it by growing faster and taller (Cerdan and Chory, 2003). This can make them feeble in stature and result in seed abortion. Therefore, a further understanding will be important in the appropriate manipulation of a plant's response to shade. One objective of the present invention is to express genes that may attenuate the shade avoidance response when plants sense shaded conditions. To this end, identification of shade induced promoters is extremely valuable.

It is one object of the present invention to provide isolated polynucleotides that are shade responsive promoter sequences. These shade responsive promoter sequences comprise, for example, (1) a polynucleotide having a nucleotide sequence as set forth in the section entitled "The promoter sequence", and according to SEQ ID NOS. 3–30, or a fragment thereof;

(2) a polynucleotide having a nucleotide sequence having at least 80% sequence identity to a sequence as set forth in Table 1, in the section entitled "The promoter sequence" or fragment thereof; and (3) a polynucleotide having a nucleotide sequence which hybridizes to a sequence as set forth in Table 1, in the section entitled "The promoter sequence" under a condition establishing a Tm −20° C.

Shade responsive promoter or promoter control element sequences of the present invention are capable of modulating preferential transcription, particularly in response to shade conditions.

In another embodiment, the present shade responsive promoter control elements are capable of serving as or fulfilling the function, for example, as a core shade responsive promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above, and the second promoter control element is heterologous to the first control element. Moreover, the first and second control elements are operably linked. Such shade responsive promoters may modulate transcript levels preferentially in a tissue or under particular conditions.

In another embodiment, the present isolated polynucleotide comprises a shade responsive promoter or a promoter control element as described above, wherein the shade responsive promoter or promoter control element is operably linked to a polynucleotide to be transcribed.

In another embodiment of the present vector, the shade responsive promoter and promoter control elements of the instant invention are operably linked to a heterologous polynucleotide that is a regulatory sequence.

It is another object of the present invention to provide a host cell comprising an isolated polynucleotide or vector as described above or fragment thereof. Host cells include, for instance, bacterial, yeast, insect, mammalian, and plant. The host cell can comprise a shade responsive promoter or promoter control element exogenous to the genome. Such a shade responsive promoter can modulate transcription in cis- and in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or host cell. This method comprises providing a polynucleotide or vector according to the present invention as described above, and contacting the sample of the polynucleotide or vector with conditions that permit transcription.

In another embodiment of the present method, the polynucleotide or vector preferentially modulates:

(a) constitutive transcription,
(b) stress induced transcription,
(c) light induced transcription,
(d) dark induced transcription,
(e) leaf transcription,
(f) root transcription,
(g) stem or shoot transcription,
(h) silique transcription,
(i) callus transcription,
(j) flower transcription,
(k) immature bud and inflorescence specific transcription, or
(l) senescing induced transcription
(m) germination transcription.

Other and further objects of the present invention will be made clear or become apparent from the following description.

BRIEF DESCRIPTION OF THE TABLES AND FIGURES

FIG. 1 is a schematic representation of the vector pNew-Bin4-HAP1-GFP.

The definitions of the abbreviations used in the vector map are as follows:

Ori—the origin of replication used by an *E. coli* host

RB—sequence for the right border of the T-DNA from pMOG800

BstXI—restriction enzyme cleavage site used for cloning

HAP1VP16 coding sequence for a fusion protein of the HAP1 and VP16 activation domains NOS—terminator region from the nopaline synthase gene HAP1UAS—the upstream activating sequence for HAP1

5ERGFP—the green fluorescent protein gene that has been optimized for localization to the endoplasmic reticulum OCS2—the terminator sequence from the octopine synthase 2 gene OCS—the terminator sequence from the octopine synthase gene p28716 (a.k.a 28716 short) promoter used to drive expression of the PAT (BAR) gene PAT (BAR)—a marker gene conferring herbicide resistance LB—sequence for the left border of the T-DNA from pMOG800

Spec—a marker gene conferring spectinomycin resistance

TrfA—transcription repression factor gene

RK2-OriV—origin of replication for Agrobacterium

Tables 1 and 2 consist of the Expression Reports for each shade responsive promoter of the invention providing the nucleotide sequence for each shade responsive promoter and details for expression driven by each of the nucleic acid shade responsive promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter, and the vector and marker genes used for the construct. The following symbols are used consistently throughout the Table:

T1: First generation transformant
T2: Second generation transformant
T3: Third generation transformant
(L): low expression level
(M): medium expression level
(H): high expression level Each row of the table begins with a heading identifying the data to be found in the section. The following provides a description of the data to be found in each section:

Description of Table 1

| Heading in Table 1 | Description |
| --- | --- |
| Promoter Candidate ID | Identifies the particular promoter by its construct ID, including the name of the plant origin. |
| Modulates the gene as identified by: | This row states the name of the gene modulated by the promoter |
| The GenBank description of the gene: | This field gives the Locus Number of the gene as well as the accession number. |
| The promoter sequence: | Provides the nucleic acid promoter sequence. |
| The promoter was cloned from the organism: | Identifies the source of the DNA template used to clone the promoter. |
| Alternative nucleotides: | Identifies alternative nucleotides in the promoter sequence at the base pair positions identified in the column called "Sequence (bp)" based upon nucleotide difference between the two species of *Arabidopsis*. |
| The promoter was cloned in the vector: | Identifies the vector used into which a promoter was cloned. |
| When cloned into the vector the promoter was operably linked to a marker, which was the type: | Identifies the type of marker linked to the promoter. The marker is used to determine patterns of gene expression in plant tissue. |
| Promoter-marker vector was tested in: | Identifies the organism in which the promoter-marker vector was tested. |
| Generation screened: ☐T1 Mature ☐T2 Seedling ☐T2 Mature ☐T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| The spatial expression of the promoter-marker vector was found observed in and would be useful in expression in any or all of the following: | Identifies the specific parts of the plant where various levels of GFP expression are observed. Expression levels are noted as either low (L), medium (M), or high (H). |
| Observed expression pattern of the promoter-marker vector was in:<br>T1 mature:<br>T2 seedling: | Identifies a general explanation of where GFP expression in different generations of plants was observed. |
| The promoter can be of use in the following trait and sub-trait areas: | Identifies which traits and subtraits the promoter cDNA can modulate |
| The promoter has utility in: | Identifies a specific function or functions that can be modulated using the promoter cDNA. |
| Misc. promoter information:<br>Bidirectionality:<br>Exons:<br>Repeats: | "Bidirectionality" is determined by the number of base pairs between the promoter and the start codon of a neighboring gene. A promoter is considered bidirectional if it is closer than 200 bp to a start codon of a gene 5' or 3' to the promoter. "Exons" (or any coding sequence) identifies if the promoter has overlapped with either the modulating gene's or other neighboring gene's coding sequence. A "fail" for exons means that this overlap has occurred. "Repeats" identifies the presence of normally occurring sequence repeats that randomly exist throughout the genome. A "pass" for repeats indicates a lack of repeats in the promoter. |
| Optional Promoter Fragments: An overlap with the__UTR/exon region of the endogenous coding sequence to the promoter occurs at base pairs__. | Identifies the specific nucleotides overlapping the UTR region or exon of a neighboring gene. The orientation relative to the promoter is designated with a 5' or 3'. |
| The Ceres cDNA ID of the endogenous coding sequence to the promoter: | Identifies the number associated with the Ceres cDNA that corresponds to the endogenous cDNA sequence of the promoter. |
| cDNA nucleotide sequence: | The nucleic acid sequence of the Ceres cDNA matching the endogenous cDNA region of the promoter. |
| Coding sequence: | A translated protein sequence of the gene modulated by a protein encoded by a cDNA |

Description of Table 2

| Heading in Table 2 | Description |
| --- | --- |
| Promoter Express Report # | Provides an internal report code |
| Pomoter Tested in | Identified the plant species into which the promoter was cloved and tested. |
| Spatial expression summary: | Summarizes the identity of the specific parts of the plant where various levels of GFP expression was observed. Expression levels are noted as either Low (L), medium (M) or high (H). |
| Observed Expression pattern: | Provides a general explanation of where GFP expression was observed in different plant generations. |
| Expected expression patterns: | Identifies tissues where expressions might be expected. |
| Selection criteria: | Criteria for selecting plants to be observed. |
| Gene: | Provides information on the closest gene match found in the Gen Ban and Pfam data bases. |
| Gen Bank: | Provides information on the closest gene match found in the Gen Ban and Pfam data bases. |
| Source Promoter Organism | Identifies the plant source for the cloned promoter. |
| Vector | Identifies the section into which the promoter was cloned. |
| Marker type | The type of marker sequence used. |
| Generation screened | Identifies the plant generation(s) used in the screening process. T1 plants are those plants subjected to the transformation event while the T2 generation plants are from the seeds collected from the T1 plants and T3 plants are from the seeds of T2 plants. |
| Inductors completed: | Describes the types of test and general parameters used for screening of the promoter. |
| $T_1$ Matures Plant Expression | Reports the observed results of expression in parts of the plant into L, M, or H being positioned prior to the name of the observed tissue. |
| Promoter Utility: | This section describes a function or functions that can be modulated using the promoter. |
| Construct: | This section provides identification numbers for the promoter and tests. |
| (A) Predicted promoter sequence: | Provides the sequence information for the promoter prior to insertion into a plant |
| (B) Sequence verification and confirmation: | Describes the seqeucne of the promoter as determined after insertion into a transferred plant. |
| (C) Predicted vs. Experimental sequence experiment | Provides an alignment for each of the predicted and verified promoter sequences. |

The section of Table 1 entitled "optional promoter fragments" identifies the co-ordinates of nucleotides of the promoter that represent optional promoter fragments. The optional promoter fragments comprise the 5' UTR and any exon(s) of the endogenous coding region. The optional promoter fragments may also comprise any exon(s) and the 3' or 5' UTR of the gene residing upstream of the promoter (that is, 5' to the promoter). The optional promoter fragments also include any intervening sequences that are introns or sequence occurring between exons or an exon and the UTR.

The information on optional promoter fragments can be used to generate either reduced promoter sequences or "core" promoters. A reduced promoter sequence is generated when at least one optional promoter fragment is deleted. Deletion of all optional promoter fragments generates a "core" promoter.

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct, such as the promoter and the polynucleotide to be transcribed and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Core Promoter: This is the minimal stretch of contiguous DNA sequence that is sufficient to direct accurate initiation of transcription by the RNA polymerase II machinery (for review see: Struhl, 1987, *Cell* 49: 295–297; Smale, 1994, In *Transcription: Mechanisms and Regulation* (eds R. C. Conaway and J. W. Conaway), pp 63–81/Raven Press, Ltd., New York; Smale, 1997, *Biochem. Biophys. Acta* 1351:73–88; Smale et al., 1998, *Cold Spring Harb. Symp. Quant. Biol.* 58: 21–31; Smale, 2001, *Genes & Dev.* 15: 2503–2508; Weis and Reinberg, 1992, *FASEB J.* 6: 3300–3309; Burke et al., 1998, *Cold Spring Harb. Symp. Quant. Biol* 63: 75–82). There are several sequence motifs, including the TATA box, initiator (Inr), TFIIB recognition element (BRE) and downstream core promoter element (DPE), that are commonly found in core promoters, however not all of these elements occur in all promoters and there are no universal core promoter elements (Butler and Kadonaga, 2002, Genes & Dev. 16: 2583–2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organisms regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or orgasm regenerated from said host cell by any means other than by a sexual cross. Examples of means by which this can be accomplished are described below, and include Agrobacterium-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function (see SCHEMATIC 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an Arabidopsis coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an Arabidopsis gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound or the presence of light.

Modulate Transcription Level: As used herein, the phrase "modulate transcription" describes the biological activity of a promoter sequence or promoter control element. Such modulation includes, without limitation, includes up- and down-regulation of initiation of transcription, rate of transcription, and/or transcription levels.

Mutant: In the current invention, "mutant" refers to a heritable change in nucleotide sequence at a specific location. Mutant genes of the current invention may or may not have an associated identifiable phenotype.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible at the National Center for Biotechnology Information (NCBI) website). The database at the NCBI FTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al., Plant Cell 2:1201 (1990); RCc2 and RCc3, promoters that direct root-specific gene transcription in rice (Xu et al., Plant Mol. Biol. 27:237 (1995); TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$ −5° C. to $T_m$ −10° C. Medium or moderate stringency conditions are those providing $T_m$ −20° C. to $T_m$ −29° C. Low stringency conditions are those providing a condition of $T_m$ −40° C. to $T_m$ −48° C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \ G+C) - 500/L \ 0.63(\% \ \text{formamide}) \quad (2)$$

where L is the length of the probe in the hybrid. (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam.) The $T_m$ of equation (2) is affected by the nature of the hybrid; for DNA-RNA hybrids $T_m$ is 10–15° C. higher than calculated, for RNA-RNA hybrids $T_m$ is 20–25° C. higher. Because the $T_m$ decreases about 1° C. for each 1% decrease in homology when a long probe is used (Bonner et al., J. Mol. Biol. 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5–8° C. below $T_m$, medium or moderate stringency is 26–29° C. below $T_m$ and low stringency is 45–48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation.

Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise promoters and promoter control elements that are capable of modulating transcription, particularly in response to shade conditions, thereby enhancing the ability of a plant to grow under such shade conditions.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:

(a) antisense;
(b) ribozymes;
(c) coding sequences; or
(d) fragments thereof.

The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

3. Description of the Invention, Experimental Procedures and Results

A. Identifying and Isolating Promoter Sequences of the Invention

The promoters and promoter control elements of the present invention are presented in Tables 1 and 2 in the section entitled "The promoter" sequence in Table 2 in the sections entitled "Predicted promoter sequence" and "Sequence verification and confirmation" and as SEQ ID NOS. 3–30. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in the row titled "The spatial expression of the promoter-marker-vector". Polynucleotide libraries comprising genomic sequences can be constructed according to Sambrook et al., *Molecular Cloning: A Laboratory Manual*, $2^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR, and 5' rapid amplification of cDNA ends (RACE). See, for tail-PCR, for example, Liu et al., *Plant J* 8(3): 457–463 (September, 1995); Liu et al., *Genomics* 25: 674–681 (1995); Liu et al., *Nucl. Acids Res.* 21(14): 3333–3334 (1993); and Zoe et al., *BioTechniques* 27(2): 240–248 (1999); for RACE, see, for example, *PCR Protocols: A Guide to Methods and Applications*, (1990) Academic Press, Inc.

(2) Chemical Synthesis

In addition, the promoters and promoter control elements of the invention can be chemically synthesized according to techniques in common use. See, for example, Beaucage et al., *Tet. Lett.* (1981) 22: 1859 and U.S. Pat. No. 4,668,777.

Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Synthetic RNA, including natural and/or analog building blocks, can be synthesized on the Biosearch 8600 machines, see above.

Oligonucleotides can be synthesized and then ligated together to construct the desired polynucleotide.

B. Generating Reduced and "Core" Promoter Sequences

Included in the present invention are reduced and "core" promoter sequences. The reduced promoters can be isolated from the promoters of the invention by deleting at least one 5' UTR, exon or 3' UTR sequence present in the promoter sequence that is associated with a gene or coding region located 5' to the promoter sequence or in the promoter's endogenous coding region.

Similarly, the "core" promoter sequences can be generated by deleting all 5' UTRs, exons and 3' UTRs present in the promoter sequence and the associated intervening sequences that are related to the gene or coding region 5' to the promoter region and the promoter's endogenous coding region.

This data is presented in the row titled "Optional Promoter Fragments".

C. Isolating Related Promoter Sequences

Included in the present invention are promoter and promoter control elements that are related to those described in Table 1 in the section entitled "The promoter sequence". Such related sequence can be isolated utilizing (a) nucleotide sequence identity;
(b) coding sequence identity; or
(c) common function or gene products.

Such related sequences (or "relatives") can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in Tables 1 and 2 in the section entitled "The promoter sequence".

Definition

Typically, such related promoters exhibit at least 80% sequence identity, at least 85%, at least 90%, or at least 95%, including, at least 96%, 97%, 98% or 99% sequence identity compared to those shown in Tables 1 and 2 in the section entitled "The promoter" sequence. Such sequence identity can be calculated by the algorithms and computers programs described above.

Usually, such sequence identity is exhibited in an alignment region that is at least 75% of the length of a sequence shown in Tables 1 and 2 in the section entitled "The promoter" sequence or corresponding full-length sequence; more usually at least 80%; more usually, at least 85%, more usually at least 90%, and most usually at least 95%, even more usually, at least 96%, 97%, 98% or 99% of the length of a sequence shown in Tables 1 and 2 in the section entitled "The promoter sequence".

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in Tables 1 and 2 in the section entitled "The promoter sequence".

These related promoters may exhibit similar preferential transcription as those promoters described in Tables 1 and 2 in the section entitled "The promoter sequence".

Construction of Polynucleotides

Naturally occurring promoters that exhibit nucleotide sequence identity to those shown in Tables 1 and 2 in the section entitled "The promoter sequence" can be isolated using the techniques as described above. More specifically, such related promoters can be identified by varying stringencies, as defined above, in typical hybridization procedures such as Southern blots or probing of polynucleotide libraries, for example.

Non-natural promoter variants of those shown in Tables 1 and 2 can be constructed using cloning methods that incorporate the desired nucleotide variation. See, for example, Ho, S. N., et al. Gene 77:51–59 1989, describing a procedure site directed mutagenesis using PCR.

Any related promoter showing sequence identity to those shown in Tables 1 and 2 can be chemically synthesized as described above.

Also, the present invention includes non-natural promoters that exhibit the above-sequence identity to those in Tables 1 and 2.

The promoters and promoter control elements of the present invention may also be synthesized with 5' or 3' extensions, to facilitate additional manipulation, for instance.

The present invention also includes reduced promoter sequences. These sequences have at least one of the optional promoter fragments deleted.

Core promoter sequences are another embodiment of the present invention. The core promoter sequences have all of the optional promoter fragments deleted.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794–8797 (1992); Hamilton et al., Proc. Natl. Acad. Sci. USA 93: 9975–9979 (1996);
(b) YAC: Burke et al., Science 236:806–812 (1987);
(c) PAC: Sternberg N. et al., Proc Natl Acad Sci USA. January; 87(1):103–7 (1990);
(d) Bacteria-Yeast Shuttle Vectors: Bradshaw et al., Nucl Acids Res 23: 4850–4856 (1995);
(e) Lambda Phage Vectors: Replacement Vector, e.g., Frischauf et al., J. Mol Biol 170: 827–842 (1983); or Insertion vector, e.g., Huynh et al., In: Glover N.Mex. (ed) DNA Cloning: A practical Approach, Vol. 1 Oxford: IRL Press (1985); T-DNA gene fusion vectors:Walden et al., Mol Cell Biol 1: 175–194 (1990); and
(g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The promoter control elements of the present invention include those that comprise a sequence shown in Tables 1 and 2 in the section entitled "The promoter sequence" and those that comprise fragments of SEQ ID NOS. 3–30, but that still possess shade responsive activity. The size of the fragments can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Relatives Based on Nucleotide Sequence Identity

Included in the present invention are promoter control elements exhibiting nucleotide sequence identity to those described in Tables 1 and 2 in the section entitled "The promoter sequence" of fragments thereof.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in Tables 1 and 2 in the section entitled "The promoter sequence". Such sequence identity can be calculated by the algorithms and computers programs described above.

Promoter Motifs of the Invention

The promoter motifs of the present invention include those that comprise a sequence shown in Tables 1 and 2 in the section entitled "The promoter sequence" and those that comprise fragments of SEQ ID NOS. 3–30, but that still possess nitrogen responsive activity. The size of the motif can range from 2 bases to 500 bases. Typically, the motif size is no smaller than 3 bases; more typically, no smaller than 4; even more typically, no smaller than 5, 6, 7, 8, 9 or 10 bases.

Usually, the motif size is no longer than 500 bases; more longer than 40 bases; more usually, no larger than 30 bases; even more usually, no more than 25, 20 or 15 bases.

Promoter Control Element Configuration

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity and of transcriptional responses to particular environmental or nutritional factors, and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins, and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene, where an AP-1 site located about 900 nucleotides upstream of the transcription start site suppresses expression. Yamauchi et al., Matrix Biol., 15, 119–130 (1996). Alternatively, an AP-1 site located close to the transcription start site plays an important role in the expression of Moloney murine leukemia virus. Sap et al., Nature, 340, 242–244, (1989).

D. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments, variants, as well as full-length sequences those shown in Tables 1 and 2 in the section entitled "The promoter sequence" and relatives are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hindrance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements can be determined using the techniques and assays described above.

(4) Other Promoters

The shade responsive promoters, promoter control elements and motifs of the present invention can be combined in a construct with other known promoters to effect transcription in a desired manner. The following are promoters that are induced under stress conditions and can be combined with those of the present invention: 1dh1 (oxygen stress; tomato; see Germain and Ricard. 1997. Plant Mol Biol 35:949–54), GPx and CAT (oxygen stress; mouse; see Franco et al. 1999. Free Radic Biol Med 27:1122–32), ci7 (cold stress; potato; see Kirch et al. 1997. Plant Mol Biol. 33:897–909), Bz2 (heavy metals; maize; see Marrs and Walbot. 1997. Plant Physiol 113:93–102), HSP32 (hyperthermia; rat; see Raju and Maines. 1994. Biochem Biophys Acta 1217:273–80); MAPKAPK-2 (heat shock; Drosophila; see Larochelle and Suter. 1995. Gene 163:209–14).

In addition, the following examples of promoters are induced by the presence or absence of light can be used in combination with those of the present invention: Topoisomerase II (pea; see Reddy et al. 1999. Plant Mol Biol 41:125–37), chalcone synthase (soybean; see Wingender et al. 1989. Mol Gen Genet 218:315–22) mdm2 gene (human tumor; see Saucedo et al. 1998. Cell Growth Differ 9:119–30), Clock and BMAL1 (rat; see Namihira et al. 1999. Neurosci Lett 271:1–4, PHYA (*Arabidopsis*; see Canton and Quail 1999. Plant Physiol 121:1207–16), PRB-1b (tobacco; see Sessa et al. 1995. Plant Mol Biol 28:537–47) and Ypr10 (common bean; see Walter et al. 1996. Eur J Biochem 239:281–93).

The promoters and control elements of the following genes can be used in combination with the present invention to confer tissue specificity: MipB (iceplant; Yamada et al. 1995. Plant Cell 7:1129–42) and SUCS (root nodules; broadbean; Kuster et al. 1993. Mol Plant Microbe Interact 6:507–14) for roots, OsSUT1 (rice; Hirose et al. 1997. Plant Cell Physiol 38:1389–96) for leaves, Msg (soybean; Stomvik et al. 1999. Plant Mol Biol 41:217–31) for siliques, cell (*Arabidopsis*; Shani et al. 1997. Plant Mol Biol 34(6): 837–42) and ACT11 (*Arabidopsis*; Huang et al. 1997. Plant Mol Biol 33:125–39) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al. 1999. Plant Mol Biol41:443–54), the TAPG1 gene that is active during abscission (tomato; Kalaitzis et al. 1995. Plant Mol Biol 28:647–56), and the 1-aminocyclopropane-1-carboxylate synthase gene (carnation; Jones et al. 19951 Plant Mol Biol 28:505–12) and the CP-2/cathepsin L gene (rat; Kim and Wright. 1997. Biol Reprod 57:1467–77), both active during senescence.

E. Vectors

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., Nature 317: 741–744 (1985); Gordon-Kamm et al., Plant Cell 2: 603–618 (1990); and Stalker et al., Science 242: 419–423 (1988)). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element may modify-transcription by modulate transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for examples Vaucheret, H et al. (1998) *Plant J* 16: 651–659. The promoter or promoter control element may be simply inserted into a genome or maintained extrachromosomally as a way to divert transcription resources of the system to itself. This approach may be used to down regulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), Bacillus thuringiensis (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allows for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of A. tumefaciens, such as the octopine synthase and nopaline synthase termination regions. See also, Guerineau et al., (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. 1989) Nucleic Acids Res. 17:7891–7903; Joshi et al. (1987) Nucleic Acid Res. 15:9627–9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al., (1989) Nucleic Acids Res. 17:477–498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

F. Polynucleotide Insertion Into A Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide may be desired.

(2) Polynucleotides Integrated into the Host Genome

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition 10 Sprague et al. (Eds. pp. 345–387) American Society of Agronomy Inc. et al. 1988.

Methods of introducing polynucleotides into plant tissue include the direct infection or co-cultivation of plant cell with *Agrobacterium tumefaciens*, Horsch et al., Science, 227:1229 (1985). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) Plant Cell, Tissue and Organ Culture: Fundamental Methods, Springer Verlag, Berlin (1995).

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the exemplary promoters of the row titled "The promoter sequence" will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al., *Plant Mol. Biol.* 38:393 (1998)).

G. Using the Promoters of the Invention

Common Uses

In yet another embodiment, the promoters of the present invention can be used to further understand developmental mechanisms. For example, shade responsive promoters that are specifically induced during callus formation, somatic embryo formation, shoot formation or root formation can be used to explore the effects of over expression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues, K. Lindsey et al., 1993 "Tagging Genomic Sequences That Direct Transgene Expression by Activation of a Promoter Trap in Plants", Transgenic Research 2:3347. D. Auch & Reth, et al., "Exon Trap Cloning: Using PCR to Rapidly Detect and Clone Exons from Genomic DNA Fragments", Nucleic Acids Research, Vol. 18, No. 22, p. 674.

Entrapment vectors, first described for use in bacteria (Casadaban and Cohen, 1979, Proc. Nat. Aca. Sci. U.S.A., 76: 4530; Casadaban et al., 1980, J. Bacteriol., 143: 971) permit selection of insertional events that lie within coding sequences. Entrapment vectors can be introduced into pluripotent ES cells in culture and then passed into the germline via chimeras (Gossler et al., 1989, Science, 244: 463; Skarnes, 1990, Biotechnology, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. in Science 259: 686–688 (1993), Mahan et al. in PNAS USA 92:669–673 (1995), Heithoff et al. in PNAS USA 94:934–939 (1997), and Wang et al. in PNAS USA. 93:10434 (1996).

Constitutive Transcription

Use of promoters and control elements providing constitutive transcription is desired for modulation of transcription in most cells of an organism under most environmental conditions. In a plant, for example, constitutive transcription is useful for modulating genes involved in defense, pest resistance, herbicide resistance, etc.

Constitutive up-regulation and transcription down-regulation is useful for these applications. For instance, genes, transcripts, and/or polypeptides that increase defense, pest and herbicide resistance may require constitutive up-regulation of transcription. In contrast, constitutive transcriptional down-regulation may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows:

$$\int \varphi(x)dx, \text{ integrated from } a \text{ to } \infty,$$

where $\varphi(x)$ is a normal distribution, where $a = \dfrac{|Sx - \mu|}{\sigma(\text{all Samples except } Sx)}$;

where $Sx$ = the intensity of the sample of interest where $\mu$ = is the average of the intensities of all samples except $Sx$, $= \dfrac{(\Sigma S1 \ldots Sn) - Sx}{n-1}$ where $\sigma(S1 \ldots S11, \text{ not including } Sx)$ = the standard deviation of all sample intensities except $Sx$.

The P-value from the formula ranges from 1.0 to 0.0.

Usually, each P-value of the transcript levels observed in a majority of cells, tissues, or organs under various environmental conditions produced by the promoter or control element is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Dark or Shade Induced Preferential Transcription

Promoters and control elements providing preferential transcription when induced by dark or decreased light intensity (shade) or decreased light exposure time can be utilized to time growth, metabolism, and development, to modulate photosynthesis capabilities for host cells or, organisms. In a plant, for example, modulation of genes, transcripts, and/or polypeptides in response to dark is useful, for example, (1) to induce growth or development, such as fruit development and maturity, despite lack of light;

(2) to modulate genes, transcripts, and/or polypeptide active at night or on cloudy days; or (3) to preserve the plastid ultra structure present at the onset of darkness.

The present promoters and control elements can also trigger response similar to those described in the section above.

Up-regulation and transcription down-regulation is useful for these applications. For instance, genes, transcripts, and/or polypeptides that increase growth and development may require up-regulation of transcription. In contrast, transcriptional down-regulation may be desired to inhibit those genes, transcripts, and/or polypeptides that modulate photosynthesis capabilities.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

GFP Experimental Procedures and Results

Procedures

The polynucleotide sequences of the present invention were tested for promoter activity using Green Fluorescent Protein (GFP) assays in one of the following manner.

A. Shade Cloth Procedure

Approximately 1–2 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNewBin4-HAP1-GFP (see FIG. 1).

Transformation

The following procedure was used for transformation of plants

1. Stratification of WS-2 Seed.
   Add 0.5 ml WS-2 (CS2360) seed to 50 ml of 0.2% Phytagar in a 50 ml Corning tube and vortex until seeds and Phytagar form a homogenous mixture.
   Cover tube with foil and stratify at 4° C. for 3 days.

2. Preparation of Seed Mixture.
   Obtain stratified seed from cooler.
   Add seed mixture to a 1000 ml beaker.
   Add an additional 950 ml of 0.2% Phytagar and mix to homogenize.

3. Preparation of Soil Mixture.
   Mix 24 L SunshineMix #5 soil with 16 L Therm-O-Rock vermiculite in cement mixer to make a 60:40 soil mixture.
   Amend soil mixture by adding 2 Tbsp Marathon and 3 Tbsp Osmocote and mix contents thoroughly.
   Add 1 Tbsp Peters fertilizer to 3 gallons of water and add to soil mixture and mix thoroughly.
   Fill 4-inch pots with soil mixture and round the surface to create a slight dome.
   Cover pots with 8-inch squares of nylon netting and fasten using rubber bands.
   Place 14 4-inch pots into each no-hole utility flat.

4. Planting.
   Using a 60 ml syringe, aspirate 35 ml of the seed mixture.
   Exude 25 drops of the seed mixture onto each pot.
   Repeat until all pots have been seeded.
   Place flats on greenhouse bench, cover flat with clear propagation domes, place 55% shade cloth on top of flats and subirrigate by adding 1 inch of water to bottom of each flat.

5. Plant Maintenance.
   3 to 4 days after planting, remove clear lids and shade cloth.
   Subirrigate flats with water as needed.
   After 7–10 days, thin pots to 20 plants per pot using forceps.
   After 2 weeks, subirrigate all plants with Peters fertilizer at a rate of 1 Tsp per gallon water.
   When bolts are about 5–10 cm long, clip them between the first node and the base of stem to induce secondary bolts.
   6 to 7 days after clipping, perform dipping infiltration.

6. Preparation of *Agrobacterium*.
   Add 150 ml fresh YEB to 250 ml centrifuge bottles and cap each with a foam plug (IdentiPlug).
   Autoclave for 40 min at 121° C.
   After cooling to room temperature, uncap and add 0.1 ml each of carbenicillin, spectinomycin and rifampicin stock solutions to each culture vessel.
   Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.

Cap culture vessels and place on Lab-Line incubator shaker set at 27° C. and 250 RPM.

Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.

Pour out supernatant and put bottles on ice until ready to use.

Add 200 ml Infiltration Media (IM) to each bottle, resuspend *Agrobacterium* pellets and store on ice.

7. Dipping Infiltration.

Pour resuspended *Agrobacterium* into 16 oz polypropylene containers.

Invert 4-inch pots and submerge the aerial portion of the plants into the *Agrobacterium* suspension and let stand for 5 min.

Pour out *Agrobacterium* suspension into waste bucket while keeping polypropylene container in place and return the plants to the upright position.

Place 10 covered pots per flat.

Fill each flat with 1-inch of water and cover with shade cloth.

Keep covered for 24 hr and then remove shade cloth and polypropylene containers.

Resume normal plant maintenance.

When plants have finished flowering cover each pot with a ciber plant sleeve.

After plants are completely dry, collect seed and place into 2.0 ml micro tubes and store in 100-place cryogenic boxes.

Recipes:

0.2% Phytagar
  2 g Phytagar
  1 L nanopure water
    Shake until Phytagar suspended
    Autoclave 20 min YEB (for 1 L)
  5 g extract of meat
  5 g Bacto peptone
  1 g yeast extract
  5 g sucrose
    0.24 g magnesium sulfate
    While stirring, add ingredients, in order, to 900 ml nanopure water
    When dissolved, adjust pH to 7.2
    Fill to 1 L with nanopure water
    Autoclave 35 min Infiltration Medium (IM) (for 1 L)
  2.2 g MS salts
  50 g sucrose
  5 ul BAP solution (stock is 2 mg/ml)
    While stirring, add ingredients in order listed to 900 ml nanopure water
    When dissolved, adjust pH to 5.8.
    Volume up to 1 L with nanopure water.
    Add 0.02% Silwet L-77 just prior to resuspending *Agrobacterium*

High Throughput Screening—T1 Generation

1. Soil Preparation. Wear gloves at all times.
   In a large container, mix 60% autoclaved SunshineMix #5 with 40% vermiculite.
   Add 2.5 Tbsp of Osmocote, and 2.5 Tbsp of 1% granular Marathon per 25 L of soil.
   Mix thoroughly.

2. Fill Com-Packs With Soil.
   Loosely fill D601 Com-Packs level to the rim with the prepared soil.
   Place filled pot into utility flat with holes, within a no-hole utility flat.
   Repeat as necessary for planting. One flat set should contain 6 pots.

3. Saturate Soil.
   Evenly water all pots until the soil is saturated and water is collecting in the bottom of the flats.
   After the soil is completely saturated, dump out the excess water.

4. Plant the Seed.

5. Stratify the Seeds.
   After sowing the seed for all the flats, place them into a dark 4° C. cooler.
   Keep the flats in the cooler for 2 nights for WS seed. Other ecotypes may take longer.
   This cold treatment will help promote uniform germination of the seed.

6. Remove Flats From Cooler and Cover With Shade Cloth. (Shade cloth is only needed in the greenhouse)
   After the appropriate time, remove the flats from the cooler and place onto growth racks or benches.
   Cover the entire set of flats with 55% shade cloth. The cloth is necessary to cut down the light intensity during the delicate germination period.
   The cloth and domes should remain on the flats until the cotyledons have fully expanded. This usually takes about 4–5 days under standard greenhouse conditions.

7. Remove 55% Shade Cloth and Propagation Domes.
   After the cotyledons have fully expanded, remove both the 55% shade cloth and propagation domes.

8. Spray Plants With Finale Mixture. Wear gloves and protective clothing at all times.
   Prepare working Finale mixture by mixing 3 ml concentrated Finale in 48 oz of water in the Poly-TEK sprayer.
   Completely and evenly spray plants with a fine mist of the Finale mixture.
   Repeat Finale spraying every 3–4 days until only transformants remain. (Approximately 3 applications are necessary.)
   When satisfied that only transformants remain, discontinue Finale spraying.

9. Weed Out Excess Transformants.

Weed out excess transformants such that a maximum number of five plants per pot exist evenly spaced throughout the pot.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | pedicel receptacle nectary sepal petal filament anther pollen carpel style papillae vascular epidermis stomata trichome |
| Silique | stigma style carpel septum placentae transmitting tissue vascular epidermis stomata abscission zone ovule |
| Ovule | Pre-fertilization: inner integument outer integument embryo sac funiculus chalaza micropyle gametophyte<br>Post-fertilization: zygote inner integument outer integument seed coat primordia chalaza micropyle early endosperm mature endosperm embryo |
| Embryo | suspensor preglobular globular heart torpedo late mature provascular hypophysis radicle cotyledons hypocotyl |
| Stem | epidermis cortex vascular xylem phloem pith stomata trichome |
| Leaf | petiole mesophyll vascular epidermis trichome primordia stomata stipule margin |

T1 Mature: These are the T1 plants resulting from independent transformation events. These are screened between stage 6.50–6.90 (means the plant is flowering and that 50–90% of the flowers that the plant will make have developed) which is 4–6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal microscopy.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10–12 days. Cotyledons, roots, hypocotyls, petioles, leaves, and the shoot meristem region of individual seedlings were screened until two seedlings were observed to have the same pattern. Generally found the same expression pattern was found in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope
Inverted Leica DM IRB
Fluorescence filter blocks:
Blue excitation BP 450–490; long pass emission LP 515.
Green excitation BP 515–560; long pass emission LP 590
Objectives
HC PL FLUOTAR 5x/0.5
HCPL APO 10x/0.4 IMM water/glycerol/oil
HCPL APO 20x/0.7 IMM water/glycerol/oil
HCXL APO 63x/1.2 IMM water/glycerol/oil
Leica TCS SP2 confocal scanner
Spectral range of detector optics 400–850 nm.
Variable computer controlled pinhole diameter.
Optical zoom 1–32x.
Four simultaneous detectors:
Three channels for collection of fluorescence or reflected light.
One channel for transmitted light detector.
Laser sources:
Blue Ar 458/5 mW, 476 nm/5 mW, 488 nm/20 mW, 514 nm/20 mW.
Green HeNe 543 nm/1.2 mW
Red HeNe 633 nm/10 mW B. Far Red Induction (FRI) Procedure Promoter lines were constructed in the two-component (HAP1-VP16) GFP reporter system. All promote lines were in the WS-2 background except PR0924, which was in Columbia (Col-0) ecotype. Seeds were plated on sterile 0.5% sucrose, 1x MS agar media and cold treated at 4° C. for 3–4 days before plates are put into growth chambers. Shade line induction conditions were as follows: All sets were placed on Conviron growth room shelf (16 hr L, 8 hr D cycling lights conditions (PAR=70 $\mu E/m^2 s$; R:FR=10.66) for 7 days. At 7 days, after planting, plates for far red induction (FRI) were placed under continuous far red LED light only, and exposed for 1 hr, 4 hr, and 24 hr. PR0924 lines were subjected to an additional 48 hr and 72 hr of FRI. White light (control) set remained under continuous white light for the same time period. All GFP expression analyses were preformed using the Typhoon imaging system. An exemplary map of the promoter construct PR0924 is shown in FIG. 1.

The results of the Shade Cloth Procedure are set forth in Table 1, which includes various information about each shade responsive promoter or promoter control element of the invention including the nucleotide sequence, the spatial expression promoted by each promoter, and the corresponding results from different expression experiments.

TABLE 1

Promoter Reports for Results of Shade Cloth Procedure

Promoter Candidate ID: 15295937

Modulates the gene as identified by its GI number: 15235882

TABLE 1-continued

Promoter Reports for Results of Shade Cloth Procedure

The GenBank description of the gene: homeobox-leucine zipper protein HAT4 (HD-Zip protein 4)
[Arabidopsis thaliana] >gi|462281|sp|Q05466|HAT4_ARATH Homeobox-leucine zipper protein
HAT4 (HD-ZIP protein 4) (HD-ZIP protein ATHB-2) >gi|629516|pir||S31424 DNA-binding homeotic
protein The promoter sequence: (SEQ ID NO: 3)
caaccgtttttgtttagttcttctttaattaactttatcactaatgtttaaaagtaaaaaggttttttaaagtgtgcaacaagcgtgactctttggcctt
tagagtcatcaagaagggtaatcattttttttactctttctcgacaatagcaatcaaattatcattcccacttttaataatctcataaaataaagtcaa
tcatagttaaaatttgataaattccatggaaatgataaaaatttgattttactattgt The Ceres cDNA ID of the endogenous coding sequence to the promoter:

cDNA nucleotide sequence: (nucleotides 1–255 of SEQ ID NO: 4)
ATCTTCTATCTCTCAAAAGAAAAGCAGACAACTTTATTTGCAAAAACAGAGTTTTTTTTTCTTATCTTGAGAAAGTTCAACAGAAGATGATGTTCGAGA
AAGACGATCTGGGTCTAAGCTTAGGCTTGAATTTTCCAAAGAAACAGATCAATCTCAAATCAAATCCATCTGTTTCTGTTACTCCTTCTTCTTCTTCTT
TTGGATTATTCAGAAGATCTTCATGGAACGAGAGTTTTACTTCTTCAGTTCCAAACT Coding sequence: 13605987 (SEQ ID NO: 5)
MMFEKDDLGLSLGLNFPKKQINLKSNPSVSVTPSSSSFGLFRRSSWNESFTSSVPNSDSSQKETRTFIRGIDVNRPPSTAEYGDEDAGVSSPNSTVSSS
TGKRSEREEDTDPQGSRGISDDEDGDNSRKKLRLSKDQSAILEETFKDHSTLNPKQKQALAKQLGLRARQVEVWFQNRRARTKLKQTEVDCEFLRRCCE
NLTEENRRLQKEVTELRALKLSPQFYMHMSPPTTLTMCPSCEHVSVPPPQPQAATSAHHRSLPVNAWAPATRISHGLTFDALRPRS*

Promoter Candidate ID: 15295943

Modulates the gene as identified by its GI number: 15235927

The GenBank description of the gene: hypothetical protein [Arabidopsis thaliana] >gi|7486668|pir||
T04505 hypothetical protein F8F16.200 - Arabidopsis thaliana >gi|2827533|emb|CAA16541.1| hypo-
thetical protein [Arabidopsis thaliana] >gi|7270040|emb|CAB79856.1|

The promoter sequence: (SEQ ID NO: 6)
tgtttttcattttttttttcatttcgttactactaacagaacttttcatttatatcttgaaattttgttgtataactcaaataaagattgaaactaaca
tgatgatacttgtaattatctgattatttccttccatgtaaaccgatcaacatcagtcgtaaaacagaaaacaaaaaagacactgatcgacactcata
gcataacaaccgatcttagtatacatatgtgtgatatgttacgtcatatttagctcat The Ceres cDNA ID of the endogenous coding sequence to the promoter: 13618832 cDNA nucleotide sequence: (SEQ ID NO: 7)
ATGTCTGGTGTGTGGGTATTCAACAAAAACGGAGTCATGAGGCTGGTGGAGAATCCTTACAACCAATCCGCCGGAGATTCGTCGGAATCGTCCTCTTCC
GGTGGTAACCAGCAGCAGAGGATGAGGAGGAAAATTCTCGTCCATCTTCCAAGCAGCGAGGTTGTGTCTTCGTACGGATCACTTGAGAAGATCTTGAAG
AATCTTGGGTGGGAGAGGTACTACAGTGGAGACAATACCGATCATCTGCTCCAGTTCCACAAGAGAACTTCGATGATCTCATCTCTCCCTCGTGAC
TTCTCCAAGTTTAACTCTATTCACATGTATGATATCGTCGTCAAGAACCCTAACGTCTTCCATGTCCGTGACATGTAGTAGTCAATCATCCAAAACAAT
GGTTCAATATCATTCTCCGATCATCGCCGCTGGTGATATATCTATCATGTATATATATATGCAGGTTTTTATTTTGTCGTTGGGTGTTTTGTTTTTGG
TTTATTTTGTTTTTAATGCATTTAATGTACGTGTTTTCCGTTCGACGTCGATCGATTGGGGTGGGTTCAAGCTAGAGCCATTCTAATAACTTTTATCAT
TTTGTGATTTTAATGAAATTGTATCATGTTG Coding sequence: (SEQ ID NO: 8)
MSGVWVFNKNGVMRLVENPYNQSAGDSSESSSSGGNQQQRMRRKILVHLPSSEVVSSYGSLEKILKNLGWERYYSGDNTDHLLQFHKRTSIDLISLPRD
FSKFNSIHMYDIVVKNPNVFHVRDM*

Promoter Candidate ID: 15295955

Modulates the gene as identified by its GI number: 15226394

The GenBank description of the gene: hypothetical protein; protein id: At2g28400.1, supported by
cDNA: gi_17979316 [Arabidopsis thaliana] >gi|25350263|pir||D84684 hypothetical protein At2g28400
[imported] - Arabidopsis thaliana thaliana]

The promoter sequence: (SEQ ID NO: 9)
tcaataacaatttaacaaataccaagataatatataaagttaattaaagttttcagttctgcttattttttgagcaaatatagtgataataagacatttt
actttttaaaactcggaaaggatgcgttgtttttattaaaccttaaagtggtatttaaaatttcaaatatttttttaaaatttataaacgaaattcaagt
tttgagcaaatttgtttttaatatacgatagaatgataaataagtataaactgaagt The Ceres cDNA ID of the endogenous coding sequence to the promoter: 4905232 cDNA nucleotide sequence: (SEQ ID NO: 10)
cttaaaaccaaaaacaaagtttcatttcttcttcttcttgaaatggcgacgagcaagtgctactatccacggccaagccaccgtttcttcaccactgac
caacacgtcaccgccacttccgatttcgagctagacgaatgggatcttttcaataccggttcagattcctcttcaagtttcagctttagtgaccttaca
atcacatccggtcgaaccggaactaaccggcaaattcacggtggttctgactccggtaaagctgcgtcttcctcaccggttaacgtaccggactggtct
aagattcttggagacgagagtcgacgacagaggaagatttcgaatgaggaagaagttgacggagatgaaatttttatgcggcgaaggtacacggcgagtt
ccaccgcatgaattgcttgcgaaccggaggatggcttcgttttcggttcatgaaggtgctgggaggactttgaaaggaagagatctgagtagggtgcga
aatactattttttaaaa Coding sequence: (SEQ ID NO: 11)
MATSKCYYPRPSHRFFTTDQHVTATSDFELDEWDLFNTGSDSSSSFSFSDLTITSGRTGTNRQIHGGSDSGKAASSLPVNVPDWSKILGDESRRQRKIS
NEEEVDGDEILCGEGTRRVPPHELLANRRMASFSVHEGAGRTLKGRDLSRVRNTIFK TABLE 1-continued Promoter Reports for Results of Shade Cloth Procedure Promoter Candidate ID: 15295958

Modulates the gene as identified by its GI number: 11357157

The GenBank description of the gene: acyl CoA reductase-protein - Arabidopsis thaliana >gi|7635476|
emb|CAB88536.1| acyl CoA reductase-protein [Arabidopsis thaliana]

The promoter sequence: (SEQ ID NO: 12)
aagatagtacagtttcagtgttttgagaaaaaaagctgaactaaaactaaaatgtttaaggacacaatatttagtttcaattagataattcaacagttt
gaacaatttttttttttttttttgaagtcatttatttatacaatgttttaaaacgcattaagcatttaggcagccgacaaacgcctattgtctaactg
taaataggcgcttccacttaggttcatattgcatatttactatatgtgtatagtgac The Ceres cDNA ID of the endogenous coding sequence to the promoter: 13611606 cDNA nucleotide sequence: (nucleotides 1-255 of SEQ ID NO: 13)
ACGTGACTCAATAAAATCAAGTCTTTTGTTTCCTTTTATCCAAAAAAAAAAAAAAGTCTTGTGTTTCTCTTAGGTTGGTTGAGAATCATTTCATTTCAA
TGGAATCCAATTGTGTTCAATTTCTCGGTAACAAGACCATTCTCATCACAGGAGCTCCTGGTTTTCTTGCCAAGGTTTTGGTAGAGAAAATACTAAGGT
TGCAACCAAATGTGAAGAAGATATACCTTCTGTTGAGAGCTCCCGACGAAAAATCAG Coding sequence: (SEQ ID NO: 14)
MESNCVQFLGNKTILITGAPGFLAKVLVEKILRLQPNVKKIYLLLRAPDEKSAMQRLRSEVMEIDLFKVLRNNLGEDNLNALMREKIVPVPGDISIDNL
GLKDTDLIQRMWSEIDIIINIAATTNFDERYDIGLGINTFGALNVLNFAKKCVKGQLLLHVSTAYISGEQPGLLLEKPFKMGETLSGDRELDINIEHDL
MKQKLKELQDCSDEEISQTMKDFGMARAKLHGWPNTYVFTKAMGEMLMGKYRENLPLVIIRPTMITSTIAEPFPGWIEGLKTLDSVIVAYGKGRLKCFL
ADSNSVFDLIPADMVVNAMVAAATAHSGDTGIQAIYHVGSSCKNPVTFGQLHDFTARYFAKRPLIGRNGSPIIVVKGTILSTMAQFSLYMTLRYKLPLQ
ILRLINIVYPWSHGDNYSDLSRKIKLAMRLVELYQPYLLFKGIFDDLNTERLRMKRKENIKELDGSFEFDPKSIDWDNYITNTHIPGLITHVLKQ*

Promoter Candidate ID: 15295970

Modulates the gene as identified by its GI number: 15230001

The GenBank description of the gene: hypothetical protein; protein id: At3g29575.1, supported by
cDNA: gi_14326573 [Arabidopsis thaliana] >gi|14326574|gb|AAK60331.1|AF385741_1 AT3g29575/MWE13_2
[Arabidopsis thaliana] >gi|22137322|gb|AAM91506.1|

The promoter sequence: (SEQ ID NO: 15)
acggtcaaagtattgctaacatggtcattacattgaaaagaaaattaattgtctttactcatgtttattctatacaaataaaaatattaaccaaccat
cgcactaacaaaatagaaatcttattctaatcacttaattgttgacaattaaatcattgaaaaatacacttaaatgtcaaatattcgttttgcatactt
ttcaatttaaatacatttaaagttcgacaagttgcgtttactatcatagaaaactaa The Ceres cDNA ID of the endogenous coding sequence to the promoter: 12736859 cDNA nucleotide sequence: (nucleotides 1-255 of SEQ ID NO: 16)
AAATTCTCTTTGGGCTCTTAATTTCTTTTTGAGTGTTCGTTCTCGAGATTTGTCGGAGATTTTTTCGGTAAATGTTGAAATTTTGTGGGATTTTTTTTAT
TTCTTTATTAAACTTTTTTTTATTAATTTATAAAAAGGGAAGGTCGTCATTAATCGAAGAAATGGAATCTTCCAAAATTTGATATTTTGCTGTTTTCTT
GGGATTTGAATTGCTCTTTATCATCAAGAATCTGTTAAAATTTCTAATCTAAAATC Coding sequence: (SEQ ID NO: 17)
MSKKQRLSEEDGEVEIELDLGLSLNGRFGVDPLAKTRLMRSTSVLDLVVNDRSGLSRTCSLPVETEEEWRKRKELQSLRRLEAKRKRSEKQRKHKACGG
EEKVVEEGSIGSSGSGSSGLSEVDTLLPPVQATTNKSVETSPSSAQSQPENLGKEASQNIIEDMPFVSTTGDGPNGKKINGFLYRYRKGEEVRIVCVCH
GSFLSPAEFVKHAGGGDVAHPLKHIVVNPSPFL*

Promoter Candidate ID: 15295973

Modulates the gene as identified by its GI number: 15233496

The GenBank description of the gene: auxin-responsive protein IAA1 (Indoleacetic acid-induced
protein 1) [Arabidopsis thaliana] >gi|12644289|sp|P49677|AXI1_ARATH Auxin-responsive protein
IAA1 (Indoleacetic acid-induced protein 1)

The promoter sequence: (nucleotides 1-255 of SEQ ID NO: 74)
aaaatgttatttgagacagcatatcacatggccttaccatacttcctgcatccattattccattaagaacactcttcaccctcatccacatgcatctcc
ctccccaatttatttactattgatcataattgtacaaacctatacttacaatttatatatgtgtctacgagaaaataaataatattttacagtgttttg
tctattattttgttctatagtttcttgcaaacaaaacattacttttcacgcaaaaac The Ceres cDNA ID of the endogenous coding sequence to the promoter: 13617391 cDNA nucleotide sequence: (SEQ ID NO: 80)
ACACAAGCATTTTCAAGGATATCAAATCACAATCCCAAGAAGAGCAATAACAAGAGAAGAAGAAGTAGTTCAAGAATTAAGGAAGAGAGCTTCTCCGTT
AAAGTATAGTGAGAGAATATGGAAGTCACCAATGGGCTTAACCTTAAGGACACAGAGCTTCGTTTGGGATTACCCGGAGCACAGAAGAACAACAACTAG
AACTTTCTTGCGTCAGAGCAACAACAAGCGCAAGAACAACGACTCAACAGAAGAATCTGCTCCTCCTCCTGCAAAAACACAAATCGTTGGATGGCCTCC
AGTGAGATCTAACCGTAAGAACAACAACAACAAAAACGTGAGTTATGTGAAAGTGAGTATGGACGGAGCTCCATATCTCCGTAAGATAGATCTCAAGAT
GTACAAAAACTATCCAGAGCTTCTCAAAGCACTAGAGAACATGTTCAAGTTCACATAGGTGAATATTCCGAGAGAGAAGGCTACAAAGGATCTGGATT
TGTACCTACTTATGAAGACAAAGATGGAGATTGGATGTTGGTCGGTGATGTTCCATGGGACATGTTCTCTTCATCTTGTCAAAAACTCAGAATCATGAA
AGGATCCGAAGCTCCTACTGCCTTATGATCCATTGTCTCAAAACACCTTTTGGTCGAGGCAAAAACAAATTCTACTTTGTTTAGATAAAAAAAAGTTTG
GTGTAAGAAAGAAAAAGCAATAGGGTTACAAATACGTTATATAGATGTAAACTAGCTTTGGTTAATTCTGTAAAAGATGAGTTTTGATTATACGAAGTT
TATATGT TABLE 1-continued Promoter Reports for Results of Shade Cloth Procedure Coding sequence: (SEQ ID NO: 81)
MEVTNGLNLKDTELRLGLPGAQEEQQLELSCVRSNNKRKNNDSTEESAPPPAKTQIVGWPPVRSNRKNNNNKNVSYVKVSMDGAPYLRKIDLKMYKNYP
ELLKALENMFKFTVGEYSEREGYKGSGFVPTYEDKDGDWMLVGDVPWDMFSSSCQKLRIMKGSEAPTAL*

Promoter Candidate ID: 15295976

Modulates the gene as identified by its GI number: 15238721

The GenBank description of the gene: auxin-induced protein-like; protein id: At5g18060.1
[Arabidopsis thaliana] >gi|9757898|dbj|BAB08405.1| auxin-induced protein-like [Arabidopsis
thaliana]

The promoter sequence: (SEQ ID NO: 18)
gtgggacaaactagagcaagagttcacatggttctgtctctaccatttggaaaagatgcattaatgtaacttgtcttggtgagataattaacaaactcc
atatgcaattcacaagggcttgtttgctcaatgttttgtttagataagacatattctactgtcaataataaaggccagcaacttctctcttcttcaaatt
ctgtgatgatctattcttgaatctctgtggtctaaaattgtaaatgggggtttaataagaaattatagtgggtactgatgttgttcaacaacagaacaac
aaatcctatcgtttaaaacattgaaaaaacagtcctttgtgaacttatggagtttgttttttcgtttactgtcccacactcaatttattgttagattatc
tcatcaagacgaactgcattaaactaaatctttccagatggtaaagacataattgataggcaacataatcttagctcgccgtgagaatccatcttttgca
tatctgcttcaacaatggtttgctcatgagtaatctctcattctcataatctcatttcatgattaggctttttaaaaaaaatcttagctatgccaagct
cttgctaagaaaatgttcctcttggtaatgataatcacagtttatccaaaaaaaaaacaaaaaacagaaccatgtgaactctgtcccacgcttccaag
caatccattaacttgaatctttcatacatcttttcagaagctttaaaaataattcaaactttcagacaaaagaa The Ceres cDNA ID of the endogenous coding sequence to the promoter: 4945558 cDNA nucleotide sequence: (SEQ ID NO: 19)
atcaaccaacaccaagcaatccattaacttgaatctttcatacatcttttcagaagctttaaaaataattcaaactttcagacaaaagaaatggctttg
gtgagaagtctattggttgcaaagaagattcttagccgctccgccgcagcagtctcggcgccaccaaaagggtttcttgcagtgtacgtaggagagagc
cagaagaagagatatttagtgccactctcatacttgaaccagccttcttttcaagctctgctcagtaaatccgaagaagagtttgggttcgatcatccg
atgggtggcttaacgatcccttgtcccgaagatactttcatcaatgtgacttctcggctccattgatgattatccaacatagtgttttttcgagttaga
gatagagttgtttccttgtaaatagaggaattttttgttcctttttttttttttttttctctttcatcttgaaaaagttcttctaaattttttggaag
tggatgtagatgcagttttttgtgctatatacacaatcataattcatgttaacacattttggatcgattatggaaaaagaatggatat
cacc Coding sequence: (SEQ ID NO: 20)
MALVRSLLVAKKILSRSAAAVSAPPKGFLAVYVGESQKKRYLVPLSYLNQPSFQALLSKSEEEFGFDHPMGGLTIPCPEDTFINVTSRLH*

Promoter Candidate ID: 15295997

Modulates the gene as identified by its GI number: 18406162

The GenBank description of the gene: expressed protein [Arabidopsis thaliana] >gi|21592337|gb|
AAM64288.1| unknown [Arabidopsis thaliana] >gi|26451672|dbj|BAC42932.1| unknown protein
[Arabidopsis thaliana] >gi|28973149|gb|AAO63899.1| unknown protein
[Arabidopsis thaliana]

The promoter sequence: (SEQ ID NO: 82)
tagctagatttctatataaacagaagaaagttaaaaagcaaataaaaattcacaaatagaaatcgaacaaaaagctatgaaaatataaataccataacc
ttatgaaaaacgatgaaatgcttaacaaaaaaaactttggcaatggcatgcatgtgcctgtaacagaaggcccccataagctgttagtgatatacaac
ttaagcaaatgtgcactcttcacgcacttcccgcttttctaaatttcaatttatttg The Ceres cDNA ID of the endogenous coding sequence to the promoter: 13486695 cDNA nucleotide sequence: (SEQ ID NO: 22)
GCCATCTTCTTCATTATCATCATCTCCATCTCTCTCTCTCTCATTTTCTTGAAAAAGATGAGAACCTTAAAGACTCAGACCACAAGGGGAAGA
AGAAGAGCAAATGTGTCGTCACGTACGAGAGTTTTACACACGTGCTGTGGAAATGGTAGTAGCGACGGAGGGAAGACGGTGATGGAGAAGCTTCTTGCG
TTAAAGAGCCTTCTTCCTCCACCGGTGAATGTCGGTGGTGGAGACGGAGGAGCTGTTTCAAGAGACGGCGGAGTATATCGTGAAGCTTAGAACACAA
GTCGTGGTGTTGAAGAAACTGATTGAGATTTACGATAACTCTTCTGATCAGAAGAAAGATGTTGTTTTATAATGTTCATTTATATTTTCTTTAATTTAA
ATTATTTCAGGTTTTTCTGTTTTTTTTTGTTATAAACTTATAATTATTATATTGTGATCCGTAATGGTTTTAGGTTGTCCATGTCTTTAATGTATTGGT
TTAAAGGAAAAAGTATTGATGATTG Coding sequence: (SEQ ID NO: 23)
MRTLKTQTTRGRRRANVSSRTRVLHTCCGNGSSDGGKTVMEKLLALKSLLPPPVNVGGGETEELFQETAEYIVKLRTQVVVLKKLIEIYDNSSDQ
KKDVVL*

Promoter Candidate ID: 15295940

Modulates the gene as identified by its GI number: 18417976

The GenBank description of the gene: Expressed protein; protein id: At4g32280.1, supported by cDNA:
gi_14190492 [Arabidopsis thaliana]

The promoter sequence: (nucleotides 1–255 of SEQ ID NO: 58)
cagccgtaaatccttccataaatttattttgcaagttttgctcattatataatgagcggaatttatgatataatcgtttgtaataatgttatgttttg
atcaaaatttgaaattaaaagtaggtgagaacttgttatacagtgtagataaggtggatcttgaatataaaaataaaatttataagatgtatttaaag
cagaaaagcataaaactttagataaaataatgtaaaaatgtgttagcatcaatgttggg The Ceres cDNA ID of the endogenous coding sequence to the promoter: 12655184

TABLE 1-continued

Promoter Reports for Results of Shade Cloth Procedure cDNA nucleotide sequence: (SEQ ID NO: 83)
AATCAACACCAACGAACACAACCTTTTCCAAAGCCAATAATAAAAGAACAAAAGCTTTTAGTTTCATCAAAGACGAAGCTGCCTTAGAAATGGAGTTGG
ATCTTGGTCTATCTCTTTCACCTCATAAATCTTCCAAGTTAGGGGTTTAACTTTGACCTCAACAAGCATTGTGCGATCGAGGGTGCTGCGTCTTGTTTGG
GTACCGAAAAACTGCGTTTTGAGGCGACGTTTGGGTTAGGGAATGTGGAGGAAAATT Coding sequence: (SEQ ID NO: 26)
MELDLGLSLSPHKSSKLGFNFDLNKHCAIEGAASCLGTEKLRFEATFGLGNVEENCYMPKQRLFALNGQPNEEDEDPLESESSIVYDDEEENSEVVGWP
PVKTCMIKYGSYHHRHIRHIRNHHHCPYHHRGRRITAMNNNISNPTTATVGSSSSSSISSRSSMYVKVKMDGVAIARKVDIKLFNSYESLTNSLITMFT
EYEDCDREDTNYTFTFQGKEGDWLLRGDVTWKIFAESVHRISIIRDRPCAYTRCLF*

Promoter Candidate ID: 15295946

Modulates the gene as identified by its GI number: 18378953

The GenBank description of the gene: bHLH protein (HFR1) [Arabidopsis thaliana] >gi|20532238|sp|
Q9FE22|HFR1_ARATH Long hypocotyl in far-red 1 (bHLH-like protein HFR1) (Reduced phytochrome
signaling) (Basic helix-loop-helix FBI1 protein) (Reduced sensitivity to far-red The promoter sequence: (SEQ ID NO: 21)
aatttatctctatgttcatgtgtcaaagtggtagtgaatctagtgacgttattgattaatcaagattacttttatctttctgtgcaaaatttcaagat
tactctaaagtcgatatatgctactatgacgtagttttgggacaattacgtatagaatcataaaaacaataagcagaataataatccatttaagtaca
ttgtgaatttgtgataatggaattatttgacaatacttttccaaaataaaaactaatttaattactgtattaattattttagtaaaacaatattttca
ttacaatgtttgttgtgaatcaaaaaagtattgtttccaaagaactcaaatgacatcaatatgtctataataacctcgtgtagctgtatgttagaat
ctagccgaattgttttattgttgtcggtgtacgcaacaaacgaaccacacatactttgaaacgtggcacaatataagtgggtcaccaatgtagctgac
aactataccatctatctgatccgatcgctcttataacataagcgtatgggataccattttctcggacaaagctgaaatccctaaagaaaaaacacttc
tccaaacttttcatctccgatatctctttaactaac The Ceres cDNA ID of the endogenous coding sequence to the promoter: 13488199 cDNA nucleotide sequence: (SEQ ID NO: 84)
TAAGTGGGTCACCAATGTAGCTGACAACTATACCATCTATCTGATCCGATCGCTCTTATAACATAAGCGTATGGGATACCATTTTCTCGGACAAAGCTG
AAATCCCTAAAGAAAAAACACTTCTCCAAACTTTTCATCTCCGATATCTCTTTAACTAACATGTCGAATAATCAAGCTTTCATGGAATTGGGATGGAGA
AACGACGTCGGATCACTTGCTGTGAAAGATCAGGGCATGATGTCAGAAAGAGCAAGA Coding sequence: (SEQ ID NO: 85)
MSNNQAFMELGWRNDVGSLAVKDQGMMSERARSDEDRLINGLKWGYGYFDHDQTDNYLQIVPEIHKEVENAKEDLLVVVPDEHSETDDHHHIKDFSERS
DHRFYLRNKHENPKKRRIQVLSSDDESEEFTREVPSVTRKGSKRRRRDEKMSNKMRKLQQLVPNCHKTDKVSVLDKTIEYMKNLQLQLQMMSTVGVNPY
FLPATLGFGMHNHMLTAMASAHGLNPANHMMPSPLIPALNWPLPPFTNISFPHSSSQSLFLTTSSPASSPQSLHGLVPYFPSFLDFSSHAMRRL*

Promoter Candidate ID: 15295949

Modulates the gene as identified by its GI number: 18415376

The GenBank description of the gene: sulfotransferase family [Arabidopsis thaliana] >gi|20466686|
gb|AAM20660.1| steroid sulfotransferase-like protein [Arabidopsis thaliana] >gi|21537216|gb|
AAM61557.1| steroid sulfotransferase-like protein [Arabidopsis thaliana]

The promoter sequence: (SEQ ID NO: 24)
aaaaccgttagtttgtaaaaccaagccggaaagagaaaacttatattattaatcatatgcaaatatttattaaaatagttataatataatataatca
aatatataattttttcaaagttcttttttacacagaaccaaactgaaattgcgtcaaacctaagcaaaaacctaacctgaatcactactagttgagatt
gcattaaaaaaaaattgataaagaaaacaaaatcagtcaattttctattttattttactaggg The Ceres cDNA ID of the endogenous coding sequence to the promoter: 13492429 cDNA nucleotide sequence: (nucleotides 1-255 of SEQ ID NO: 25)
ACACCAACACACAAAGATTCCATTACAAATAAACAATTTTCATATATATCTATAACAAAAAAAAACAATGGCTACCTCAAGCATGAAGAGCATTCCAAT
GGCGATCCCAAGTTTCTCCATGTGTCACAAGCTCGAGCTCCTTAAAGAAGGCAAAACTCGCGACGTCCCGAAAGCCGAAGAAGATGAAGGGCTAAGCTG
CGAGTTCCAAGAGATGTTGGATTCTCTTCCTAAGGAGAGAGGATGGAGAACTCGTTA Coding sequence: (SEQ ID NO: 29)
MATSSMKSIPMAIPSFSMCHKLELLKEGKTRDVPKAEEDEGLSCEFQEMLDSLPKERGWRTRYLYLFQGFWCQAKEIQAIMSFQKHFQSLENDVVLATI
PKSGTTWLKALTFTILNRHRFDPVASSTNHPLFTSNPHDLVPFFEYKLYANGDVPDLSGLASPRTFATHLPFGSLKETIEKPGVKVVYLCRNPFDTFIS
SWHYTNNIKSESVSPVLLDQAFDLYCRGVIGFGPFWEHMLGYWRESLKRPEKVFFLRYEDLKDDIETNLKRLATFLELPFTEEEERKGVVKAIAELCSF
ENLKKLEVNKSNKSIKNFENRFLFRKGEVSDWVNYLSPSQVERLSALVDDKLGGSGLTFRLS*

Promoter Candidate ID: 15295952

Modulates the gene as identified by its GI number: 15241451

The GenBank description of the gene: putative protein; protein id: At5g44260.1, supported by cDNA:
gi_14334449 [Arabidopsis thaliana] >gi|10176881|dbj|BAB10111.1|gb|AAD10689.1~gene_id:K9L2.1~
similar to unknown protein [Arabidopsis thaliana]

The promoter sequence: (nucleotides 1-255 of SEQ ID NO: 70)
ttgtttaacacctcaaacctgttaagactaatcacaatgttcgaagataatgccatttctatatatatttagtatagcatcacacatgcgttctgtgtt
gcaaagtttactctagagttatcactgagtcatgactcatgatgaccattattatagtattagtacttttaagttttaggtcgagaatatgaagctaat

TABLE 1-continued

Promoter Reports for Results of Shade Cloth Procedure acatgcatgtaatgatgtaaatatgcctaccttaaaaaatatcgaattattcagaaa The Ceres cDNA ID of the endogenous coding sequence to the promoter: 12601699 cDNA nucleotide sequence: (SEQ ID NO: 86)
ATCCCACACTTATCTCTTCCTATCTCTCTCTCATTCAAACCCAAATAGGAAACAAATACACAAAAGTATAATAAAAAGTCTTTCTCTCATCTTTCGCCA
CGTAGACATGGACGTCGAACATCACAAATCCGGCCACATCAGTAGACCAACGGTGGATATTCCACCGAGGAAGCTTCTTTCCTCCGCCAAGTCTCCGTC
GTCAGTTTCAAGTCCCCTTCGCGACTATAAAGAACAGAAAGACTATTGTTACGACTC Coding sequence: (SEQ ID NO: 87)
SHTYLFLSLSHSNPNRKQIHKSIIKSLSLIFRHVDMDVEHHKSGHISRPTVDIPPRKLLSSAKSPSSVSSPLRDYKEQKDYCYDSDSEDPYAGDHFRMY
EFKIRRCTRSRSHDWTDCPFSHPGEKARRRDPRRFHYTGEVCPEFSRHGDCSRGDECGFAHGVFECWLHPSRYRTEACKDGKHCKRKVCFFAHSPRQLR
VLPPSPENHISGGCGGSPSSSPASVLSNKNNRCCLFCSHSPTSTLLNLSRSPSSSPPLSPADKADAFSRLSRRRTAVLNELISSLDSLSLTEALAASSS
SPVTMPISTATMIASSNLSSNHHHHRLPPWLDVGDRDLQLQQSSPLRFALSPSSTPSYLHGQLQPPPSSFFGDEFTPRGGRLSDFSVAAAAAAQARDKN
SFEVGSSGDLDLGWVNDLLT*

Promoter Candidate ID: 15295961

Modulates the gene as identified by its GI number: 15218709

The GenBank description of the gene: flowering signals mediating protein FT; protein id:
At1g65480.1, supported by cDNA: gi_17529185 [Arabidopsis thaliana] >gi|17432933|sp|Q9SXZ2|FT_ARATH
FLOWERING LOCUS T protein >gi|25346243|pir||T52447 FT protein [validated] - Arabidopsis The promoter sequence: (SEQ ID NO: 27)
ataatatggccgcttgtttataaaaaagaagagaaataaaacaattgatttggtttatattatttaattgcagatatcttgtacttaattcattttga
gataattttgcgtatttgagttcggacattggtaggtatggacgatgaaaataactgccttcattctacatgtttgagatttgtttgtcgaccatataa
cacaagcggctagaaaaataggtgactattctcaaatgtcctggttctatctaacct The Ceres cDNA ID of the endogenous coding sequence to the promoter: 12581196 cDNA nucleotide sequence: (SEQ ID NO: 28)
ACAATTAAAGAAGCAGAAACAAAAACAAGTAAAACAGAAACAATCAACACAGAGAAACCACCTGTTTGTTCAAGATCAAAGATGTCTATAAATATAAGA
GACCCTCTTATAGTAAGCAGAGTTGTTGGAGACGTTCTTGATCCGTTTAATAGATCAATCACTCTAAAGGTTACTTATGGCCAAAGAGAGGTGACTAAT
GGCTTGGATCTAAGGCCTTCTCAGGTTCAAAACAAGCCAAGAGTTGAGATTGGTGGAGAAGACCTCAGGAACTTCTATACTTTGGTTATGGTGGATCCA
GATGTTCCAAGTCCTAGCAACCCTCACCTCCGAGAATATCTCCATTGGTTGGTGACTGATATCCCTGCTACAACTGGAACAACCTTTGGCAATGAGATT
GTGTGTTACGAAAATCCAAGTCCCACTGCAGGAATTCATCGTGTCGTGTTTATATTGTTTCGACAGCTTGGCAGGCAAACAGTGTATGCACCAGGGTGG
CGCCAGAACTTCAACACTCGCGAGTTTGCTGAGATCTACAATCTCGGCCTTCCCGTGGCCGCAGTTTTCTACAATTGTCAGAGGGAGAGTGGCTGCGGA
GGAAGAAGACTTTAGATGGCTTCTTCCTTTATAACCAATTGATATTGCATACTCTGATGAGATTTATGCATCTATAGTATTTTAATTTAATAACCATTT
TATGATACGAGTAACGAACGGTGATGATGCCTATAGTAGTTCAATATATAAGTGTGTAATAAAAATGAGAGGGGGAGGAAAATGAGAGTGTTTTACTTA
TATAGTGTGTGATGCGATAATTATATTAATCTACATGAAATGAAGTGTTATATTTATACTTT Coding sequence: (SEQ ID NO: 88)
MSINIRDPLIVSRVVGDVLDPFNRSITLKVTYGQREVTNGLDLRPSQVQNKPRVEIGGEDLRNFYTLVMVDPDVPSPSNPHLREYLHWLVTDIPATTGT
TFGNEIVCYENPSPTAGIHRVVFILFRQLGRQTVYAFGWRQNFNTREFAEIYNLGLPVAAVFYNCQRESGCGGRRL*

Promoter Candidate ID: 15295964

Modulates the gene as identified by its GI number: 21554820

The GenBank description of the gene: putativepod-specific dehydrogenase SAC25 [Arabidopsis thaliana]

The promoter sequence: (nucleotides 24-279 of SEQ ID NO: 66)
aattaaatgaaactcgccctaaattaggagggatttgggtaagtggtaacacattcactggaaacatgtgaagaaaggaggatgtcaagtagctgaaa
actcagtatagtaaccaacggcttctcaccaacctttcattaataatttggtcatccctatattttattcaacattttgttttcaatagcttagagc
accttaataccttcagtgtttttttataaaaaaaacaaaaattgggattaatcat The Ceres cDNA ID of the endogenous coding sequence to the promoter: 12712683 cDNA nucleotide sequence: (SEQ ID NO: 89)
CTCCCAAACCTATCTTCTTCTTCCTCTCTTGTCTCTCTCGCTCTCTCTCTTCTACATTGTTTCTTGAGGTCAATCTATTAAAAATGGGATTATATTCAC
TAATCACAGGAAGAAGAGGACCAAGTGGATTTGGTTCAGCTTCAACAGCTGAAGAGGTTACTCAAGGGATTGATGCAACTAATCTCACTGCAATTATCA
CAGGAGGGACAGGAGGAATAGGGATGGAGACAGCGAGAGTGCTGTCGAAGAGAGGTG Coding sequence: (SEQ ID NO: 90)
MGLYSLITGRRGPSGFGSASTAEEVTQGIDATNLTAIITGGTGGIGMETARVLSKRGAHVVIGARNMGAAENAKTEILRQNANARVTLLQLDLSSIKSI
KAFVREFHALHLPLNLLINNAGVMFCPYQLSEDGIELQFATNHIGHFLLTNLLLDTMKNTAKTSGVEGRILNVSSVAHIYTVQEGIQFDSINDICSYSD
KRAYGQSKLANILHANELSRQLQEEGVNITANSVHPGLILTNLFQHTALLMRFLKFFSFYLWKNIPQGAATTCYVALHPSVKGVTGKYFADCNEVTPSK
LARDETLAQKLWDFSVKLINSVSKKNYLGFDDTT*

Promoter Candidate ID: 15295967

Modulates the gene as identified by its GI number: 15241765

The GenBank description of the gene: putative protein; protein id: At5g62280.1 [Arabidopsis thaliana]
>gi|8809641|dbj|BAA97192.1|gb|AAE82627.1~gene_id:MMI9.11~similar to unknown protein [Arabidopsis
thaliana]

TABLE 1-continued

Promoter Reports for Results of Shade Cloth Procedure

The promoter sequence: (SEQ ID NO: 30)
taagaaaaactgtnggcttgttgtcagaacaaacatggacccatgttctctatgtccctaagatgtgtaccaatctcaattcacttcttttgttgcact
attttttaaaaaataacttttattttatattttgagatctccattgccctgctgcactagacattacagctcatttttcttataattcaatcccta
gctatttttctttcttattagtttaaactaatcatatttgggtaattagcgttgaaa The Ceres cDNA ID of the endogenous coding sequence to the promoter: 12732583 cDNA nucleotide sequence: (SEQ ID NO: 31)
ATGGCTTTTTGGTCTGCTGAGAATGCTACTAAAGCCTATCTTAGTACATTGAAAACGGATCAAAGGACAAAAGAACCAAACGTCGCCGAATTCATATCA
GCCCTAGCCGCCGGAAATAGCGCTAGAAAGATAGCCGTGGCTTGCGCCGGAGCAGCAAACGCCGACATACTCGTTGCACTAATCGCAGCGGCTAACCAA
ACGCGTGGTCAAGTTGTATGCGTTTTACGTGGTATCGAAGAACTAATCATATCCAAAAAATGTTGGAACCATCAGAGATTCATCAGATACAATTCGTA
GTCGGAGAATCTAACGACGACACTCTAATCAATAATCATTTCGGAGAAGCAGATTTCGTCCTCGTGGATTGTAACCTCGAAAACCACCAAGAGATCGTT
GGAAAAATCCTTAATCATCACGAAGAAAACGCAAGAACCGGGTGGAAGCGGTGTGGCGGTTGTGGTGGGTTATAACGCGTTTTCGAGAGGGTCATGG
AGGTTTAGCGATGGAAGGAAAACGCAGTTTTTACCTATAGGAGAAGGGTTACTTGTGACGAGGGTCAATGATAATCAGAAGATGATGATGAAAAATCAC
CATCGTGACCAAGTGATGAGGAAGAGTCGTTGGGTGGTGAAGGTTGATAAGTGCACTGGAGAGGAACATGTGTTTAGGGTTAGGGTTCCCGAGGAGAA
GCCATTATTGAAGCTTAA Coding sequence: (SEQ ID NO: 32)
MAFWSAENATKAYLSTLKTDQRTKEPNVAEFISALAAGNSARKIAVACAGAANADILVALIAAANQTRGQVVCVLRGIEELIISQKMLEPSEIHQIQFV
VGESNDDTLINNHFGEADFVLVDCNLENHQEIVGKILNHHEENARTGGGSGVAVVVGYNAFSRGSWRFSDGRKTQFLPIGEGLLVTRVNDNQKMMMKNH
HRDQVMRKSRWVVKVDKCTGEEHVFRVRVPRGEAIIEA*

Promoter Candidate ID: 15295985

Modulates the gene as identified by its GI number: 34910002

The GenBank description of the gene: putative cytokinin oxidase [Oryza sativa (japonica cultivar-
group)] >gi|22202687|dbj|BAC07345.1| putative cytokinin oxidase [Oryza sativa (japonica cultivar-
group)]

The promoter sequence: (nucleotides 1—255 of SEQ ID NO: 76)
cactacacacgtgtgacctcatcctctcccacgtgaatatccacgtggcgttcttccgttccgtttctcccatccctcccatgcctctcccatgactc
tatttatcccaatcctctcttcctttcattaatttatcagttaaaattcctcttttttcctagtagtatttggagttttcatatcaaaaagtttagact
aaccctaaaaacattgatagaaaaacttatcattttaaacgttcttggggaccaatc The Ceres cDNA ID of the endogenous coding sequence to the promoter: 12721545 cDNA nucleotide sequence: (SEQ ID NO: 91)
ATGAATCGTGAAATGACGTCAAGCTTTCTTCCTGACGTTCGCCATATGTAAACTGATCATAGCCGTGGGTCTAAACGTGGGCCCCAGTGAGCTCCTC
CGCATCGGAGCCATAGATGTCGACGGCCACTTCACCGTCCACCCTTCCGACTTAGCCTCCGTCTCCTCAGACTTCGGTATGCTGAAGTCACCTGAAGAG
CCATTGGCCGTGCTTCATCCATCATCGGCCGAAGACGTGGCACGACTCGTCAGAACA Coding sequence: (SEQ ID NO: 92)
MNREMTSSFLLLTFAICKLIIAVGLNVGPSELLRIGAIDVDGHFTVHPSDLASVSSDFGMLKSPEEPLAVLHPSSAEDVARLVRTAYGSATAFPVSARG
HGHSINGQAAAGRNGVVVEMNHGVTGTPKPLVRPDEMYVDVWGGELWVDVLKKTLEHGLAPKSWTDYLYLTVGGTLSNAGISGQAFHHGPQISNVLELD
VVTGKGEVMRCSEEENTRLFHGVLGGLGQFGIITRARISLEPAPQRVRWIRVLYSSFKVFTEDQEYLISMHGQLKFDYVEGFVIVDEGLVNNWRSSFFS
PRNPVKISSVSSNGSVLYCLEITKNYHDSDSEIVDQEVEILMKKLNFIPTSVFTTDLQYVDFLDRVHKAELKLRSKNLWEVPHPWLNLFVPKSRISDFD
KGVFKGILGNKTSGPILIYPMNKDKWDERSSAVTPDEEVFYLVALLRSALTDGEETQKLEYLKDQNRRILEFCEQAKINVKQYLPHHATQEEWVAHFGD
KWDRFRSLKAEFDPRHILATGQRIFQNPSLSLFPPSSSSSSAASW*

Promoter Candidate ID: 15295988

Modulates the gene as identified by its GI number: 38605153

The GenBank description of the gene: Probable xyloglucan endotransglucosylase/hydrolase protein 15
precursor (At-XTH15) (XTH-15) >gi|1244760|gb|AAB18368.1| xyloglucan endotransglycosylase-related
protein >gi|15028017|gb|AAK76539.1|

The promoter sequence: (SEQ ID NO: 33)
gtcgacgctacaatgttgatttattggttgtggtttgcatcttggggatgtcaaatcctaagtttcaagttcttgtaaaaacgttttcaggtttcttta
atatattttaatattaatgtaaaaagaaaagatatagcttttgtacaaaaaaatttgtttaatcactatgtaggaggatgcgatcaaattcatggaatg
atgtattattagcttttctatcctcactcaaaaacaatactatagtgagttaaata The Ceres cDNA ID of the endogenous coding sequence to the promoter: 12711515 cDNA nucleotide sequence: (nucleotides 1—255 of SEQ ID NO: 34)
ATCTCACACCAAAACACAAAGCTCTCATCTTCTTTTAGTTTCCAAACTCACCCCCACAACTTTCATTTCTATCAACCAAACCCAAATGGGTCCAAGTTC
GAGCCTCACCACCATCGTGGCGACTGTTCTTCTTGTGACATTGTTCGGTTCGGCCTACGCAAGCAACTTCTTCGACGAGTTTGACCTCACTTGGGGTGA
CCACAGAGGCAAAATCTTCAACGGAGGAAATATGCTGTCTTTGTCGCTGGACCAGGT Coding sequence: (SEQ ID NO: 35)
MGPSSSLTTIVATVLLVTLFGSAYASNFFDEFDLTWGDHRGKIFNGGNMLSLSLDQVSGSGFKSKKEYLVGRIDMQLKLVAGNSAGTVTAYYLSSQGAT
HDEIDFEFLGNETGKPYVLHTNVFAQGKGDREQQFYLWFDPTKNFHTYSIVWRPQHIIFLVDNLPIRVFNNAEKLGVPFPKSQPMRIYSSLWNADDWAT
RGGLVKTDWSKAPFTAYYRGFNAAACTASSGCDPKFKSSFGDGKLQVATELNAYGRRRLRWVQKYFMIYNYCSDLKRFPRGFPPECKKSRV*

Promoter Candidate ID: 15295991

TABLE 1-continued

Promoter Reports for Results of Shade Cloth Procedure

Modulates the gene as identified by its GI number: 15227116

The GenBank description of the gene: cytochrome P450, putative; protein id: At2g21910.1 [*Arabidopsis thaliana*] >gi|25282629|pir||F84606 probable cytochrome P450 [imported] - *Arabidopsis thanliana* >gi| 4417283|gb|AAD20408.1| putative cytochrome P450 [*Arabidopsis thaliana*]

The promoter sequence: (SEQ ID NO: 36)
gattgaatgatgagtgtgcacccttgtattactaataaaaaatttagcaacagttataagctaacgtcatccatgagtcattcattagattcactattt
gcgttctcaaaaatcgaattgttaaaatttgagaagctctaatatacgagtcaatgagatgtggcaaaagcatgtccttgaccataaaatttcgagggg
tcaactcattagataaggacaagaatcaaccaattgaaggcgtcttctataacaagt The Ceres cDNA ID of the endogenous coding sequence to the promoter: 12734860 cDNA nucleotide sequence: (nucleotides 1–255 of SEQ ID NO: 37)
ATGGCTTACGTAGGCTTAGTTGAAGTCTTTATTGCCTTACTTGTCTTTTTCTTCTTCCATTTCTTGATCCACAAGAAATCTCATCAAATCACACCTAGA
AACTGGCCAGTTCTTGGGATGCTTCCTGGTGTCCTTGTCATGCTTCACAGGATCAATGACTATGTCGCGGAGATTCTTGAGGTCTCCAACTTGACATTT
GCCTTCAAAGGCCCATGGTTCTCTGGAATGAACATGTTGATCACTGCAGATCCTTCA Coding sequence: (SEQ ID NO: 38)
MAYVGLVEVFIALLVFFFFHFLIHKKSHQITPRNWPVLGMLPGVLVMLHRINDYVAEILEVSNLTFAFKGPWFSGMNMLITADPSNIQHVFSSNFSNYD
KGPEFKEMFDFLGNGIFTADSKLWEDMRKSALVVLSHQGFQSFSLRTITCKIKNGLVPVLDHFAEANTVFDLQDVFQRLAFDVTLTLVTGCDSSSLSIE
MPKNEYAKAMDDAEEVVVYRHVKPVVLWKLQNWIGLGEEKKMKEANAAFDRSCAKYISAKREEIISHHSNIGGEAHAEDLLSVYMNLDISKYELLNPND
DNFLKDIIKSFMLAGRDAIATTLTWFFWLLSKNPEAVTKIRQEINTNLPGSGMSLDADKLNKMVYLHGALCESLRLYAPIPFERKTPIKQDVLPSGHMV
DKNWKILFSVYALGRMRSVWGQDASEFKPERWISERNGGLKHEPSFKFFVFNSGPRNCLGKNLSFLQMKTVAVEIIRNYDIKVVEGHKIEPASSIILHM
KHGLKVTVSKRGLVS*

Promoter Candidate ID: 15295994

Modulates the gene as identified by its GI number: 18418018

The GenBank description of the gene: putative protein; protein id: At4g32460.1, supported by cDNA: 37529. [*Arabidopsis thaliana*] >gi|21593257|gb|AAM65206.1| unknown [*Arabidopsis thaliana*]

The promoter sequence: (SEQ ID NO: 39)
ttttcgaaaatttaaataatgattcgatcaacacttttttctcattttatcaaacccctttgattgaatagaccgctaaaacaatttgcttgattggtct
ttcttacaacgactaagttacaaatgtgactgaaagttaccgatcaaacccatgaaaaaaacttgagcccatataccttgctatggatttggcacacag
accaagctttcgaagcaactgtttggttgattcggaattgttttctgataataaata The Ceres cDNA ID of the endogenous coding sequence to the promoter: 12371508 cDNA nucleotide sequence: (nucleotides 1–255 of SEQ ID NO: 40)
ATTCCACTCCCACTAAACATTCCTTCTCTCGCTCACTCTTCTCCAATCCTTATTTTATTTTTTGAAAGTTTAAAATTTTATACAACATATCAATTTGGG
GTAGAAAAATTCGAAAGAAATGAAAGAGATGGGAGTGATAGTGCTTCTTCCTTCACTCGTTCTTCTACGTTGCCTTTTGCTTCAATGATGGACTACT
ACCAAACGGTGACTTCGAACTCGGTCCACGACATTCGGACATGAAAGGAACACAAGT Coding sequence: (SEQ ID NO: 41)
MKEMGVIVLLLLHSFFYVAFCFNDGLLPNGDFELGPRHSDMKGTQVINITAIPNWELSGFVEYIPSGHKQGDMILVVPKGAFAVRLGNEASIKQKISVK
KGSYYSITFSAARTCAQDERLNVSVAPHHAVMPIQTVYSSSGWDLYSWAFKAQSDYADIVIHNPGVEEDPACGPLIDGVAMRALFPPRPTNKNILKNGG
FEEGPWVLPNISSGVLIPPNSIDDHSPLPGWMVESLKAVKYIDSDHFSVPQGRRAVELVAGKESAVAQVVRTIPGKTYVLSFSVGDASNACAGSMIVEA
FAGKDTIKVPYESKGKGGFKRSSLRFVAVSSRTRVMFYSTFYAMRNDDFSSLCGPVIDDVKLLSARRP*

Promoter Candidate ID: 15296000

Modulates the gene as identified by its GI number: 15234651

The GenBank description of the gene: hypothetical protein; protein id: At4g30180.1 [*Arabidopsis thaliana*] >gi|7486762|pir||T14078 hypothetical protein F9N11.30 - *Arabidopsis thaliana* >gi|5730128| mb|CAB52462.1| hypothetical hypothetical protein [*Arabidopsis thaliana*]

The promoter sequence: (SEQ ID NO: 42)
cgtcatattagttacagtggcagtaaaattcagtttcaaagatgtttgtcttgatatgttgtacagatcaccaattgaactaccactaataataactaa
atttctgtttagcaagttaccatctgtatccaaatatcgcaaaagtagtgggtagtgaaacccaaattcatcacacatgcagcataaaaaaaaagaagg
tcaaatggtatatataatatgagggagatctatattaagataatatgggtagaaatg The Ceres cDNA ID of the endogenous coding sequence to the promoter: 12656661 cDNA nucleotide sequence: (SEQ ID NO: 43)
ATGGAGAGGCAAATCATAAACAGGAAGAAACGAGTGTTTTCTCTTGAACCAAACAAGAACCCTAGTGCAGTTTTCACGAGAAAATACACAAGCCACTTG
GTTCCTGCACTCAAGAAGCTCAACATGAACAAGAACTCTTCAAAACAAACCGTGAAGCATGAAGTAGATATGGCTTTGGCTTTGTCTGCTCAAGAATTT
GCATGGAGCCGTTTCTTGCTGCAGAAGCTATCGTCCTCATCGAATCCAACCACTACCACTAGTTCTTCTTCCGATGGAATTCGGATTCTTGAAAGACCC
GATAAAGAAGGCGGAAACGAAGAAGGAGGGATAGAGGAGAGACTGAGGGAATTGAAGAAGCTTTTGCCAGGTGGGGAAGAGATGAATGTGGAAGAAATG
TTGAGTGAGATTGGTAACTACATTAAATGTCTTGAGTTGCAGACGATTGCTCTCAAGTCCATTGTTCAAGATAGTACTTGA Coding sequence: (SEQ ID NO: 44)
MERQIINRKKRVFSLEPNKNPSAVFTRKYTSHLVPALKKLNMNKNSSKQTVKHEVDMALALSAQEFAWSRFLLQKLSSSNPTTTTSSSSDGIRILERP
DKEGGNEEGGIEERLRELKKLLPGGEEMNVEEMLSEIGNYIKCLELQTIALKSIVQDST*

TABLE 1-continued

Promoter Reports for Results of Shade Cloth Procedure

Promoter Candidate ID: 15296003

Modulates the gene as identified by its GI number: 18403306

The GenBank description of the gene: Expressed protein; protein id: At3g22231.1, supported by cDNA: gi_14335055 [Arabidopsis thaliana] >gi|14335056|gb|AAK59792.1| AT3g22240/MMP21_1 [Arabidopsis thaliana] >gi|27363330|gb|AAO11584.1| At3g22240/MMP21_1 [Arabidopsis thaliana]

The promoter sequence: (SEQ ID NO: 45)
acagatcacaccaacataaggaacaaagccaaaactattaatcatggttcaaaggcagttggttaatcactttttcattttcatgaaatgttaaattaa
ttaatcatcaaaagaggttatttaatttacatagagtttagagcaataccccaaaaaaaaaaaaagaggttctaaaagacagttccaggaacaaaataa
ttcaaatttgttaaattcctcatgttttacgacgtcatgtacgtgtacgtcatgtacgtgacgaaagccatttctgcaacaaaccatttctcactttca
tctcaaccataggtatcgctttcctctgcccttgtgcatttcaaacaatatcatttgctttatctctgcaattatatatgtgttggatataaccaaaaa
acctagacctaccacttcgctaaggtaggtctgtccgtgagttgtctgtgattagatgttttattgttcaatattgactcttctttcttttatataatg
aataatgtaaaaaatttcctaatatttgtctaccttataaattagaagcacaacactctctcctcttcacaaatctcacatcctcactcctcagctcct
caaatcaga The Ceres cDNA ID of the endogenous coding sequence to the promoter: 12730017 cDNA nucleotide sequence: (SEQ ID NO: 46)
ACAAATCTCACATCCTCACTCCTCAGCTCCTCAAATCAGAATGAATCAATCCGCGCAAAATTACTTTTCCGTGCAAAAACCTTCAGAGACTTCATCAGG
GCCGTACACAAGTCCGCCACCAATTGGTTATCCGACTAGAGATGCGGTGGTGGGTGATCCTCCGGCAGCAGCAGTGGAGACAAACTCCAAGGGCGTCAA
CCCCGAAGCCATAATGAGTTGTTTTAGTACTTGTATGGAGTGTATCTTCTGCTGCGGCTATGCTCCAGCCTCTGTACATCAGAGTAAATCAGCATGAT
GAGACAGAAGTCGTTGCCCAAACCTGAAAAACAACACGTGATAGAAAATCTATATATATATATATATATATATATATGTTATAGTAGTCGTTTCTATGGAT
TTCCACGCATTTTAAAGTTTATTTGTTTCACTGTTTAAAATGAATCATTTGCTTCGTGTATTTTGTTTCTATAT Coding sequence: (SEQ ID NO: 47)
MNQSAQNYFSVQKPSETSSGPYTSPPPIGYPTRDAVVGDPPAAAVETNSKGVNPEAIMSCFSTCMECIFCCGVCSSLCTSE*

Promoter Candidate ID: 15296006

Modulates the gene as identified by its GI number: 7487010

The GenBank description of the gene: hypothetical protein T14P8.2 - Arabidopsis thaliana >gi|3193289| gb|AAC19273.1| similar to several small proteins (~100 aa) that are induced by heat, auxin, ethylene and wounding such as Phaseolus aureus indole-3-acetic acid induced protein ARG The promoter sequence: (SEQ ID NO: 48)
atcttgacatgcttaaacacattttataattcgaacctcactttgcctactttacacacgtctacttatagtagatgagcatcaatcattgaaccgttc
gtataatacaatttttttttttgtaatacgttataattagaaagtaatggaaaataagttgaaacacaaattttcaacggttttactaagatttaatttt
tacaattttcaaaatataaccgaattatttaaatcgtattaaatttataattaattttt The Ceres cDNA ID of the endogenous coding sequence to the promoter: 12339689 cDNA nucleotide sequence: (SEQ ID NO: 49)
TCATCTCTTCAAACCATTTTCGAAAGCCTTGAGAGAGAGAACACAGACGATACCAACTTTCTTCAATCTCGTTGCCGCAGTATAATTATCTCATTCCTC
GGATATATCTCTCCTTCTGCGGCGGCGACAAGAAGCTACAAGAATAAAAAGTCTGTTTTCTCTCTTTTCAAGAAACCACTTACTTCGAAAATGGCTCGT
TCTATCTCTAACGTTAAGATCGTATCTGCTTTCGTCTCTCGTGAACTCTCCAATGCTATCTTCCGACGTGGTTATGCGGCCACGGCGGCGCAAGGGAGC
GTTTCGAGCGGTGGAAGAAGTGGAGCTGTTGCTTCGGCTGTGATGAAGAAGAAGGGAGTGGAAGAATCAACCCAGAAGATTTCTTGGGTTCCAGATCCC
AAAACCGGTTATTACAGACCCGAAACCGGTTCCAACGAGATTGACGCGGCTGAGCTACGAGCAGCTCTCTTGAACAACAAGCAGTGATTGATTATTATT
ACATGTAATTTTGTCAAGGTCTTTAAGAGGAGATTAGTGGGTAATGATCTGGTGCAGTGAACCCTATTTTCATATGTTAAGTGCGGTTCTGTAATGAAT
AAAATAGAGAAGCGTTTGGTTTCCTCTAATTGTAACAAAAGGATCGTTGGATGTATGATAGAGTTTTTCTTATAAAACCATTTCAGAACTT Coding sequence: (SEQ ID NO: 50)
MARSISNVKIVSAFVSRELSNAIFRRGYAATAAQGSVSSGGRSGAVASAVMKKKGVEESTQKISWVPDPKTGYYRPETGSNEIDAAELRAALLNNKQ*

Promoter Candidate ID: 15296009

Modulates the gene as identified by its GI number: 18423445

The GenBank description of the gene: expressed protein [Arabidopsis thaliana] >gi|28973707|gb| AAO64170.1| unknown protein [Arabidopsis thaliana] >gi|29824227|gb|AAP04074.1| unknown protein [Arabidopsis thaliana]

The promoter sequence: (SEQ ID NO: 51)
caacaaacattcccttggagatttgagagattcatatcattaaatgcacttctcaatatacggagtattactaattaaaaccttatttcgagttctctc
aaacgtaacccatgcaaaaatggcccccagagataagactttgatgagtctccacgtcactttctgatttcggcttttgtccctaatctttcgacaac
attcgtctcgcaccccgacatttcccgggacctctgtctctccccctctctttctcct The Ceres cDNA ID of the endogenous coding sequence to the promoter: 13578669 cDNA nucleotide sequence: (SEQ ID NO: 93)
TTGTTTTGTCTCAAACAAATTTCTCTGCACACACTCAACAACATATCCCATAACAAAAAAAAAGCTATTAAAAAAAAAGAGAAGCAGCCATGGAAGAAGG
TAAGCAAGAAGCTTCAATGCCACTAGTTCCAATTGACAGCTTCTCTTACAGTTGGTTAGTTAACTTTCCTTCTTTAGAAGCTACCATTGATGATCATCA
TCAAACATACGAAGATTCATCTTCTTCTTCTTCCTTCATTGAGATGGATCCAAGATT TABLE 1-continued Promoter Reports for Results of Shade Cloth Procedure Coding sequence: (SEQ ID NO: 54)
MEEGKQEASMPLVPIDSFSYSWLVNFPSLEATIDDHHQTYEDSSSSSSFIEMDPRLPPSRRFFIKTSHESSFKFDNFVSFSDEDHSLVHADELFRDGYV
MPYRLKPTSAATEEESEPLDTTTSEKIDTRGLNSKPSPTSSRKLRRVSKWVLLKYLDFLTPLCKRLRRCRSAVTTGSIGMDSRIRVTTSCRSRVYSDEM
TSSPRISVADDYYWRRSCDSESSIYEAVLHCKKSFEK*

TABLE 2

Promoter Reports for Results of Far Red Induction Experiments

Promoter Expression Report #152
Promoter Tested In: *Arabidopsis thaliana*, Wassilewskija (WS) ecotype
Spatial expression summary:
Flower          H stomata
Silique         H stomata
Rosette Leaf    H stomata H stipule
Primary Root    L epidermis L trichoblast H cortex L root hairs
Observed expression pattern:
T1 mature: Guard cell expression throughout inflorescence apex and carpels in early
flower buds.
T2 seedling: GFP expression specific within cortex cells overlaying lateral root
primordia and root hair producing epidermal cells.
Expected expression pattern:   Petiole
Selection Criteria:            Mutant lines
Gene: product = "tetratricopeptide repeat (TPR)-containing note = "contains Pfam
profile PF00515 TPR Domain; go function: protein binding [goid 0005515]"
GenBank: NM_129819 tetratricopeptide repeat (TPR)-containing protein (At2g42580) mRNA
Source Promoter Organism:   *Arabidopsis thaliana*, Columbia (Col) ecotype
Vector:                     pNewbin4-HAP1-GFP
Marker Type:                GFP-ER
Generation Screened:    X T1 Mature  X T2 Seedling  ↑T2 Mature  ↑T3 Seedling
Inductions completed.

| Treatment: | Age: | Gen: | Time points: | Events Screened/Response | Response: |
|---|---|---|---|---|---|
| 1. Drought | 4 wks | T2 | 8 days no water | 2/0 | No |
| 2. Far red | 7 days | T2 | 1 Hr | 2/0 | No |
| Far Red$_{730}$ = 525 μW/cm$^2$ | | | 4 Hr | 2/0 | No |
| | | | 24 Hr | 2/0 | No |

Inducible expression summary:
Treatment:         Time point induced:         Organs induced:         Tissues induced:
T1 Mature Plant Expression      Organs/Tissues screened
Events Screened:       n = 6        Events Expressing:   n = 2
GFP Expression
X Flower            ↑pedicel ↑receptacle ↑nectary ↑sepal ↑petal ↑filament ↑anther ↑pollen
                    ↑carpel ↑style ↑papillae ↑vascular ↑epidermis H stomata ↑trichome
                    ↑silique
X Silique           ↑stigma ↑style ↑carpel ↑septum ↑placentae ↑transmitting tissue ↑vascular
                    ↑epidermis H stomata ↑abscission zone ↑ovule
   ↑ Ovule          Pre-fertilization: ↑primordia ↑inner integument ↑outer integument ↑embryo
                    sac ↑funiculus ↑chalaza ↑micropyle ↑gametophyte
                    Post-fertilization: ↑zygote ↑suspensor ↑ embryo sack ↑inner integument
                    ↑outer integument ↑endothelium ↑seed coat ↑primordia ↑chalaza
                    ↑micropyle ↑early endosperm ↑mature endosperm ↑embryo
   ↑ Embryo         ↑suspensor ↑preglobular ↑globular ↑heart ↑torpedo ↑late ↑mature
                    ↑provascular ↑hypophysis ↑radicle ↑cotyledons ↑hypocotyl
↑ Stem              ↑epidermis ↑cortex ↑vascular ↑xylem ↑phloem ↑pith ↑stomata ↑trichome
↑ Leaf              ↑petiole ↑mesophyll ↑vascular ↑epidermis ↑trichome ↑primordia ↑stomata
                    ↑stipule ↑margin
↑ Shoot apical meristem   ↑shoot apical meristem ↑flower primordium
X Guard cells (Gc) in Flower Bud, Pedicle and Silique
T2 Seedling Expression     Tissues Screened
Events Screened: n = 2           Events Expressing: n = 2
Seedlings expressing/Seedlings screened
Event-01: 5/6
Event-02: 4/6
↑ Scheduled
GFP Expression Detected
↑ Hypocotyl         ↑epidermis ↑cortex ↑vascular ↑xylem ↑phloem ↑stomata
↑ Cotyledon         ↑mesophyll ↑vascular ↑epidermis ↑margin ↑stomata
                    ↑hydathode
X Rosette Leaf      ↑mesophyll ↑vascular ↑epidermis ↑trichome ↑petiole
                    ↑primordia H stomata H stipule ↑margin ↑hydathode
X Primary Root      L epidermis L trichoblast ↑atrichoblast H cortex ↑endodermis
                    ↑vascular ↑xylem ↑phloem ↑pericycle ↑quiescent
                    ↑columella ↑root cap L root hairs

TABLE 2-continued

Promoter Reports for Results of Far Red Induction Experiments

↑ Lateral root              ↑epidermis ↑trichoblast ↑atrichoblast ↑cortex ↑endodermis
                                  ↑initials ↑flanking cells ↑vascular ↑lateral root cap
↑ Shoot apical meristem    ↑Shoot apical meristem
X Cortex (Cr) in root transition zone, lateral root, and lateral root initial
X Epidermis (Ep) in lateral root, and root
X Guard cell (Gc) in seedling, rosette leaf
X Lateral root (Lr) in lateral root, lateral root initial
X Root hair (Rh) in root
X Stipules (Ss) in seedling,
Promoter utility
Trait Area:           Water use efficiency, nutrients
Sub-trait Area:      Heat, drought, water potential, moisture stress at seed set, moisture
                        stress during seed fill, low nitrogen tolerance, nitrogen use efficiency
Utility:              Among other uses this promoter sequence could be useful to improve:
Notes:
Construct:           PT0590
Promoter candidate I.D:    11768848
cDNA I.D:           12639140 (OCKHAM3-CD)
Lines expressing:      PT0590-03, -04 Jan. 16, 2004

(A) Predicted promoter sequence (1000 bp).

```
5' CCAGTCGA▼TTGGCCCGAT▼CGGCC NNNNNNNNNNNNNN GGCCTGCA▼GGGCCAGTCGCA▼CTGG 3'          (SEQ ID NO: 2)

>152.PT0590 predicted                                                              (SEQ ID NO: 55)
attattcaatttaataaaaattgagtcggccaatttaatgcgagacttctgtacaacgacccktaaaagtgggtttgat aaatgaaacatattgcaacaaaaaaatactagtaataatgataaaatagtaacatgtcgtggcgcattgaatatccta cgaaggtttagtgttttacttttaaaaaatcctaatatgatactagtacatatagctagcttgccttgcttatgctatt gcatagtctgtattaataaatgatgttatacatttcgatagagtaacattttgggaacatgagtgaacgtgcttgaat cttcgtgccttgacgtcagaagctagtaattttaaatactaattaacattcatacaaattaacagatacaatgtact atatcataattcgtttccgtaacacaacgcaacaatttgaaagtagatgtactttagtacttagttagtgtgcaccaa aaaaaaagatgtagttagttagtaaggggttaaatgttttaatttattaagaaaacttaaattcattaaatgttaga aaaagtctaattagtttatattcgaacactgtgctcaaaattaaaaagtcaactattttagactatagagtttattaa ttaataataaattcgataaatcaccgtattattttcttcaacgacaagtagccgtgaagacacgggagcgaagagaga taaacagaagatgaagaagaagatcaatgtcataatcttcagggagataaatccgtaatctttattaatcaaggttaa tccttttttttttcttcatcttaattctttgcgtcttccttttctatttatcacgagatctgtctttcttttcctct tctttctctctcttctctctgaagacagtacttgtttctgtccggcgttaaaagcttcggtggtggtctcttgacttc tctgagaagaagaaaaggaagctgagtctcatttttagattcagctcacgaggaagtgacgacga
```

(B) Sequence verification and confirmation.

```
>152.PT0590 experimental                                                           (SEQ ID NO: 94)
tcgattggcccgatcggccattattcaatttaataaaaattgagtcggccaatttaatgcgagacttctgtacaacgaccct aaaagtgggtttgataaatgaaacatattgcaacaaaaaaatactagtaataatgataaaatagtaacatgtcatggcgcat tgaatatcctacgaaggtttagtgtttacttttaaaaaatcctaatatgatactagtacatatagctagcttgccttgctta tgctattgcatagtctgtattaataaatgatgttatacatttcgatagagtaacattttgggaacatgagtgaacgtgcttg aatcttcgtgccttgacgtcagaagctagtaattttaaatactaattaacattcatacaaattaacagatacaatgtacta tatcataattcgtttccgtaacacaacgcaacaatttgaaagtagatgtactttagtacttagttagtgtgcaccaaaaaa aagatgtagttagttagtaaggggttaaatgttttaatttattaagaaaacttaaattcattaaatgttagaaaaagtctaa ttagtttatattcgaacactgtgctcaaaattaaaaagtcaactattttagactatagagtttattaattaataataaattc
```

-continued

```
gataaatcaccgtattattttcttcaacgacaagtagccgtgaagacacgggagcgaagagagataaacagaagatgaagaa gaagatcaatgtcataatcttcagggagataaatccgtaatctttattaatcaaggttaatcctttttttttcttcatctt aattctttgcgtcttccttttctatttatcacgagatctgtctttcttttcctcttctttctctctcttctctctgaagac agtacttgtttctgtccggcgttaaaagcttcggtggtggtctcttgacttctctgagaagaagaaaaggaagctgagtctc attttagattcagctcacgaggaagtgacgacgaggcctgcagggccagtgcactgggatccaacaatgtcctccgactcgt ccaagatcaagaggaagcggaaccgcatcccg
```

| Sequence (bp) | Mismatch | Predicted/Experimental |
|---|---|---|
| 138 | Ecotype variant | g/a |
| Sequence Q.C. notes: | | |

(C) Predicted vs. Experimental sequence alignment.

Score = 1902 bits (989), Expect = 0.0
Identities = 999/1000 (99%), Gaps = 1/1000 (0%)
Query = Predicted (SEQ ID NO: 55)
Subject = Experimental (nucleotides 20–1018 of SEQ ID NO: 94)

```
Query:   1   attattcaatttaataaaaattgagtcggccaatttaatgcgagacttctgtacaacgac   60
             ||||||||||||||||||||||||||||||||||||||||||||||||||||||||||||
Sbjct:   1   attattcaatttaataaaaattgagtcggccaatttaatgcgagacttctgtacaacgac   60

Query:  61   cctaaaagtgggtttgataaatgaaacatattgcaacaaaaaaatactagtaataatgat   120
             ||||||||||||||||||||||||||||||||||||||||||||||||||||||||||||
Sbjct:  61   cctaaaagtgggtttgataaatgaaacatattgcaacaaaaaaatactagtaataatgat   120

Query: 121   aaaatagtaacatgtcgtggcgcattgaatatcctacgaaggtttagtgtttacttttaa   180
             ||||||||||||||||||||| ||||||||||||||||||||||||||||||||||||||
Sbjct: 121   aaaatagtaacatgtcatggcgcattgaatatcctacgaaggtttagtgtttacttttaa   180

Query: 181   aaaatcctaatatgatactagtacatatagctagcttgccttgcttatgctattgcatag   240
             ||||||||||||||||||||||||||||||||||||||||||||||||||||||||||||
Sbjct: 181   aaaatcctaatatgatactagtacatatagctagcttgccttgcttatgctattgcatag   240

Query: 241   tctgtattaataaatgatgttatacatttcgatagagtaacattttgggaacatgagtga   300
             ||||||||||||||||||||||||||||||||||||||||||||||||||||||||||||
Sbjct: 241   tctgtattaataaatgatgttatacatttcgatagagtaacattttgggaacatgagtga   300

Query: 301   acgtgcttgaatcttcgtgcccttgacgtcagaagctagtaattttaaatactaattaac   360
             ||||||||||||||||||||||||||||||||||||||||||||||||||||||||||||
Sbjct: 301   acgtgcttgaatcttcgtgcccttgacgtcagaagctagtaattttaaatactaattaac   360

Query: 361   attcatacaaattaacagatacaatgtactatatcataattcgtttccgtaacacaacgc   420
             ||||||||||||||||||||||||||||||||||||||||||||||||||||||||||||
Sbjct: 361   attcatacaaattaacagatacaatgtactatatcataattcgtttccgtaacacaacgc   420

Query: 421   aacaatttgaaagtagatgtactttagtacttagttagtgtgcaccaaaaaaaaagatg   480
             ||||||||||||||||||||||||||||||||||||||||||||||||||||||||||||
Sbjct: 421   aacaatttgaaagtagatgtactttagtacttagttagtgtgcaccaaaaaaaaagatg   480

Query: 481   tagttagttagtaaggggttaaatgttttaatttattaagaaaacttaaattcattaaat   540
             ||||||||||||||||||||||||||||||||||||||||||||||||||||||||||||
Sbjct: 480   tagttagttagtaaggggttaaatgttttaatttattaagaaaacttaaattcattaaat   540

Query: 541   gttagaaaaagtctaattagtttatattcgaacactgtgctcaaaattaaaaagtcaact   600
             ||||||||||||||||||||||||||||||||||||||||||||||||||||||||||||
Sbjct: 540   gttagaaaaagtctaattagtttatattcgaacactgtgctcaaaattaaaaagtcaact   600

Query: 601   attttagactatagagtttattaattaataataaattcgataaatcaccgtattattttc   660
             ||||||||||||||||||||||||||||||||||||||||||||||||||||||||||||
Sbjct: 600   attttagactatagagtttattaattaataataaattcgataaatcaccgtattattttc   660
```

```
Query:  661  ttcaacgacaagtagccgtgaagacacgggagcgaagagagataaacagaagatgaagaa  720
             ||||||||||||||||||||||||||||||||||||||||||||||||||||||||||||
Sbjct:  660  ttcaacgacaagtagccgtgaagacacgggagcgaagagagataaacagaagatgaagaa  720

Query:  721  gaagatcaatgtcataatcttcagggagatataatccgtaatctttattaatcaaggttaa  780
             ||||||||||||||||||||||||||||||||||||||||||||||||||||||||||||
Sbjct:  720  gaagatcaatgtcataatcttcagggagataaatccgtaatctttattaatcaaggttaa  780

Query:  781  tccttttttttttcttcatcttaattctttgcgtcttccttttctatttatcacgagatc  840
             ||||||||||||||||||||||||||||||||||||||||||||||||||||||||||||
Sbjct:  780  tccttttttttttcttcatcttaattctttgcgtcttccttttctatttatcacgagatc  840

Query:  841  tgtctttcttttcctcttctttctctctcttctctctgaagacagtacttgtttctgtc  900
             ||||||||||||||||||||||||||||||||||||||||||||||||||||||||||||
Sbjct:  840  tgtctttcttttcctcttctttctctctcttctctctgaagacagtacttgtttctgtc  900

Query:  901  cggcgttaaaagcttcggtggtggtctcttgacttctctgagaagaagaaaaggaagctg  960
             ||||||||||||||||||||||||||||||||||||||||||||||||||||||||||||
Sbjct:  900  cggcgttaaaagcttcggtggtggtctcttgacttctctgagaagaagaaaaggaagctg  960

Query:  961  agtctcattttagattcagctcacgaggaagtgacgacga  1000
             ||||||||||||||||||||||||||||||||||||||||
Sbjct:  960  agtctcattttagattcagctcacgaggaagtgacgacga  1000
```

| Promoter Expression Report #171 |
| --- |

Promoter Tested In: *Arabidopsis thaliana*, Wassilewskija (WS) ecotype
Spatial expression summary:
Ovule　　　　　　　Post-fertilization: H suspensor H inner integument L mature endosperm
Embryo　　　H suspensor
Hypocotyl　　　　　H vascular
Cotyledon　　　　　L hydathode
Primary Root　H vascular
Observed expression pattern:
T1 mature: GFP expressed in endothelium cell layer of maturing ovules and in depleted endosperm cells of maturing seed. No expression observed in endosperm of developing ovules.
T2 seedling: High GFP expression throughout vasculature of root and hypocotyl. Weak GFP expression in hydathodes of cotyledons.
Expected expression pattern:　　　Shade Induced
Selection Criteria:　　　　　　　Microarray
Gene:　　　　　　　　　　　　　Auxin-responsive AUX/IAA family protein
GenBank: NM_119380 *Arabidopsis thaliana* auxin-responsive AUX/IAA family protein (At4g32280) mRNA, complete cds gi |30689330|ref|NM_119380.2|[30689330]
Source Promoter Organism:　　　*Arabidopsis thaliana*, Columbia (Col) ecotype
Vector:　　　　　　　　　　　　pNewbin4-HAP1-GFP
Marker Type:　　　　　　　　　GFP-ER
Generation Screened:　　XT1 Mature XT2 Seedling ↑T2 Mature ↑T3 Seedling
Inductions completed.

|  |  |  |  | Events Screened/ |  |
| --- | --- | --- | --- | --- | --- |
| Treatment: | Age: | Gen: | Time points: | Response | Response: |
| 1. Far red | 7 days | T2 | 1 Hr | 2/0 | No |
| Far Red$_{730}$ = 525 μW/cm$^2$ |  |  | 24 Hr | 2/0 | No |

Inducible expression summary:
Treatment:　　　Time point induced:　　　Organs induced:　　　Tissues induced:
1. Far red　　　No differences observed.
Far Red$_{730}$ = 525 μW/cm$^2$
T1 Mature Plant Expression  Organs/Tissues screened
Events Screened:　　n = 2　　Events Expressing:　　n = 2
GFP Expression Detected
↑ Flower　　　　　　↑pedicel ↑receptacle ↑nectary ↑sepal ↑petal ↑filament ↑anther ↑pollen
　　　　　　　　　　↑carpel ↑style ↑papillae ↑vascular ↑epidermis ↑stomata ↑trichome
　　　　　　　　　　↑silique
↑ Silique　　　　　　↑stigma ↑style ↑carpel ↑septum ↑placentae ↑transmitting tissue ↑vascular
　　　　　　　　　　↑epidermis ↑stomata ↑abscission zone ↑ovule
　X Ovule　　　　　Pre-fertilization: ↑primordia ↑inner integument ↑outer integument ↑embryo
　　　　　　　　　　sac ↑funiculus ↑chalaza ↑micropyle ↑gametophyte
　　　　　　　　　　Post-fertilization: ↑zygote H suspensor ↑embryo sack H inner integument
　　　　　　　　　　↑outer integument ↑endothelium ↑seed coat ↑primordia ↑chalaza
　　　　　　　　　　↑micropyle ↑early endosperm L mature endosperm ↑embryo
　↑ Embryo　　　　　H suspensor ↑preglobular ↑globular ↑heart ↑torpedo ↑late ↑mature
　　　　　　　　　　↑provascular ↑hypophysis ↑radicle ↑cotyledons ↑hypocotyl
↑ Stem　　　　　　　↑epidermis ↑cortex ↑vascular ↑xylem ↑phloem ↑pith ↑stomata ↑trichome

| Promoter Expression Report #171 | |
|---|---|
| ↑ Leaf | ↑petiole ↑mesophyll ↑vascular ↑epidermis ↑trichome ↑primordia ↑stomata ↑stipule ↑margin |
| ↑ Shoot apical meristem | ↑shoot apical meristem ↑flower primordium |
| X Endosperm (En) in the ovule, developing seed coat, mature ovule/early seed | |
| X Endothelium (Ed) in the ovule, developing seed coat, and mature ovule/early seed | |
| X Seed coat (Sc) in the developing seed coat | |
| X Suspensor (Su) in the mature ovule/early seed | |
| T2 Seedling Expression | Tissues Screened |
| Events Screened: n = 2 | Events Expressing: n = 2 |
| Seedlings expressing/Seedlings screened | |
| Event 01: 2(4) | |
| Event 02: 5(6) | |
| GFP Expression Detected | |
| X Hypocotyl | ↑epidermis ↑cortex H vascular ↑xylem ↑phloem ↑stomata |
| X Cotyledon | ↑mesophyll ↑vascular ↑epidermis ↑margin ↑stomata L hydathode |
| ↑ Rosette Leaf | ↑mesophyll ↑vascular ↑epidermis ↑trichome ↑petiole ↑primordia ↑stomata ↑stipule ↑margin ↑hydathode |
| X Primary Root | ↑epidermis ↑trichoblast ↑atrichoblast ↑cortex ↑endodermis H vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Hydathode (Hd) in the cotyledon | |
| X Vascular (Vs) in the cotyledon, and root | |
| Induction Screens | |
| 1. Far red | No differences observed. Images not shown. |
| Far Red$_{730}$ = 525 µW/cm$^2$ | |
| Promoter utility | |
| Trait Area: | PG&D, nutrients |
| Sub-trait Area: | Nitrogen use efficiency, yield, seed size |
| Nominated By: | Shing Kwok |
| Investigators: | Medrano, L., Theiss, N. |
| Utility: | Among other uses this promoter sequence could be useful to modulate seed size and nitrogen use efficiency. |
| Construct: | PT0672 |
| Promoter candidate I.D: | 15295940 |
| cDNA I.D: | 23523314, 12655184 (OCKHAM3-CD) |
| Lines expressing: | PT0672-01, -02 |

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3'  (SEQ ID NO: 2)

>171.PT0672 predicted  (SEQ ID NO: 58)

cagccgtaaatccttccataaatttattttgcaagttttgctcattatataatgagcggaatttatgatataatcgtt tgtaataatgttatgttttgatcaaaatttgaaattaaaagtaggtgagaacttgttatacagtgtagataaggtgga tcttgaatataaaaataaaatttataagatgtatttaaagcagaaaagcataaaactttagataaaataatgtaaaaa tgtgttagcatcaatgtttgggatattggccgacccgaacttaatcaatgtcggaagccattacttctctcccaaaaga ccttttccttcggagaactaggaacttcctcactacctttcgcttaacgtgaaagccataaatttcatatattcata aaaatcagaaaatctaaaactgtttagtatcacctgttttggtatagactattggttttgtgttacttcctaaacta tatgatttcgtacttcattggatcttatagagatgaatattcgtaaaagataagttatctggtgaaacgttacttca gtcatgtttgggtctagatttacatactactatgaaacattttaagataataattatcctagccaactatatgttctat attatgggccaagaagatatagaactaaaagttcagaatttaacgatataaattactagtatattctaatacttgaat gattactgttttagttgtttagaataaatagtagcgtgttggttaagataccatctatccacatctatatttgtgtgg gttacataaaatgtacataatattatatacatatatatgtatattttttgataaagccatatattactccttgacctct gcccccatttccttttactataaataggaatactcatgatcctctaattcagcaatcaacaccaacgaacacaacctt ttccaaagccaataataaaagaacaaaagcttttagtttcatcaaagacgaagctgccttagaa (B) Sequence verification.

>171.PT0672 experimental (SEQ ID NO: 59)
cagccgtaaatcctccataaatttattttgcaagttttgctcattatata
atgagcggaatttatgatataatcgtttgtaataatgttatgttttgatc
aaaatttgaaattaaaagtaggtgagaacttgttatacagtgtagataag
gtggatcttgaatataaaaataaaatttataagatgtatttaaagcagaa
aagcataaaactttagataaaataatgtaaaaatgtgttagcatcaatgt
tgggatattggccgacccgaacttaatcaatgtcggaagccattacttct
ctcccaaaagaccttttccttcggagaactaggaacttcctcactacct
ttcgcttaacgtgaaagccataaatttcatatattcataaaaatcagaaa
atctaaaactgtttagtatcacctgttttggtatagactattggttttg
tgttacttcctaaactatatgatttcgtacttcattggatcttatagaga
tgaatattcgtaaaaagataagttatctggtgaaacgttacttcagtcat
gttgggtctagatttacatactactatgaaacattttaagataataatta -continued
tcctagccaactatatgttctatattatgggccaagaagatatagaacta
aaagttcagaatttaacgatataaattactagtatattctaatacttgaa
tgattactgttttagttgtttagaataaatagtagcgtgttggttaagat
accatctatccacatctatatttgtgtgggttacataaaatgtacataat
attatatacatatatatgtatattttgataaagccatatattactcctt
gacctctgcccccatttccttttactataaataggaatactcatgatcct
ctaattcagcaatcaacaccaacgaacacaaccttttccaaagccaataa
taaaagaacaaaagcttttagtttcatcaaagacgaagctgccttagaa

| Predicted Position (bp) | Mismatch | Predicted/Experimental |
|---|---|---|
| 15 | SNP | t/— |
| Sequence Q.C.: | | |

(C) Predicted vs. Experimental sequence alignment.

Query = Predicted (SEQ ID NO: 58)
Subject = Experimental (SEQ ID NO: 59)
Score = 1894 bits (985), Expect = 0.0
Identities = 999/1001 (99%), Gaps = 2/1001 (0%)
Strand = Plus/Plus

```
Query: 1   cagccgtaaatccttccataaatttattttgcaagttttgctcattatataatgagcgga 60
           |||||||||||||| |||||||||||||||||||||||||||||||||||||||||||||
Sbjct: 1   cagccgtaaatcct-ccataaatttattttgcaagttttgctcattatataatgagcgga 59

Query: 61  atttatgatataatcgtttgtaataatgttatgttttgatcaaaatttgaaattaaaagt 120
           ||||||||||||||||||||||||||||||||||||||||||||||||||||||||||||
Sbjct: 60  atttatgatataatcgtttgtaataatgttatgttttgatcaaaatttgaaattaaaagt 119

Query: 121 aggtgagaacttgttatacagtgtagataaggtggatcttgaatataaaaataaaattta 180
           ||||||||||||||||||||||||||||||||||||||||||||||||||||||||||||
Sbjct: 120 aggtgagaacttgttatacagtgtagataaggtggatcttgaatataaaaataaaattta 179

Query: 181 taagatgtatttaaagcagaaaagcataaaactttagataaaataatgtaaaaatgtgtt 240
           ||||||||||||||||||||||||||||||||||||||||||||||||||||||||||||
Sbjct: 180 taagatgtatttaaagcagaaaagcataaaactttagataaaataatgtaaaaatgtgtt 239

Query: 241 agcatcaatgttgggatattggccgacccgaacttaatcaatgtcggaagccattacttc 300
           ||||||||||||||||||||||||||||||||||||||||||||||||||||||||||||
Sbjct: 240 agcatcaatgttgggatattggccgacccgaacttaatcaatgtcggaagccattacttc 299

Query: 301 tctcccaaaagaccttttccttcggagaactaggaacttcctcactacctttcgcttaa 360
           ||||||||||||||||||||||||||||||||||||||||||||||||||||||||||||
Sbjct: 300 tctcccaaaagaccttttccttcggagaactaggaacttcctcactacctttcgcttaa 359

Query: 361 cgtgaaagccataaatttcatatattcataaaaatcagaaaatctaaaactgtttagtat 420
           ||||||||||||||||||||||||||||||||||||||||||||||||||||||||||||
Sbjct: 360 cgtgaaagccataaatttcatatattcataaaaatcagaaaatctaaaactgtttagtat 419

Query: 421 cacctgttttggtatagactattggttttgtgttacttcctaaactatatgatttcgta 480
           ||||||||||||||||||||||||||||||||||||||||||||||||||||||||||||
Sbjct: 420 cacctgttttggtatagactattggttttgtgttacttcctaaactatatgatttcgta 479

Query: 481 cttcattggatcttatagagatgaatattcgtaaaaagataagttatctggtgaaacgtt 540
           ||||||||||||||||||||||||||||||||||||||||||||||||||||||||||||
Sbjct: 480 cttcattggatcttatagagatgaatattcgtaaaaagataagttatctggtgaaacgtt 539

Query: 541 acttcagtcatgttgggtctagatttacatactactatgaaacattttaagataataatt 600
           ||||||||||||||||||||||||||||||||||||||||||||||||||||||||||||
Sbjct: 540 acttcagtcatgttgggtctagatttacatactactatgaaacattttaagataataatt 599
```

-continued

```
Query: 601  atcctagccaactatatgttctatattatgggccaagaagatatagaactaaaagttcag 660
            ||||||||||||||||||||||||||||||||||||||||||||||||||||||||||||
Sbjct: 600  atcctagccaactatatgttctatattatgggccaagaagatatagaactaaaagttcag 659

Query: 661  aatttaacgatataaattactagtatattctaatacttgaatgattactgttttagttgt 720
            ||||||||||||||||||||||||||||||||||||||||||||||||||||||||||||
Sbjct: 660  aatttaacgatataaattactagtatattctaatacttgaatgattactgttttagttgt 719

Query: 721  ttagaataaatagtagcgtgttggttaagataccatctatccacatctatatttgtgtgg 780
            ||||||||||||||||||||||||||||||||||||||||||||||||||||||||||||
Sbjct: 720  ttagaataaatagtagcgtgttggttaagataccatctatccacatctatatttgtgtgg 799

Query: 781  gttacataaaatgtacataatattatatacatatatatgtatattttgataaagccata 840
            ||||||||||||||||||||||||||||||||||||||||||||||||||||||||||||
Sbjct: 780  gttacataaaatgtacataatattatatacatatatatgtatattttgataaagccata 839

Query: 841  tattactccttgacctctgccccatttccttttactataaataggaatactcatgatcc 900
            ||||||||||||||||||||||||||||||||||||||||||||||||||||||||||||
Sbjct: 840  tattactccttgacctctgccccatttccttttactataaataggaatactcatgatcc 899

Query: 901  tctaattcagcaatcaacaccaacgaacacaaccttttccaaagccaata-ataaaagaa 959
            |||||||||||||||||||||||||||||||||||||||||||||||||| |||||||||
Sbjct: 900  tctaattcagcaatcaacaccaacgaacacaaccttttccaaagccaatanataaaagaa 959

Query: 960  caaaagctttagtttcatcaaagacgaagctgccttagaa 1000
            ||||||||||||||||||||||||||||||||||||||||
Sbjct: 960  caaaagctttagtttcatcaaagacgaagctgccttagaa 1000
```

---

Promoter Expression Report # 175

Promoter Tested In: *Arabidopsis thaliana*, Wassilewskija (WS) ecotype
Spatial expression summary:
Ovule            L chalaza
Leaf             L vascular
Cotyledon        L epidermis
Primary Root     H vascular
Observed expression pattern:
T1 mature: GFP expressed in vascular tissues of leaf and in funiculus-ovule connective site.
T2 seedling: GFP expression in root vascular tissue.
Expected expression pattern:       Shade induced
Selection Criteria:                Microarray
Gene:                              hypothetical protein
GenBank: NM_119287 *Arabidopsis thaliana* hypothetical protein (At4g31380) mRNA, complete cds gi| 18417796|ref|NM_119287.1|[18417796]
Source Promoter Organism:          *Arabidopsis thaliana*, Columbia (Col) ecotype
Vector:                            pNewbin4-HAP1-GFP
Marker Type:                       GFP-ER
Generation Screened:   XT1 Mature XT2 Seedling ↑T2 Mature ↑T3 Seedling
Inductions completed.

| Treatment: | Age: | Gen: | Time points: | Events Screened/ Response | Response: |
|---|---|---|---|---|---|
| 1. Far Red | 7 days | T2 | 1 Hr | 2/1 | Yes |
| Far Red$_{730}$ = 525 μW/cm$^2$ | | | 24 Hr | 2/0 | No |
| 2. Far Red | 7 days | T2 | 1 Hr | 3/0 | No |
| Far Red$_{730}$ = 525 μW/cm$^2$ | | | 24 Hr | 3/0 | No |

Inducible expression summary:

| Treatment: | Time point induced: | Organs induced: | Tissues induced: |
|---|---|---|---|
| 1. Far Red | 1 Hr | Rosette leaf | Epidermal |
| 2. Far Red | No response observed. | | |

T1 Mature Plant Expression Organs/Tissues screened
Events Screened:   n = 5    Events Expressing:   n = 2
GFP Expression Detected
↑ Flower         ↑pedicel ↑receptacle ↑nectary ↑sepal ↑petal ↑filament ↑anther ↑pollen
                 ↑carpel ↑style ↑papillae ↑vascular ↑epidermis ↑stomata ↑trichome
                 ↑silique
↑ Silique        ↑stigma ↑style ↑carpel ↑septum ↑placentae ↑transmitting tissue ↑vascular
                 ↑epidermis ↑stomata ↑abscission zone ↑ovule
   X Ovule       Pre-fertilization: ↑primordia ↑inner integument ↑outer integument ↑embryo
                 sac ↑funiculus ↑chalaza ↑micropyle ↑gametophyte
                 Post-fertilization: ↑zygote ↑suspensor ↑ embryo sack ↑inner integument
                 ↑outer integument ↑endothelium ↑seed coat ↑primordia L chalaza
                 ↑micropyle ↑early endosperm ↑mature endosperm ↑embryo
   ↑ Embryo      ↑suspensor ↑preglobular ↑globular ↑heart ↑torpedo ↑late ↑mature
                 ↑provascular ↑hypophysis ↑radicle ↑cotyledons ↑hypocotyl -continued

| Promoter Expression Report # 175 |  |
|---|---|
| ↑ Stem | ↑epidermis ↑cortex ↑vascular ↑xylem ↑phloem ↑pith ↑stomata ↑trichome |
| X Leaf | ↑petiole ↑mesophyll L vascular ↑epidermis ↑trichome ↑primordia ↑stomata ↑stipule ↑margin |
| ↑ Shoot apical meristem | ↑ Shoot apical meristem ↑ Flower primordium |
| X Chalaza (Ch) in the ovule | |
| X Funiculus (Fn) in the ovule | |
| X Micropyle (Mp) in the ovule | |
| X Vascular (Vs) in the leaf | |
| T2 Seedling Expression | Tissues Screened |
| Events Screened: n = 2 | Events Expressing: n = 2 |
| Seedlings expressing/Seedlings screened | |
| Event-03: 2(6) | |
| Event-05: 3(6) | |
| GFP Expression Detected | |
| ↑ Hypocotyl | ↑epidermis ↑cortex ↑vascular ↑xylem ↑phloem ↑stomata |
| X Cotyledon | ↑mesophyll ↑vascular L epidermis ↑margin ↑stomata ↑hydathode |
| ↑ Rosette Leaf | ↑mesophyll ↑vascular ↑epidermis ↑trichome ↑petiole ↑primordia ↑stomata ↑stipule ↑margin ↑hydathode |
| X Primary Root | ↑epidermis ↑trichoblast ↑atrichoblast ↑cortex ↑endodermis H vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑Shoot apical meristem |
| X Epidermis (Ep) in the colyledon | |
| X Hypocotyl (Hy) in the root | |
| X Vascular (Vs) in the root | |
| Promoter utility | |
| Trait Area: | PG&D, source |
| Sub-trait Area: | Seed size, low light tolerence, increased germination |
| Nominated By: | Shing Kwok |
| Investigators: | Medrano, L., Theiss, N. |
| Utility: | Among other uses this promoter sequence could be useful to modulate seed size and shade avoidance |
| Notes: 1) There is one knock-out allele in the Salk collection for this locus. | |
| Construct: | PT0673 |
| Promoter candidate I.D: | 15295943 |
| cDNA I.D: | 23416553, 13618832 |
| Lines expressing: | PT0673-03, -05 |

(A) Predicted promoter sequence (1000 bp).

5' CCAGTCGA▼TTGGCCCGAT▼CGGCC NNNNNNNNNNNNNN GGCCTGCA▼GGGCCAGTCA▼CTGG 3'  (SEQ ID NO: 2)

>175.PT0673 predicted  (SEQ ID NO: 60)
tgttttcatttttttttcatttcgttactactaacagaacttttcatttatatcttgaaattttgttgtataactca
aataaagattgaaactaacatgatgatacttgtaattatctgattatttccttccatgtaaaccgatcaacatctagt
cgtaaaacagaaaacaaaaaagacactgatcgacactcatagcataacaaccgatcttagtatacatatgtgtgatat
gttacgtcatatttagctcatgcaaactagaatttcttgccgtatttcagttccatatatctcggatatgcatatcaa
atttacgacaagaatctaaattttgtgaaatattaccaaagattcctttatatatagaaaagagataaattaaccaca
caaacataataaaatggaaaagaagaagagattcgaaaatgtggacccattttttaaaaattctaacattcaaactg
aataaatttcccacgctaattttgatttatttatctccttgcatatcggaataagtataacattcttcaaagaccaaa
aaaagaagaaagtataatattctttcaatcaatttccatagaaaagatatggcatttcaattacgtcccaaatatgac
gatcgaaatcatcttatataactcaaagtatttaactacatatagtttcgaatcagaaaaatagctttggttttacgg
attttgagttatgctcttgtgtcaaaatatgataaataaattgttggtagattgatagataagattcttccttttcga
aaattctggaattctgcatttaatatatatatatatcatataatataatgataatctacttgtcagtctacacacc
cctttaccaacatatatatatatatagcacacactctacacggtttccttatcctcatcaaaattaacaaactcat
ttttgaatacccaaaaaaaaacctagctagctcgaatttttttaaatatataataacatcaaca (B) Sequence verification.

(SEQ ID NO: 61)
>175.PT0673 experimental
tgtttttcattttttttcatttcgttactactaacagaacttttcattt
atatcttgaaattttgttgtataactcaaataaagattgaaactaacatg
atgatacttgtaattatctgattatttccttccatgtaaaccgatcaaca
tccagtcgtaaaacagaaaacaaaaaagacactgatcgacactcatagca
taacaaccgatcttagtatacatatgtgtgatatgttacgtcatatttag
ctcatgcaaactagaatttcttgccgtatttcagttccatatatctcgga
tatgcatatcaaatttacgacaagaatctaaattttgtgaaatattacca
aagattcctttatatatagaaaagagataaattaaccacacaaacataat
aaaatggaaaaagaagaagagattcgaaaatgtggacccattttttaaaa
attctaacattcaaactgaataaatttcccacgctaattttgatttattt
atctccttgcatatcggaataagtataacattcttcaaagaccaaaaaaa
gaagaaagtataatattctttcaatcaatttccatagaaaagatatggca -continued
tttcaattacgtcccaaatatgacgatcgaaatcatcttatataactcaa
agtatttaactacatatagtttcgaatcagaaaaatagctttggttttac
ggattttgagttatgctcttgtgtcaaaatatgataaataaattgttggt
agattgatagataagattcttccttttcgaaaattctggaattctgcatt
taatatatatatatatcatataatataatgataatctacttgtcagtc
tacacacccctttaccaacatatatatatatatagcacacactctaca
cggtttccttatcctcatcaaaattaacaaactcattttttgaatacccaa
aaaaaaacctagctagctcgaatttttttaaatatataataacatcaaca

| Predicted Position (bp) | Mismatch | Predicted/Experimental |
|---|---|---|
| 153 | SNP | t/c |

Sequence Q.C.:

(C) Predicted vs. Experimental sequence alignment.

```
(Query: SEQ ID NO: 60)
(Subject: SEQ ID NO: 61)
Score = 1917 bits (997), Expect = 0.0
Identities = 999/1000 (99%)
Strand = Plus/Plus Query: 1    tgtttttcattttttttcatttcgttactactaacagaacttttcatttatatcttgaa 60
            ||||||||||||||||||||||||||||||||||||||||||||||||||||||||||||
Sbjct: 1    tgtttttcattttttttcatttcgttactactaacagaacttttcatttatatcttgaa 60

Query: 61   attttgttgtataactcaaataaagattgaaactaacatgatgatacttgtaattatctg 120
            ||||||||||||||||||||||||||||||||||||||||||||||||||||||||||||
Sbjct: 61   attttgttgtataactcaaataaagattgaaactaacatgatgatacttgtaattatctg 120

Query: 121  attatttccttccatgtaaaccgatcaacatcagtcgtaaaacagaaaacaaaaaagac 180
            ||||||||||||||||||||||||||||||||||||||||||||||||||||||||||||
Sbjct: 121  attatttccttccatgtaaaccgatcaacatccagtcgtaaaacagaaaacaaaaaagac 180

Query: 181  actgatcgacactcatagcataacaaccgatcttagtatacatatgtgtgatatgttacg 240
            ||||||||||||||||||||||||||||||||||||||||||||||||||||||||||||
Sbjct: 181  actgatcgacactcatagcataacaaccgatcttagtatacatatgtgtgatatgttacg 240

Query: 241  tcatatttagctcatgcaaactagaatttcttgccgtatttcagttccatatatctcgga 300
            ||||||||||||||||||||||||||||||||||||||||||||||||||||||||||||
Sbjct: 241  tcatatttagctcatgcaaactagaatttcttgccgtatttcagttccatatatctcgga 300

Query: 301  tatgcatatcaaatttacgacaagaatctaaattttgtgaaatattaccaaagattcctt 360
            ||||||||||||||||||||||||||||||||||||||||||||||||||||||||||||
Sbjct: 301  tatgcatatcaaatttacgacaagaatctaaattttgtgaaatattaccaaagattcctt 360

Query: 361  tatatatagaaaagagataaattaaccacacaaacataataaaatggaaaaagaagaaga 420
            ||||||||||||||||||||||||||||||||||||||||||||||||||||||||||||
Sbjct: 361  tatatatagaaaagagataaattaaccacacaaacataataaaatggaaaaagaagaaga 420

Query: 421  gattcgaaaatgtggacccattttttaaaaattctaacattcaaactgaataaatttccc 480
            ||||||||||||||||||||||||||||||||||||||||||||||||||||||||||||
Sbjct: 421  gattcgaaaatgtggacccattttttaaaaattctaacattcaaactgaataaatttccc 480

Query: 481  acgctaattttgatttatttatctccttgcatatcggaataagtataacattcttcaaag 540
            ||||||||||||||||||||||||||||||||||||||||||||||||||||||||||||
Sbjct: 481  acgctaattttgatttatttatctccttgcatatcggaataagtataacattcttcaaag 540

Query: 541  accaaaaaaagaagaaagtataatattctttcaatcaatttccatagaaaagatatggca 600
            ||||||||||||||||||||||||||||||||||||||||||||||||||||||||||||
Sbjct: 541  accaaaaaaagaagaaagtataatattctttcaatcaatttccatagaaaagatatggca 600
```

```
-continued

Query: 601 tttcaattacgtcccaaatatgacgatcgaaatcatcttatataactcaaagtatttaac 660
            ||||||||||||||||||||||||||||||||||||||||||||||||||||||||||||
Sbjct: 601 tttcaattacgtcccaaatatgacgatcgaaatcatcttatataactcaaagtatttaac 660

Query: 661 tacatatagtttcgaatcagaaaaatagctttggttttacggattttgagttatgctctt 720
            ||||||||||||||||||||||||||||||||||||||||||||||||||||||||||||
Sbjct: 661 tacatatagtttcgaatcagaaaaatagctttggtttttacggattttgagttatgctctt 720

Query: 721 gtgtcaaaatatgataaataaattgttggtagattgatagataagattcttccttttcga 780
            ||||||||||||||||||||||||||||||||||||||||||||||||||||||||||||
Sbjct: 721 gtgtcaaaatatgataaataaattgttggtagattgatagataagattcttccttttcga 780

Query: 781 aaattctggaattctgcatttaatatatatatatatcatataatataatgataatcta 840
            ||||||||||||||||||||||||||||||||||||||||||||||||||||||||||||
Sbjct: 781 aaattctggaattctgcatttaatatatatatatatcatataatataatgataatcta 840

Query: 841 cttgtcagtctacacacccctttaccaacatatatatatatatagcacacactctaca 900
            ||||||||||||||||||||||||||||||||||||||||||||||||||||||||||||
Sbjct: 841 cttgtcagtctacacacccctttaccaacatatatatatatatagcacacactctaca 900

Query: 901 cggtttccttatcctcatcaaaattaacaaactcattttgaatacccaaaaaaaacct 960
            ||||||||||||||||||||||||||||||||||||||||||||||||||||||||||||
Sbjct: 901 cggtttccttatcctcatcaaaattaacaaactcattttgaatacccaaaaaaaacct 960

Query: 961 agctagctcgaatttttaaatatataataacatcaaca 1000
            ||||||||||||||||||||||||||||||||||||||
Sbjct: 961 agctagctcgaatttttaaatatataataacatcaaca 1000
```

| Promoter Expression Report #176 |
| --- |

Promoter Tested In: *Arabidopsis thaliana*, Wassilewskija (WS) ecotype
Spatial expression summary:
Flower             H pedicel H sepal H petal H filament M carpel M style H epidermis M silique
Silique            M style M carpel H epidermis L ovule
Ovule              Post-fertilization: L outer integument
Embryo             M heart M torpedo M late
Stem               H vascular H pith
Hypocotyl          H epidermis
Cotyledon          H epidermis
Rosette Leaf       M epidermis
Primary Root       M epidermis   L root hairs
Lateral root       M epidermis
Observed expression pattern:
T1 mature: GFP expressed throughout mature plant. In the flower, GFP is first expressed in young buds
at the pedicles and sepals, later in the mature flower, GFP expression extends to the sepals, petals,
and silique. GFP is not expressed in the anthers or stigma. High GFP expression is observed in heart
stage through mature embryos. Weak expression in outer integument of some ovules. High GFP
expression throughout vascular and pith regions of stem.
T2 seedling: High GFP expression throughout epidermal cells of seedling. No expression in root caps
or guard cells.
Expected expression pattern:       Shade Induced
Selection Criteria:                Microarray
Gene:                              allergen V5/Tpx-1-related family protein
GenBank: NM_126057 *Arabidopsis thaliana* allergen V5/Tpx-1-related family protein (At5g66590)
mRNA, complete cds gi|30698237|ref|NM_126057.2|[30698237]
Source Promoter Organism:          *Arabidopsis thaliana*, Columbia ecotype
Vector:                            pNewbin4-HAP1-GFP
Marker Type:                       GFP-ER
Generation Screened:     XT1 Mature XT2 Seedling ↑T2 Mature ↑T3 Seedling
Inductions completed.

|  |  |  |  | Events Screened/ |  |
| --- | --- | --- | --- | --- | --- |
| Treatment: | Age: | Gen: | Time points: | Response | Response: |
| 1. Far red | 7 days | T2 | 1 Hr | 5/0 | No |
| Far Red$_{730}$ = 525 µW/cm$^2$ |  |  | 24 Hr | 5/0 | No |

Inducible expression summary:
Treatment:        Time point induced:        Organs induced:        Tissues induced:
1. Far red        1 Hr, 24 Hr                               No differences observed.
T1 Mature Plant Expression Organs/Tissues screened
Events Screened:    n = 6      Events Expressing:    n = 5
GFP Expression Detected
X Flower           H pedicel ↑receptacle ↑nectary H sepal H petal H filament ↑anther ↑pollen
                   M carpel M style ↑papillae ↑vascular H epidermis ↑stomata ↑trichome
                   M silique
X Silique          ↑stigma M style M carpel ↑septum ↑placentae ↑transmitting tissue
                   ↑vascular H epidermis ↑stomata ↑abscission zone L ovule

| Promoter Expression Report #176 |  |
|---|---|
| X Ovule | Pre-fertilization: ↑primordia ↑inner integument ↑outer integument ↑embryo sac ↑funiculus ↑chalaza ↑micropyle ↑gametophyte<br>Post-fertilization: ↑zygote ↑suspensor ↑ embryo sack ↑inner integument L outer integument ↑endothelium ↑seed coat ↑primordia ↑chalaza ↑micropyle ↑early endosperm ↑mature endosperm ↑embryo |
| X Embryo | ↑suspensor ↑preglobular ↑globular M heart M torpedo M late ↑mature ↑provascular ↑hypophysis ↑radicle ↑cotyledons |
| X Stem | ↑epidermis ↑cortex H vascular ↑xylem ↑phloem H pith ↑stomata ↑trichome |
| ↑ Leaf | ↑petiole ↑mesophyll ↑vascular ↑epidermis ↑trichome ↑primordia ↑stomata ↑stipule ↑margin |
| ↑ Shoot apical meristem | ↑shoot apical meristem ↑flower primordium |
| X Anther (An) in the mature flower | |
| X Carpel (Ca) in the silique and mature ovule | |
| X Embryo (Em) in the mature ovule | |
| X Filament (Fi) in the mature flower | |
| X Petal (Pe) in the mature flower | |
| X Pith (Pi) in the stem | |
| X Sepal (Se) in the developing flower | |
| X Silique (Si) in the developing flower | |
| X Ovules (Ov) in the mature ovule | |
| X Vascular bundle (Vb) in the stem | |
| T2 Seedling Expression | Tissues Screened |
| Events Screened: n = 2 | Events Expressing: n = 2 |
| Seedlings expressing/Seedlings screened | |
| Event-01: 4(6) | |
| Event-02: 5(6) | |
| GFP Expression Detected | |
| X Hypocotyl | H epidermis ↑ cortex ↑vascular ↑xylem ↑phloem ↑stomata |
| X Cotyledon | ↑mesophyll ↑vascular H epidermis ↑margin ↑stomata ↑hydathode |
| X Rosette Leaf | ↑mesophyll ↑vascular M epidermis ↑trichome ↑petiole ↑primordia ↑stomata ↑stipule ↑margin ↑hydathode |
| X Primary Root | M epidermis ↑trichoblast ↑atrichoblast ↑ cortex ↑endodermis ↑vascular ↑xylem ↑phloem ↑pericycle ↑quiescent ↑columella ↑root cap L root hairs |
| X Lateral root | M epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Epidermis (Ep) in the cotyledon and roots | |
| X Guard cells (Gc) in the cotyledon | |
| X Hypocotyl (Hy) in the seedling and cotyledon | |
| X Rosette leaf (Rl) in the seedling | |
| X Root hair (Rh) in the roots | |
| Promoter utility | |
| Trait Area: | PG&D, nutrients, cold |
| Sub-trait Area: | Seed size, nitrogen use efficiency, cold tolerance |
| Utility: | Among other uses this promoter sequence could be useful to modulate seed size, nitrogen use efficiency, and cold tolerance in seedlings. Nitrogen inducible expression in broad range of tissues can be useful for improving tolerance to low nitrogen. |
| Construct: | PT0681 |
| Promoter candidate I.D: | 15295979 |
| cDNA I.D: | 23541268 (12688858) |
| Lines expressing: | PT0681-01, -03, -04, -05, -06 |

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3' (SEQ ID NO: 2)

>176.PT0681 predicted (SEQ ID NO: 62)
gactttttttttatggagaacaaattatccagtagatgttttttttattgctcagtaattgagaaatgggcacgagg atgaagatattccattgatgtgattccaatcttaataacattgcaatttcgtagctatataaatcatttcatgtgtaa tattatccatcttgttaaattttctaatctctaaaatttcataccgtttgtgtttaacatagtttccgatccaatcca atccagcaaagtgaaataatttcgaatgataaggctgttttgcaaaatgccaaatatggcggaacaattttatttaa gaaacaagataaggattattaatgatcagatatgcttgatgaagttgtggtccattcttacttctcttctgcatattt atcacatcggtttctcattatctctatgcattcgggactactaatacaacaatagcacaaaaatacaacgtgacaaca aaaacaaccgagtagaaaactataaagacaacaacatttcaaattctctgttgccactaatactgaaaatccatttaa -continued

```
attttcttttttgtgggttgaatttgcaccatataaaaatccaataatacaaaagaaagcaaatatacatgattggata
ttcttcgattatgatgtcgaacaacaacaattattaacatgtgtatagtttggcaaaaaatgaatatgaggtaaagag
ggctggacccattggccctataagcattaatgggcctgaaagcaacaacagaaattggaattaaataacgttgggtat
ctgtctgtcacatgcaacacagacaacttgagaatggatcaatcaacattcacgtgccatgatcctctcttcctctta
ttttgtctccttccaccaatcccatatctttctctattatacatctctaattatctcacttttaacatatagtttttt
tatacatctttaatgactatataaaccaaacactgatcttttcaggttgcgaataaaccaaga
```

(B) Sequence verification.

(SEQ ID NO: 63)
>176.PT0681 experimental
```
gacttttttttatggagaacaaattatccagtagatgttttttttttatt
gctcagtaattgagaaatgggcacgaggatgaagatattccattgatgtg
attccaatcttaataacattgcaatttcgtagctatataaatcatttcat
gtgtaatattatccatcttgttaaattttctaatctctaaaatttcatac
cgtttgtgtttaacatagtttccgatccaatccaatccagcaaagtgaaa
taatttcgaatgataaggctgttttgcaaaatgccaaatatggcggaaca
attttttatttaagaaacaagataaggattattaatgatcagatatgcttg
atgaagttgtggtccattcttacttctcttctgcatatttatcacatcgg
tttctcattatctctatgcattcgggactactaatacaacaatagcacaa
aaatacaacgtgacaacaaaaacaaccgagtagaaaactataaagacaac
aacatttcaaattctctgttgccactaatactgaaaatccatttaaatttt
tcttttgtgggttgaatttgcaccatataaaaatccaataatacaaaag
```

-continued
```
aaagcaaatatacatgattggatattcttcgattatgatgtcgaacaaca
acaattattaacatgtgtatagtttggcaaaaaatgaatatgaggtaaag
agggctggacccattggccctataagcattaatgggcctgaaagcaacaa
cagaaattggaattaaataacgttgggtatctgtctgtcacatgcaacac
agacaacttgagaatggatcaatcaacattcacgtgccatgatcctctct
tcctcttattttgtctccttccaccaatcccatatctttctctattatac
atctctaattatctcacttttaacatatagtttttttatacatctttaat
gactatataaaccaaacactgatcttttcaggttgcgaataaaccaaga
```

| Predicted Position (bp) | Mismatch | Predicted/Experimental |
|---|---|---|
| 1–1000 Sequence Q.C. | None | |

(C) Predicted vs. Experimental sequence alignment.

---

Score = 1923 bits (1000), Expect = 0.0
Identities = 1000/1000 (100%)
Strand = Plus/Plus
Query = Predicted (SEQ ID NO: 62)
Subject = Experimental (SEQ ID NO: 63)

```
Query:  1   gacttttttttatggagaacaaattatccagtagatgttttttttttattgctcagtaat  60
            ||||||||||||||||||||||||||||||||||||||||||||||||||||||||||||
Sbjct:  1   gacttttttttatggagaacaaattatccagtagatgttttttttttattgctcagtaat  60

Query: 61   tgagaaatgggcacgaggatgaagatattccattgatgtgattccaatcttaataacatt  120
            ||||||||||||||||||||||||||||||||||||||||||||||||||||||||||||
Sbjct: 61   tgagaaatgggcacgaggatgaagatattccattgatgtgattccaatcttaataacatt  120

Query: 121  gcaatttcgtagctatataaatcatttcatgtgtaatattatccatcttgttaaattttc  180
            ||||||||||||||||||||||||||||||||||||||||||||||||||||||||||||
Sbjct: 121  gcaatttcgtagctatataaatcatttcatgtgtaatattatccatcttgttaaattttc  180

Query: 181  taatctctaaaatttcataccgtttgtgtttaacatagtttccgatccaatccaatccag  240
            ||||||||||||||||||||||||||||||||||||||||||||||||||||||||||||
Sbjct: 181  taatctctaaaatttcataccgtttgtgtttaacatagtttccgatccaatccaatccag  240

Query: 241  caaagtgaaataatttcgaatgataaggctgttttgcaaaatgccaaatatggcggaaca  300
            ||||||||||||||||||||||||||||||||||||||||||||||||||||||||||||
Sbjct: 241  caaagtgaaataatttcgaatgataaggctgttttgcaaaatgccaaatatggcggaaca  300
```

-continued

```
Query:  301  attttttatttaagaaacaagataaggattattaatgatcagatatgcttgatgaagttgt  360
             ||||||||||||||||||||||||||||||||||||||||||||||||||||||||||||
Sbjct:  301  attttttatttaagaaacaagataaggattattaatgatcagatatgcttgatgaagttgt  360

Query:  361  ggtccattcttacttctcttctgcatatttatcacatcggtttctcattatctctatgca  420
             ||||||||||||||||||||||||||||||||||||||||||||||||||||||||||||
Sbjct:  361  ggtccattcttacttctcttctgcatatttatcacatcggtttctcattatctctatgca  420

Query:  421  ttcgggactactaatacaacaatagcacaaaaatacaacgtgacaacaaaaacaaccgag  480
             ||||||||||||||||||||||||||||||||||||||||||||||||||||||||||||
Sbjct:  421  ttcgggactactaatacaacaatagcacaaaaatacaacgtgacaacaaaaacaaccgag  480

Query:  481  tagaaaactataaagacaacaacatttcaaattctctgttgccactaatactgaaaatcc  540
             ||||||||||||||||||||||||||||||||||||||||||||||||||||||||||||
Sbjct:  481  tagaaaactataaagacaacaacatttcaaattctctgttgccactaatactgaaaatcc  540

Query:  541  atttaaattttcttttgtgggttgaatttgcaccatataaaaatccaataatacaaaag   600
             ||||||||||||||||||||||||||||||||||||||||||||||||||||||||||||
Sbjct:  541  atttaaattttcttttgtgggttgaatttgcaccatataaaaatccaataatacaaaag   600

Query:  601  aaagcaaatatacatgattggatattcttcgattatgatgtcgaacaacaacaattatta  660
             ||||||||||||||||||||||||||||||||||||||||||||||||||||||||||||
Sbjct:  601  aaagcaaatatacatgattggatattcttcgattatgatgtcgaacaacaacaattatta  660

Query:  661  acatgtgtatagtttggcaaaaaatgaatatgaggtaaagagggctggacccattggccc  720
             ||||||||||||||||||||||||||||||||||||||||||||||||||||||||||||
Sbjct:  661  acatgtgtatagtttggcaaaaaatgaatatgaggtaaagagggctggacccattggccc  720

Query:  721  tataagcattaatgggcctgaaagcaacaacagaaattggaattaaataacgttgggtat  780
             ||||||||||||||||||||||||||||||||||||||||||||||||||||||||||||
Sbjct:  721  tataagcattaatgggcctgaaagcaacaacagaaattggaattaaataacgttgggtat  780

Query:  781  ctgtctgtcacatgcaacacagacaacttgagaatggatcaatcaacattcacgtgccat  840
             ||||||||||||||||||||||||||||||||||||||||||||||||||||||||||||
Sbjct:  781  ctgtctgtcacatgcaacacagacaacttgagaatggatcaatcaacattcacgtgccat  840

Query:  841  gatcctctcttcctcttattttgtctccttccaccaatcccatatctttctctattatac  900
             ||||||||||||||||||||||||||||||||||||||||||||||||||||||||||||
Sbjct:  841  gatcctctcttcctcttattttgtctccttccaccaatcccatatctttctctattatac  900

Query:  901  atctctaattatctcacttttaacatatagttttttttatacatctttaatgactatataa  960
             ||||||||||||||||||||||||||||||||||||||||||||||||||||||||||||
Sbjct:  901  atctctaattatctcacttttaacatatagttttttttatacatctttaatgactatataa  960

Query:  961  accaaacactgatctttttcaggttgcgaataaaccaaga  1000
             ||||||||||||||||||||||||||||||||||||||||
Sbjct:  961  accaaacactgatctttttcaggttgcgaataaaccaaga  1000
```

---

Promoter Expression Report #177

Promoter Tested In: *Arabidopsis thaliana*, Wassilewskija (WS) ecotype
Spatial expression summary:
Flower          H pedicel H petal M filament M anther H epidermis H carpel
Silique         H carpel H epidermis
Stem            L endodermis H pith
Rosette Leaf    L epidermis H trichome H petiole
Observed expression pattern:
T1 mature: Vegetatative expression. GFP expressed in epidermis of stem and pedicels of the inflorescence meristem near the shoot apex. In the Flower, GFP expression is specific to stamen and carpels of siliques. GFP highly expressed in parenchyma cells of stem. No expression in ovules. T2 seedling: High specific GFP expression in cells at the base of developing trichomes and petioles of rosette leaves. Expression in adventitious trichome cells of the hypocotyls.
Expected expression pattern:    Shade Induced
Selection Criteria:             Ceres expression data
Gene:                           expressed protein; "/product = "unknown protein"
GenBank: NM_113862 expressed protein (At3g29370) mRNA, complete
Source Promoter Organism:       *Arabidopsis thaliana*, Columbia ecotype -continued

| Promoter Expression Report #177 | |
|---|---|
| Vector: | pNewbin4-HAP1-GFP |
| Marker Type: | GFP-ER |
| Generation Screened: | XT1 Mature XT2 Seedling ↑T2 Mature ↑T3 Seedling |

Inductions completed.

| Treatment: | Age: | Gen: | Time points: | Events Screened/ Response | Response: |
|---|---|---|---|---|---|
| 1. Far red | 7 days | T2 | 1 Hr | 2/0 | No |
| Far Red$_{730}$ = 525 µW/cm$^2$ | | | 24 Hr | 2/1 | Yes |

Inducible expression summary:

| Treatment: | Time point induced: | Organs induced: | Tissues induced: |
|---|---|---|---|
| 1. Far red Far Red$_{730}$ = 525 µW/cm$^2$ | 24 Hr | Petiole | Epidermis, Cortex, Vascular |

T1 Mature Plant Expression Organs/Tissues screened
Events Screened:  n = 6    Events Expressing:    n = 2
GFP Expression Detected

| X Flower | H pedicel ↑receptacle ↑nectary ↑sepal H petal M filament M anther ↑pollen H carpel ↑style ↑papillae ↑vascular H epidermis ↑stomata ↑trichome ↑silique |
|---|---|
| X Silique | ↑stigma ↑style H carpel ↑septum ↑placentae ↑transmitting tissue ↑vascular H epidermis ↑stomata ↑abscission zone ↑ovule |
| ↑ Ovule | Pre-fertilization: ↑primordia ↑inner integument ↑outer integument ↑embryo sac ↑funiculus ↑chalaza ↑micropyle ↑gametophyte Post-fertilization: ↑zygote ↑suspensor ↑ embryo sack ↑funiculus ↑inner integument ↑outer integument ↑endothelium ↑seed coat ↑primordia ↑chalaza ↑micropyle ↑early endosperm ↑mature endosperm ↑embryo |
| ↑ Embryo | ↑suspensor ↑preglobular ↑globular ↑heart ↑torpedo ↑late ↑mature ↑provascular ↑hypophysis ↑radicle ↑cotyledons ↑hypocotyl |
| X Stem | ↑ epidermis ↑cortex L endodermis ↑ vascular ↑xylem ↑phloem H pith ↑stomata ↑trichome |
| ↑ Leaf | ↑petiole ↑mesophyll ↑vascular ↑epidermis ↑trichome ↑primordia ↑stomata ↑stipule ↑margin |
| ↑ Shoot apical meristem | ↑ Shoot apical meristem ↑ Flower primordium |

X Stem (Sm) in the inflorescence meristem
X Silique (Si) in the flower and silique
X Stamen (St) in the flower
X Ovule/Ovary (Ov) in the silique and ovary
X Pedicles (Pd) in the inflorescence meristem
X Pith (Pi) in the stem
T2 Seedling Expression    Tissues Screened
Events Screened: n = 2    Events Expressing: n = 2
Seedlings expressing/Seedlings screened
Event-01: 4(6)
Event-05: 3(6)
↑ No GFP Expression Detected

| ↑ Hypocotyl | ↑epidermis ↑cortex ↑vascular ↑xylem ↑phloem ↑stomata |
|---|---|
| ↑ Cotyledon | ↑mesophyll ↑vascular ↑epidermis ↑margin ↑stomata ↑hydathode |
| X Rosette Leaf | ↑mesophyll ↑vascular L epidermis H trichome H petiole ↑primordia ↑stomata ↑stipule ↑margin ↑hydathode |
| ↑ Primary Root | ↑epidermis ↑trichoblast ↑atrichoblast ↑cortex ↑endodermis ↑vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑Shoot apical meristem |

X Epidermis (Ep) in the cotyledon
X Trichiomes (Tc) in the rosette leaf
X Petiole (Pt) in the seedling
Promoter utility
Trait Area:
Sub-trait Area:
Utility: Among other uses this promoter sequence could be useful to
improve: Modulation of flower and inflorescence structure, especially
numbers of flowers per inflorescence and therefore seeds per
inflorescence. Modulation of carpel symmetry and number of
valves per carpel and number of seeds per carpel. Modulation of shade
avoidance responses, especially petiole and leaf elongation under
shade. Enhanced seedling and plant performance under shade
conditions. Combinational effects or growth, development, fertility and
responses to shade.
Notes:

| Construct: | PT0684 |
|---|---|
| Promoter candidate I.D: | 15295997 |
| cDNA I.D: | 13486695 |
| Lines expressing: | PT0684-01-05; Apr. 26, 2004 |

(A) Predicted promoter sequence (1000 bp).

(SEQ ID NO: 64)
5' CCAGTCGA▼TTGGCCCGAT▼CGGCC-tagctagatttctatataaac agaagaaagttaaaaagcaaataaaaattcacaaatagaaatcgaacaaa aagctatgaaaatataaataccataaccttatggaaaaacgatgaaatgc ttaacaaaaaaactttggcaatggcatgcatgtgcctgtaacagaaggc ccccataagctgttagtgatatacaacttaagcaaatgtgcactcttcac gcacttcccgcttttctaaatttcaatttatttgtctacattttttgtcca aattattgatataattctaccacgacttcccccacatgtccctccaaaga gatccgtactacacagtctaccgacagcacatgcatggatttttccaaacc atcttctttaaggataatccttgacattttttaatattaaaaaaataacaa aaaattcaatatataaataacatcctaaatctatgttttggtagaaaaca agttctaaagttcacatttggacagtggttagtacttggtaatcaaaata tttgtttaagaatcttgactacttacttagtctaaaccctaacgtacatg gttagacatattagacacaattctattctatagcttcttaacaaacgttt agcataatccgaaattggttttaccaatatttattaccgtacgtgtgttt ttttctgtaagaaaggaaaaaaagccaactcatgattcttctgatattgc atgtaatatatttgccaaataagcttacgacacaaacacaatgacactat gacagtaagatatcatttcaaaatacggatatacccccaaattggtggca atgacaaagaaaaaaagagttcttcacagtggcacattcgtaatacatat gaactttggtggttgtttcgtaatatagatcgtacttaaaacctctaaac accgttctctttatttgccatcttcttcattatcatcatctccatctctc tctctctctctctcatttttcttgaaaaag-

GGCCTGCAV GGGCCAGTGCAVCTGG 3'

(B) Sequence verification and confirmation.

| Sequence (bp) | Mismatch | Predicted/Experimental |
|---|---|---|
| 415 | SNP | a/— |

Sequence Q.C. notes:

(C) Predicted vs. Experimental sequence alignment.

```
Score = 1892 bits (984), Expect = 0.0
Identities = 999/1000 (99%), Gaps = 1/1000 (0%)
Strand = Plus/Plus
Query = Predicted (nucleotides 24–1024 of SEQ ID NO: 64)
Subject = Experimental (nucleotides 24–1024 of SEQ ID NO: 65)

Query: 1    tagctagatttctatataaacagaagaaagttaaaaagcaaataaaaattcacaaataga 60
            ||||||||||||||||||||||||||||||||||||||||||||||||||||||||||||
Sbjct: 1    tagctagatttctatataaacagaagaaagttaaaaagcaaataaaaattcacaaataga 60

Query: 61   aatcgaacaaaaagctatgaaaatataaataccataaccttatggaaaaacgatgaaatg 120
            ||||||||||||||||||||||||||||||||||||||||||||||||||||||||||||
Sbjct: 61   aatcgaacaaaaagctatgaaaatataaataccataaccttatggaaaaacgatgaaatg 120

Query: 121  cttaacaaaaaaactttggcaatggcatgcatgtgcctgtaacagaaggcccccataag 180
            ||||||||||||||||||||||||||||||||||||||||||||||||||||||||||||
Sbjct: 121  cttaacaaaaaaactttggcaatggcatgcatgtgcctgtaacagaaggcccccataag 180

Query: 181  ctgttagtgatatacaacttaagcaaatgtgcactcttcacgcacttcccgcttttctaa 240
            ||||||||||||||||||||||||||||||||||||||||||||||||||||||||||||
Sbjct: 181  ctgttagtgatatacaacttaagcaaatgtgcactcttcacgcacttcccgcttttctaa 240

Query: 241  atttcaatttatttgtctacattttttgtccaaattattgatataattctaccacgacttc 300
            ||||||||||||||||||||||||||||||||||||||||||||||||||||||||||||
Sbjct: 241  atttcaatttatttgtctacattttttgtccaaattattgatataattctaccacgacttc 300

Query: 301  ccccacatgtccctccaaagagatccgtactacacagtctaccgacagcacatgcatgga 360
            ||||||||||||||||||||||||||||||||||||||||||||||||||||||||||||
Sbjct: 301  ccccacatgtccctccaaagagatccgtactacacagtctaccgacagcacatgcatgga 360

Query: 361  tttccaaaccatcttctttaaggataatccttgacattttttaatattaaaaaaataaca 420
            |||||||||||||||||||||||||||||||||||||||||||||||||||||| |||||
Sbjct: 361  tttccaaaccatcttctttaaggataatccttgacattttttaatattaaaaa-taaca 419

Query: 421  aaaattcaatatataaataacatcctaaatctatgttttggtagaaaacaagttctaaa 480
            ||||||||||||||||||||||||||||||||||||||||||||||||||||||||||||
Sbjct: 420  aaaattcaatatataaataacatcctaaatctatgttttggtagaaaacaagttctaaa 479
```

-continued

```
Query: 481  gttcacatttggacagtggttagtacttggtaatcaaaatatttgtttaagaatcttgac  540
            ||||||||||||||||||||||||||||||||||||||||||||||||||||||||||||
Sbjct: 480  gttcacatttggacagtggttagtacttggtaatcaaaatatttgtttaagaatcttgac  539

Query: 541  tacttacttagtctaaaccctaacgtacatggttagacatattagacacaattctattct  600
            ||||||||||||||||||||||||||||||||||||||||||||||||||||||||||||
Sbjct: 540  tacttacttagtctaaaccctaacgtacatggttagacatattagacacaattctattct  599

Query: 601  atagcttcttaacaaacgtttagcataatccgaaattggttttaccaatatttattaccg  660
            ||||||||||||||||||||||||||||||||||||||||||||||||||||||||||||
Sbjct: 600  atagcttcttaacaaacgtttagcataatccgaaattggttttaccaatatttattaccg  659

Query: 661  tacgtgtgttttttctgtaagaaaggaaaaaaagccaactcatgattcttctgatattg  720
            ||||||||||||||||||||||||||||||||||||||||||||||||||||||||||||
Sbjct: 660  tacgtgtgttttttctgtaagaaaggaaaaaaagccaactcatgattcttctgatattg  719

Query: 721  catgtaatatatttgccaataagcttacgacacaaacacaatgacactatgacagtaag  780
            ||||||||||||||||||||||||||||||||||||||||||||||||||||||||||||
Sbjct: 720  catgtaatatatttgccaataagcttacgacacaaacacaatgacactatgacagtaag  779

Query: 781  atatcatttcaaaatacggatataccccaaattggtggcaatgacaaagaaaaaaagag  840
            ||||||||||||||||||||||||||||||||||||||||||||||||||||||||||||
Sbjct: 780  atatcatttcaaaatacggatataccccaaattggtggcaatgacaaagaaaaaaagag  839

Query: 841  ttcttcacagtggcacattcgtaatacatatgaactttggtggttgtttcgtaatataga  900
            ||||||||||||||||||||||||||||||||||||||||||||||||||||||||||||
Sbjct: 840  ttcttcacagtggcacattcgtaatacatatgaactttggtggttgtttcgtaatataga  899

Query: 901  tcgtacttaaaacctctaaacaccgttctctttatttgccatcttcttcattatcatcat  960
            ||||||||||||||||||||||||||||||||||||||||||||||||||||||||||||
Sbjct: 900  tcgtacttaaaacctctaaacaccgttctctttatttgccatcttcttcattatcatcat  959

Query: 961  ctccatctctctctctctctctcatttcttgaaaaag  1000
            ||||||||||||||||||||||||||||||||||||||
Sbjct: 960  ctccatctctctctctctctctcatttcttgaaaaag  999
```

Promoter Expression Report #178

Promoter Tested In: *Arabidopsis thaliana*, Wassilewskija (WS) ecotype
Spatial expression summary:

| | |
|---|---|
| Flower | H stomata |
| Ovule | Post-fertilization: M endothelium |
| Stem | H stomata |
| Leaf | H stomata |
| Cotyledon | H stomata |
| Rosette Leaf | H stomata |
| Primary Root | M epidermis H pericycle H root hairs |
| Lateral root | H initials H lateral root cap |

Observed expression pattern:
T1 mature: High GFP expression in guard cells throughout mature plant aerial tissue and endothelium cell layer of developing seed.
T2 seedling: GFP expression in trichomes and guard cells of cotyledons and rosette leaves. Primary expression in root localized to pericycle cells and lateral root initials and later in mature lateral root cap. Weak epidermal and root hair expression.

Expected expression pattern: Shade Induced
Selection Criteria: Ceres expression data
Gene: short-chain dehydrogenase/reductase (SDR) family protein, oxidoreductase activity
GenBank: NM_120332 *Arabidopsis thaliana* short-chain dehydrogenase/reductase (SDR) family protein (At5g02540) mRNA, complete cds gi|30679675|ref|NM_120332.2|[30679675]
Source Promoter Organism: *Arabidopsis thaliana*, Columbia
Vector: pNewbin4-HAP1-GFP
Marker Type: GFP-ER
Generation Screened: XT1 Mature XT2 Seedling ↑T2 Mature ↑T3 Seedling
Inductions completed:

| Treatment: | Age: | Gen: | Time points: | Events Screened/ Response | Response: |
|---|---|---|---|---|---|
| 1. Far red | 7 days | T2 | 1 Hr | 2/0 | No |

| Promoter Expression Report #178 | | | | |
|---|---|---|---|---|
| Far Red$_{730}$ = 525 μW/cm$^2$ | | 24 Hr | 2/2 | Yes |

Inducible expression summary:
Treatment:                  Time point induced:  Organs induced:              Tissues induced:
1. Far red                  1 Hr                 No differences observed.    Stomata (guard cells)
Far Red$_{730}$ = 525 μW/cm$^2$  24 Hr           Cotyledon                    Stomata (guard cells)
                                                 Rosette Leaf
T1 Mature Plant Expression         Organs/Tissues screened
Events Screened:     n = 4     Events Expressing:     n = 2
GFP Expression Detected
X Flower                    ↑pedicel ↑receptacle ↑nectary ↑sepal ↑petal ↑filament ↑anther ↑pollen
                            ↑carpel ↑style ↑papillae ↑vascular ↑epidermis H stomata ↑trichome
                            ↑silique
↑ Silique                   ↑stigma ↑style ↑carpel ↑septum ↑placentae ↑transmitting tissue ↑vascular
                            ↑epidermis ↑stomata ↑abscission zone ↑ovule
X Ovule                     Pre-fertilization: ↑primordia ↑inner integument ↑outer integument ↑embryo
                            sac ↑funiculus ↑chalaza ↑micropyle ↑gametophyte
                            Post-fertilization: ↑zygote ↑suspensor ↑embryo sack ↑inner integument
                            ↑outer integument M endothelium ↑seed coat ↑primordia ↑chalaza
                            ↑micropyle ↑early endosperm ↑mature endosperm ↑embryo
    ↑ Embryo                ↑suspensor ↑preglobular ↑globular ↑heart ↑torpedo ↑late ↑mature
                            ↑provascular ↑hypophysis ↑radicle ↑cotyledons ↑hypocotyl
X Stem                      ↑epidermis ↑cortex ↑vascular ↑xylem ↑phloem ↑pith H stomata ↑trichome
X Leaf                      ↑petiole ↑mesophyll ↑vascular ↑epidermis ↑trichome ↑primordia H stomata
                            ↑stipule ↑margin
↑ Shoot apical meristem     ↑shoot apical meristem ↑flower primordium
X Endothelium (Ed) in the developing seed
X Embryo (Em) in the developing seed
X Endosperm (En) in the developing seed
X Guard cell (Gc) in the inflorescence meristem and the leaf
T2 Seedling Expression     Tissues Screened
Events Screened: n = 2         Events Expressing: n = 2
Seedlings expressing/Seedlings screened
Event-03: 6(6)
Event-04: 5(6)
GFP Expression Detected
↑ Hypocotyl                 ↑epidermis ↑cortex ↑vascular ↑xylem ↑phloem ↑stomata
X Cotyledon                 ↑mesophyll ↑vascular ↑epidermis ↑margin H stomata
                            ↑hydathode
X Rosette Leaf              ↑mesophyll ↑vascular ↑epidermis ↑trichome ↑petiole
                            ↑primordia H stomata ↑stipule ↑margin ↑hydathode
X Primary Root              M epidermis ↑trichoblast ↑atrichoblast ↑cortex ↑endodermis
                            ↑vascular ↑xylem ↑phloem H pericycle ↑quiescent
                            ↑columella ↑root cap H root hairs
X Lateral root              ↑epidermis ↑trichoblast ↑atrichoblast ↑cortex ↑endodermis
                            H initials ↑flanking cells ↑vascular H lateral root cap
↑ Shoot apical meristem     ↑shoot apical meristem
X Epidermis (Ep) in the root
X Guard cell (Gc) in the cotyledon
X Lateral root initial (Lri) in the lateral root initial
X Pericycle (Pr) in the root
X Root cap (Rc) in the lateral root cap
X Root hair (Rh) in the root
X Trichome (Tc) in the leaf
Promoter utility
Trait Area:      Stress, Nitrogen, PG&D
Sub-trait Area:  Drought, drought, nitrogen uptake, root architecture
Utility:         Among other uses this promoter sequence could be useful to
                 improve: Tolerance to drought conditions. Tolerance to heat
                 conditions. Modulation of responses to abiotic stress. Modulation of
                 plant interactions with insects and protection against insects.
                 Modulation of production and loading of volatiles into trichomes and
                 other epidermal cells. Enhanced root rate and root size. Modulation of
                 water and mineral ion uptake. Modulation of lateral root initiation and
                 growth and root architecture.
Construct:                 PT0678
Promoter candidate I.D:    15295964
cDNA I.D:                  12712683 (OCKHAM3-CD)
Lines expressing:          PT0678-03, -04

(A) Predicted promoter sequence (1000 bp).

(SEQ ID NO: 66)
5' CCAGTCGA▼TTGGCCCGAT▼CGGCC-aattaaatgaaactcgcccct aaattaggagggatttgggtaagtggtaacacattcactggaaacatgtg aagaaaggaggatgtcaagtagctgaaaactcagtatagtaaccaacggc ttctcaccaacctttcattaataatttggtcatccctatattttattca acattttgtttttcaatagcttagagcaccttaataccttcagtgtttt tttataaaaaaaacaaaaattgggattaatcatcaatccccaaatgtaa cgtttacttagattatgttcattttctatacacacaaatcatattcttt tgttttaatcttcgaaaaacgagaggacattaaataccctaaaaagga ggggacattactaccaacgtacattaacatgtttgatagcaaacgattta ttttgttcgttttgaaaagggaaagtaatgtgtaaattatgtaaagatt aataaactttatggtatagtaacattttcgaataataagagagggaaaa cactcgccattgtcggcaatttagaaccaatattagaagggttttttag agaaaaaggacttaaaagtttagagaccttaacaacaacttatttagaaa tagacatgcttaagttgacaacagcgagtttatttctatatcgaagaaa -continued
aatacgaacttttcttaattagatttcgaatgcatgcactatcgagaat cgaccgtcacaagaaaaaactaatatacatactgtacatatctatattca atattggtggggatgggtttaatgtgtatttataattcatggataaattc acacaataaggtccatgaaactagaaggtaccaaaaataagcattaatga ctctttgccacttatatatatgattctctcatagtaccattttattctcc caaacctatcttcttcttcctctcttgtctctctcgctctctctcttcta cattgtttcttgaggtcaatctattaaaa-

GGCCGATC▼GGGCCAATCGA▼CTGG 3'

(B) Sequence verification.

| Predicted Position (bp) | Mismatch | Predicted/Experimental |
|---|---|---|
| 14 bp | SNP | t/— |
| 235 bp | SNP | a/— |
| Sequence Q.C notes. | | |

(C) Predicted vs. Experimental sequence alignment.

```
(Query: nucleotides 24-1024 of SEQ ID NO: 66)
(Subject: nucleotides 24-1021 of SEQ ID NO: 67)
Score = 1892 bits (984), Expect = 0.0
Identities = 998/1000 (99%), Gaps = 2/1000 (0%)

Query:    1 aattaaatgaaactcgcccctaaattaggagggatttgggtaagtggtaacacattcact   60
            ||||||||||||| ||||||||||||||||||||||||||||||||||||||||||||||
Sbjct:    1 aattaaatgaaac-cgccctaaattaggagggatttgggtaagtggtaacacattcact   59

Query:   61 ggaaacatgtgaagaaaggaggatgtcaagtagctgaaaactcagtatagtaaccaacgg  120
            ||||||||||||||||||||||||||||||||||||||||||||||||||||||||||||
Sbjct:   60 ggaaacatgtgaagaaaggaggatgtcaagtagctgaaaactcagtatagtaaccaacgg  119

Query:  121 cttctcaccaacctttcattaataatttggtcatccctatattttattcaacattttgt  180
            ||||||||||||||||||||||||||||||||||||||||||||||||||||||||||||
Sbjct:  120 cttctcaccaacctttcattaataatttggtcatccctatattttattcaacattttgt  179

Query:  181 ttttcaatagcttagagcaccttaataccttcagtgttttttataaaaaaaacaaaa  240
            |||||||||||||||||||||||||||||||||||||||||||||||||||| |||||
Sbjct:  180 ttttcaatagcttagagcaccttaataccttcagtgtttttttataaaaaaa-caaaa  238

Query:  241 attgggattaatcatcaatccccaaatgtaacgtttacttagattatgttcattttcta  300
            ||||||||||||||||||||||||||||||||||||||||||||||||||||||||||||
Sbjct:  239 attgggattaatcatcaatccccaaatgtaacgtttacttagattatgttcattttcta  298

Query:  301 tacacacaaatcatattcttttgttttaatcttcgaaaaacgagaggacattaaataccc  360
            ||||||||||||||||||||||||||||||||||||||||||||||||||||||||||||
Sbjct:  299 tacacacaaatcatattcttttgttttaatcttcgaaaaacgagaggacattaaataccc  258

Query:  361 ctaaaaaggagggacattactaccaacgtacattaacatgtttgatagcaaacgattt  420
            ||||||||||||||||||||||||||||||||||||||||||||||||||||||||||||
Sbjct:  359 ctaaaaaggagggacattactaccaacgtacattaacatgtttgatagcaaacgattt  418

Query:  421 attttgttcgttttgaaaagggaaagtaatgtgtaaattatgtaaagattaataaactt  480
            ||||||||||||||||||||||||||||||||||||||||||||||||||||||||||||
Sbjct:  419 attttgttcgttttgaaaagggaaagtaatgtgtaaattatgtaaagattaataaactt  478

Query:  481 ttatggtatagtaacattttcgaataataagagagggaaaacactcgccattgtcggcaa  540
            ||||||||||||||||||||||||||||||||||||||||||||||||||||||||||||
Sbjct:  479 ttatggtatagtaacattttcgaataataagagagggaaaacactcgccattgtcggcaa  538
```

```
-continued

Query:  541  tttagaaccaatattagaagggttttttagagaaaaaggacttaaaagtttagagacct  600
             ||||||||||||||||||||||||||||||||||||||||||||||||||||||||||
Sbjct:  539  tttagaaccaatattagaagggttttttagagaaaaaggacttaaaagtttagagacct  598

Query:  601  taacaacaacttatttagaaatagacatgcttaagttgacaacagcgagtttattttcta  660
             ||||||||||||||||||||||||||||||||||||||||||||||||||||||||||||
Sbjct:  599  taacaacaacttatttagaaatagacatgcttaagttgacaacagcgagtttattttcta  658

Query:  661  tatcgaagaaaaatacgaacttttctcttaattagatttcgaatgcatgcactatcgagaa  720
             ||||||||||||||||||||||||||||||||||||||||||||||||||||||||||||
Sbjct:  659  tatcgaagaaaaatacgaacttttctcttaattagatttcgaatgcatgcactatcgagaa  718

Query:  721  tcgaccgtcacaagaaaaaactaatatacatactgtacatatctatattcaatattggtg  780
             ||||||||||||||||||||||||||||||||||||||||||||||||||||||||||||
Sbjct:  719  tcgaccgtcacaagaaaaaactaatatacatactgtacatatctatattcaatattggtg  778

Query:  781  gggatgggtttaatgtgtatttataattcatggataaattcacacaataaggtccatgaa  840
             ||||||||||||||||||||||||||||||||||||||||||||||||||||||||||||
Sbjct:  779  gggatgggtttaatgtgtatttataattcatggataaattcacacaataaggtccatgaa  838

Query:  841  actagaaggtaccaaaaataagcattaatgactctttgccacttatatatatgattctct  900
             ||||||||||||||||||||||||||||||||||||||||||||||||||||||||||||
Sbjct:  839  actagaaggtaccaaaaataagcattaatgactctttgccacttatatatatgattctct  898

Query:  901  catagtaccattttattctcccaaacctatcttcttcttcctctcttgtctctctcgctc  960
             ||||||||||||||||||||||||||||||||||||||||||||||||||||||||||||
Sbjct:  899  catagtaccattttattctcccaaacctatcttcttcttcctctcttgtctctctcgctc  958

Query:  961  tctctcttctacattgtttcttgaggtcaatctattaaaa                     1000
             ||||||||||||||||||||||||||||||||||||||||
Sbjct:  959  tctctcttctacattgtttcttgaggtcaatctattaaaa                     998
```

| Promoter Expression Report #193 |
| --- |

Promoter Tested In: *Arabidopsis thaliana*, Wassilewskija (WS) ecotype
Spatial expression summary:
Flower            H pedicel H receptacle L sepal H filament H carpel H epidermis H silique
Silique            H carpel H epidermis H abscission zone H ovule
Ovule            Post-fertilization: H seed coat H embryo
Embryo            L torpedo H late H mature H radicle L cotyledons
Stem            H epidermis H vascular
Leaf            H vascular L epidermis
Cotyledon            L epidermis
Rosette Leaf            H epidermis H primordia
Primary Root            L epidermis H vascular
Observed expression pattern:
T1 mature: GFP expressed in the inflorescence meristem, developing flower buds, mature flowers, embryos, seed coats of mature ovules, stem and leaves. At the inflorescence meristem, GFP is expressed throughout the stem and pedicels and sepals of developing flower buds. In mature flowers, GFP is expressed in pedicels, siliques, and filaments of stamens. In ovules, GFP expressed in mature or developing seed coats and embryos. GFP is expressed throughout torpedo stage embryo, and later is preferentially expressed in root cap of developing radicle. Weakly expressed in shoot apical meristem cells of embryo. GFP expressed in epidermal and vasculature cells of leaf and stem.
T2 seedling: High GFP expression at the shoot apex and root vasculature of seedlings. High GFP expression throughout epidermal cells of rosette leaves. Not expressed in guard cells. High GFP expression in vasculature of root near root transition zone decreasing toward root tip. Weak root epidermal expression.
Expected expression pattern:      Microarray
Selection Criteria:      Shade Induced
Gene:      expressed protein (At3g22231)
GenBank: NM_113121 *Arabidopsis thaliana* expressed protein (At3g22231) mRNA, complete cds gi|42565114|ref|NM_113121.3| [42565114]
Source Promoter Organism:      *Arabidopsis thaliana*, Columbia (Col) ecotype
Vector:      pNewbin4-HAP1-GFP
Marker Type:      GFP-ER
Generation Screened:      XT1 Mature XT2 Seedling ↑T2 Mature ↑T3 Seedling
Inductions completed.

| Treatment: | Age: | Gen: | Time points: | Events Screened/ Response | Response: |
| --- | --- | --- | --- | --- | --- |
| 1. Far red | 7 days | T2 | 1 Hr | 5/2 | Yes |
| Far Red$_{730}$ = 525 µW/cm$^2$ | | | 24 Hr | 5/2 | Yes |

Inducible expression summary:
Treatment:      Time point induced:      Organs induced:      Tissues induced:

-continued

| Promoter Expression Report #193 | | | |
|---|---|---|---|
| 1. Far red | 1 Hr | Rosette leaf | Epidermis |
| | | Petioles | Epidermis |
| | 24 Hr | Rosette leaf | Epidermis |
| | | Petioles | Epidermis |

T1 Mature Plant Expression  Organs/Tissues screened
Events Screened:   n = 4    Events Expressing:   n = 3
GFP Expression Detected
X Flower            H pedicel H receptacle ↑nectary L sepal ↑petal H filament ↑anther ↑pollen
                    H carpel ↑style ↑papillae ↑vascular H epidermis ↑stomata ↑trichome
                    H silique
X Silique           ↑stigma ↑style H carpel ↑septum ↑placentae ↑transmitting tissue ↑vascular
                    H epidermis ↑stomata H abscission zone H ovule
  X Ovule            Pre-fertilization: ↑primordia ↑inner integument ↑outer integument ↑embryo
                    sac ↑funiculus ↑chalaza ↑micropyle ↑gametophyte
                    Post-fertilization: ↑zygote ↑suspensor ↑ embryo sack ↑funiculus ↑inner
                    integument ↑outer integument ↑endothelium H seed coat ↑primordia
                    ↑chalaza ↑micropyle ↑early endosperm ↑mature endosperm H embryo
  X Embryo           ↑suspensor ↑preglobular ↑globular ↑heart L torpedo H late H mature
                    ↑provascular ↑hypophysis H radicle L cotyledons ↑root meristem ↑shoot
                    meristem
X Stem              H epidermis ↑ cortex H vascular ↑xylem ↑phloem ↑pith ↑stomata
                    ↑trichome
X Leaf              ↑petiole ↑mesophyll H vascular L epidermis ↑trichome ↑primordia
                    ↑stomata ↑stipule ↑margin
↑ Shoot apical meristem   ↑shoot apical meristem ↑flower primordium
X Anther (An) in the flower
X Chalaza (Ch) in the ovule
X Cotyledon (Co) in the ovule and embryo
X Cortex (Cr) in the stem
X Epidermis (Ep) in the inflorescence meristem, embryo, leaf and stem
X Filament (Fi) in the flower
X Flower (Fl) in the inflorescence meristem and flower
X Micropyle (Mp) in the ovule
X Ovule (Ov) in the ovule
X Pedicel (Pd) in the inflorescence meristem and flower
X Root cap (Rc) in the ovule and embryo
X Radicle (Rd) in the ovule
X Sepal (Se) in the flower
X Silique (Si) in the flower
X Shoot apical meristem (SAM) in the ovule
X Seed coat (Sc) in the ovule
X Vascular (Vs) in the flower and leaf
X Vascular bundle (Vb) in the stem
T2 Seedling Expression     Tissues Screened
Events Screened: n = 2           Events Expressing: n = 2
Seedlings expressing/Seedlings screened
Event-01: 5/6
Event-02: 3/6
↑ No GFP Expression Detected
↑ Hypocotyl              ↑epidermis ↑cortex ↑vascular ↑xylem ↑phloem ↑stomata
X Cotyledon              ↑mesophyll ↑vascular L epidermis ↑margin ↑stomata
                         ↑hydathode
X Rosette Leaf           ↑mesophyll ↑vascular H epidermis ↑trichome ↑petiole
                         H primordia ↑stomata ↑stipule ↑margin ↑hydathode
X Primary Root           L epidermis ↑trichoblast ↑atrichoblast ↑cortex ↑endodermis
                         H vascular ↑xylem ↑phloem ↑pericycle ↑quiescent
                         ↑columella ↑root cap ↑root hairs
↑ Lateral root           ↑epidermis ↑trichoblast ↑atrichoblast ↑cortex ↑endodermis
                         ↑initials ↑flanking cells ↑vascular ↑lateral root cap
↑ Shoot apical meristem   ↑shoot apical meristem
X Cotyledon (Co) in the seedling
X Hypocotyl (Hy) in the seedling
X Guard cell (Gc) in the rosette leaf
X Leaf (Lf) in the seedling
X Root hair (Rh) in the seedling
X Vascular (Vs) in the seedling
Promoter utility
Trait Area:       PG&D
Sub-trait Area:   Shade avoidance, seed size
Utility:          Among other uses this promoter sequence could be useful to modulate
                  shade avoidance and seed size
Notes: 1) A very short gene and there are no TAIL hits in either the Salk or Ceres population.
Construct:                PT0859
Promoter candidate I.D:   15296003
cDNA I.D:                 23513118
Lines expressing:         PT0859-01, 02, 05

FIG. 1. (A) Predicted promoter region was PCR amplified from the Columbia ecotype of *A. thaliana*. Cloned promoter fragment shown with linker sequence containing BstXI and SfiI (▼) sites at both 5' and 3' in uppercase bold letters. (B) Promoter construct sequence is 5' verified in T1 mature plants and confirmed in the following generation by 5'and 3' sequencing of the entire promoter of two or 3 events. Sequences from all events are used to generate a consensus sequence. In every case, the sequences of the 2–3 events have matched. Nucleotide discrepancies between predicted and experimental consensus sequences are verified by manual inspection of chromatographs and shown in accompanying table. (C) Alignment of the experimental consensus sequence from transgenic lines versus the predicted promoter sequence is shown below.

(A) Predicted promoter sequence (604 bp).

5' CCAGTCGA▼TTGGCCCGAT▼CGGCC NNNNNNNNNNNNNNN GGCCTGCA▼GGGCCAGTGCA▼CTGG 3'        (SEQ ID NO: 2)

>193.PT0859 predicted        (SEQ ID NO: 68)

acagatcacaccaacataaggaacaaagccaaaactattaatcatggttcaaaggcagttggttaatcactttttcat tttcatgaaatgttaaattaattaatcatcaaaagaggttatttaatttacatagagtttagagcaatacccaaaaaa aaaaaaaagaggttctaaaagacagttccaggaacaaaataattcaaatttgttaaattcctcatgttttacgacgtc atgtacgtgtacgtcatgtacgtgacgaaagccatttctgcaacaaaccatttctcactttcatctcaaccataggta tcgctttcctctgcccttgtgcatttcaaacaatatcatttgctttatctctgcaattatatatgtgttggatataac caaaaaacctagacctaccacttcgctaaggtaggtctgtccgtgagttgtctgtgattagatgtttttattgttcaa tattgactcttctttcttttatataatgaataatgtaaaaatttcctaatatttgtctaccttataaattagaagca caacactctctcctcttcacaaatctcacatcctcactcctcagctcctcaaatcaga >193.PT0859 experimental        (SEQ ID NO: 69)
acagatcacaccaacataaggaacaaagccaaaactattaatcatggttc aaaggcagttggttaatcactttttcattttcatgaaatgttaaattaat taatcatcaaaagaggttatttaatttacatagagtttagagcaataccc aaaaaaaaaaaaaagaggttctaaaagacagttccaggaacaaaataatt caaatttgttaaattcctcatgttttacgacgtcatgtacgtgtacgtca tgtacgtgacgaaagccatttctgcaacaaaccatttctcactttcatct caaccataggtatcgctttcctctgcccttgtgcatttcaaacaatatca tttgctttatctctgcaattatatatgtgttggatataaccaaaaaacct agacctaccacttcgctaaggtaggtctgtccgtgagttgtctgtgatta gatgttttattgttcaatattgactcttctttcttttatataatgaata atgtaaaaatttcctaatatttgtctaccttataaattagaagcacaac actctctcctcttcacaaatctcacatcctcaccctcagctcctcaaat caga (B) Sequence verification and confirmation.

| Sequence (bp) | Mismatch | Predicted/Experimental |
|---|---|---|
| 584 | SNP | t/c |
| Sequence Q.C. notes: | | |

(C) Predicted vs. Experimental sequence alignment.

```
Query = Predicted (SEQ ID NO: 68)
Subject = Experimental (SEQ ID NO: 69)
Score = 1156 bits (601), Expect = 0.0
Identities = 603/604 (99%)
Strand = Plus/Plus Query:   1  acagatcacaccaacataaggaacaaagccaaaactattaatcatggttcaaaggcagtt   60
            ||||||||||||||||||||||||||||||||||||||||||||||||||||||||||||
Sbjct:   1  acagatcacaccaacataaggaacaaagccaaaactattaatcatggttcaaaggcagtt   60

Query:  61  ggttaatcacttttcattttcatgaaatgttaaattaattaatcatcaaaagaggttat  120
            ||||||||||||||||||||||||||||||||||||||||||||||||||||||||||||
Sbjct:  61  ggttaatcacttttcattttcatgaaatgttaaattaattaatcatcaaaagaggttat  120

Query: 121  ttaatttacatagagtttagagcaatacccaaaaaaaaaaaaagaggttctaaaagaca  180
            ||||||||||||||||||||||||||||||||||||||||||||||||||||||||||||
Sbjct: 121  ttaatttacatagagtttagagcaatacccaaaaaaaaaaaaagaggttctaaaagaca  180

Query: 181  gttccaggaacaaaataattcaaatttgttaaattcctcatgttttacgacgtcatgtac  240
            ||||||||||||||||||||||||||||||||||||||||||||||||||||||||||||
Sbjct: 181  gttccaggaacaaaataattcaaatttgttaaattcctcatgttttacgacgtcatgtac  240

Query: 241  gtgtacgtcatgtacgtgacgaaagccatttctgcaacaaaccatttctcactttcatct  300
            ||||||||||||||||||||||||||||||||||||||||||||||||||||||||||||
Sbjct: 241  gtgtacgtcatgtacgtgacgaaagccatttctgcaacaaaccatttctcactttcatct  300

Query: 301  caaccataggtatcgctttcctctgcccttgtgcatttcaaacaatatcatttgctttat  360
            ||||||||||||||||||||||||||||||||||||||||||||||||||||||||||||
Sbjct: 301  caaccataggtatcgctttcctctgcccttgtgcatttcaaacaatatcatttgctttat  360

Query: 361  ctctgcaattatatgtgttggatataaccaaaaaacctagacctaccacttcgctaag  420
            ||||||||||||||||||||||||||||||||||||||||||||||||||||||||||||
Sbjct: 361  ctctgcaattatatgtgttggatataaccaaaaaacctagacctaccacttcgctaag  420

Query: 421  gtaggtctgtccgtgagttgtctgtgattagatgttttattgttcaatattgactcttc  480
            ||||||||||||||||||||||||||||||||||||||||||||||||||||||||||||
Sbjct: 421  gtaggtctgtccgtgagttgtctgtgattagatgttttattgttcaatattgactcttc  480

Query: 481  tttcttttatataatgaataatgtaaaaaatttcctaatatttgtctaccttataaatta  540
            ||||||||||||||||||||||||||||||||||||||||||||||||||||||||||||
Sbjct: 481  tttcttttatataatgaataatgtaaaaaatttcctaatatttgtctaccttataaatta  540

Query: 541  gaagcacaacactctctcctcttcacaaatctcacatcctcactcctcagctcctcaaat  600
            ||||||||||||||||||||||||||||||||||||||||||||||||||||||||||||
Sbjct: 541  gaagcacaacactctctcctcttcacaaatctcacatcctcactcctcagctcctcaaat  600

Query: 601  caga                                                          604
            ||||
Sbjct: 601  caga                                                          604
```

| Promoter Expression Report #203 |
| --- |

Promoter Tested In: *Arabidopsis thaliana*, Wassilewskija (WS) ecotype
Spatial expression summary:
Hypocotyl     L stomata
Cotyledon     L stomata
Rosette Leaf   L stomata
Primary Root   L epidermis H endodermis
Observed expression pattern:
T1 mature: No expression observed.
T2 seedling: Primary GFP expression in root endodermal cell layer with weak expression in epidermal cells near transition zone. Guard cell expression throughout aerial tissue.
Expected expression pattern:    Shade Induced
Selection Criteria:           Ceres expression data
Gene:                         Expressed protein
GenBank: NM_125622 *Arabidopsis thaliana* expressed protein (At5g62280) mRNA, complete cds
gi|30697652|ref|NM_125622.2|[30697652]
Source Promoter Organism:     *Arabidopsis thaliana*, Columbia
Vector:                     pNewbin4-HAP1-GFP
Marker Type:           GFP-ER
Generation Screened:    XT1 Mature XT2 Seedling ↑T2 Mature ↑T3 Seedling -continued Promoter Expression Report #203

Inductions completed:

| Treatment: | Age: | Gen: | Time points: | Events Screened/ Response | Response: |
|---|---|---|---|---|---|
| 1. Far red | 7 days | T2 | 1 Hr | 2/0 | No |
| Far Red$_{730}$ = 525 µW/cm$^2$ | | | 24 Hr | 2/0 | No |

Inducible expression summary:

| Treatment: | Time point induced: | Organs induced: | Tissues induced: |
|---|---|---|---|
| 1. Far red | 1 Hr | No differences observed. | |
| Far Red$_{730}$ = 525 µW/cm$^2$ | 24 Hr | No differences observed. | |

Observation note: No differences were observed between control and experimental seedlings under far red conditions. Difference in expression levels compared to original T2 seedling screen. Higher expression can be seen in root epidermal cells and no GFP in guard cells can be detected.

T1 Mature Plant Expression Organs/Tissues screened

Events Screened:    n = 3    Events Expressing:    n = 0

X No GFP Expression Detected

T2 Seedling Expression    Tissues Screened

Events Screened: n = 2    Events Expressing: n = 2

Seedlings expressing/Seedlings screened

Event-01: 2/6

Event-04: 2/6

GFP Expression Detected

| X Hypocotyl | ↑epidermis ↑cortex ↑vascular ↑xylem ↑phloem L stomata |
|---|---|
| X Cotyledon | ↑mesophyll ↑vascular ↑epidermis ↑margin L stomata ↑hydathode |
| X Rosette Leaf | ↑mesophyll ↑vascular ↑epidermis ↑trichome ↑petiole ↑primordia L stomata ↑stipule ↑margin ↑hydathode |
| X Primary Root | L epidermis ↑trichoblast ↑atrichoblast ↑cortex H endodermis ↑vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |

X Cortex (Cr) in the root

X Endodermis (Eo) in the root

X Epidermis (Ep) in the seedling

X Guard cells (Gc) in the seedling

X Vascular bundle (Vb) in the root

Promoter utility

| Trait Area: | Stress, nutrients |
|---|---|
| Sub-trait Area: | Drought, nitrogen uptake |
| Utility: | Among other uses this promoter sequence could be useful to improve: Modulation of all responses to drought and heat stress. Protection against drought stress. Protection against heat stress. |
| Notes: | Endogenous promoter is down-regulated in heat and drought, up-regulated in far red light and circadian rhythm. |
| Construct: | PT0679 |
| Promoter candidate I.D: | 15295967 |
| cDNA I.D: | 12732583 (OCKHAM3-CD) |
| Lines expressing: | PT0679-01 |

FIG. 1. (A) Predicted promoter region was PCR amplified from the Columbia ecotype of *A. thaliana*. Cloned fragment shown with primer sequence underlined and linkers containing BsTXI and Sfi I (▼) sites at both 5' and 3' in uppercase bold letters. (B) Promoter construct sequence is 5' verified in T1 mature plants and confirmed in the following generation by 5' and 3' sequencing of the entire promoter of two or 3 events. Sequences from all events are used to generate a consensus sequence. In every case, the sequences of the 2–3 events have matched. Nucleotide discrepancies between predicted and experimental consensus sequences are verified by manual inspection of chromatographs and shown in accompanying table. (C) Alignment of the experimental consensus sequence from transgenic lines versus the predicted promoter sequence is shown below.

(A) Predicted promoter sequence (1000 bp).

```
5' CCAGTCGA▼TTGGCCCGAT▼CGGCCtaagaaaaactgtaggcttgtt gtcagaacaaacatggacccatgttctctatgtccctaagatgtgtacca atctcaattcacttcttttgttgcactattttttaaaaaataacttttat tttatattttgagatctccattgccctgctgcactagacattacagctc attttttccttataattcaatccctagctattttttctttcttattagttt aaactaatcatatttgggtaattagcgttgaaactatctatcatatcaat tttaatgatacatatgcaatactttatgtgagtatatgcatgtatgcatg ttccaacatccagattaatgactaacgtttaagccctgatttttttcagag aaattttgtgttgtacctatgtttgtattacacacaatatttaccattgt
```

-continued
```
ttaacatgtacacatgtgtttataaatctccgtacactataatgcatatt tgaaccatatatgacagaaagttttccactagttctaattacattttgtt gcccttcctactcgtctattgcctatagaaatattattttagttatgat taagaattgggatgcacattccgaaattaattattaaatgccactatgaa gaacccttgaacatagtctaattcaattttaagatcataaggaacattaa cagtgacaatagctaaggtctctcgacaatgagacaatccgcttttttaaa tatatacatataagagataccatattgtatacatatgcagatacaattac aacttgaccaaatttattcaatttctccttctctttatatcaataagaaa ctattcatgatactggaccagcctgtttgaatcttgtcccatccacaaat ctcccaatatataaataaagaaccttcacccgtaaaaccaaaaccatcaa caacttcaaagctttctaagcaagagattgagagaaatcggatttttcttt ctaagactcaaaatatctaaaaacaataGGCCTGCA▼GGGCCAGTGCA▼

CTGG 3'
```

(B) Sequence verification and confirmation.

| Sequence (bp) | Mismatch | Predicted/Experimental |
|---|---|---|
| 1–1000 | none | 1000/1000 (100%) |
| Sequence Q.C. notes: | | |

(C) Predicted vs. Experimental sequence alignment.

```
Query = Predicted (nucleotides 24–1023 of SEQ ID NO: 57)
Subject = Experimental (nucleotides 24–1023 of SEQ ID NO: 57)
Score = 1923 bits (1000), Expect = 0.0
Identities = 1000/1000 (100%)

Query:   1 taagaaaaactgtaggcttgttgtcagaacaaacatggacccatgttctctatgtccta    60
           ||||||||||||||||||||||||||||||||||||||||||||||||||||||||||||
Sbjct:   1 taagaaaaactgtaggcttgttgtcagaacaaacatggacccatgttctctatgtccta    60

Query:  61 agatgtgtaccaatctcaattcacttcttttgttgcactattttttaaaaaataactttt   120
           ||||||||||||||||||||||||||||||||||||||||||||||||||||||||||||
Sbjct:  61 agatgtgtaccaatctcaattcacttcttttgttgcactattttttaaaaaataactttt   120

Query: 121 attttatattttgagatctccattgccctgctgcactagacattacagctcattttttc   180
           ||||||||||||||||||||||||||||||||||||||||||||||||||||||||||||
Sbjct: 121 attttatattttgagatctccattgccctgctgcactagacattacagctcattttttc   180

Query: 181 cttataattcaatccctagctattttctttcttattagtttaaactaatcatatttggg   240
           ||||||||||||||||||||||||||||||||||||||||||||||||||||||||||||
Sbjct: 181 cttataattcaatccctagctattttctttcttattagtttaaactaatcatatttggg   240

Query: 241 taattagcgttgaaactatctatcatatcaattttaatgatacatatgcaatactttatg   300
           ||||||||||||||||||||||||||||||||||||||||||||||||||||||||||||
Sbjct: 241 taattagcgttgaaactatctatcatatcaattttaatgatacatatgcaatactttatg   300

Query: 301 tgagtatatgcatgtatgcatgttccaacatccagattaatgactaacgtttaagccctg   360
           ||||||||||||||||||||||||||||||||||||||||||||||||||||||||||||
Sbjct: 301 tgagtatatgcatgtatgcatgttccaacatccagattaatgactaacgtttaagccctg   360

Query: 361 atttttcagagaaattttgtgttgtacctatgtttgtattacacacaatatttaccatt   420
           ||||||||||||||||||||||||||||||||||||||||||||||||||||||||||||
Sbjct: 361 atttttcagagaaattttgtgttgtacctatgtttgtattacacacaatatttaccatt   420
```

-continued

```
Query:  421  gtttaacatgtacacatgtgtttataaatctccgtacactataatgcatatttgaaccat  480
             ||||||||||||||||||||||||||||||||||||||||||||||||||||||||||||
Sbjct:  421  gtttaacatgtacacatgtgtttataaatctccgtacactataatgcatatttgaaccat  480

Query:  481  atatgacagaaagttttccactagttctaattacattttgttgccctttcctactcgtct  540
             ||||||||||||||||||||||||||||||||||||||||||||||||||||||||||||
Sbjct:  481  atatgacagaaagttttccactagttctaattacattttgttgccctttcctactcgtct  540

Query:  541  attgcctatagaaatattattttagttatgattaagaatttgggatgcacattccgaaatt  600
             ||||||||||||||||||||||||||||||||||||||||||||||||||||||||||||
Sbjct:  541  attgcctatagaaatattattttagttatgattaagaatttgggatgcacattccgaaatt  600

Query:  601  aattattaaatgccactatgaagaacccttgaacatagtctaattcaattttaagatcat  660
             ||||||||||||||||||||||||||||||||||||||||||||||||||||||||||||
Sbjct:  601  aattattaaatgccactatgaagaacccttgaacatagtctaattcaattttaagatcat  660

Query:  661  aaggaacattaacagtgacaatagctaaggtctctcgacaatgagacaatccgcttttta  720
             ||||||||||||||||||||||||||||||||||||||||||||||||||||||||||||
Sbjct:  661  aaggaacattaacagtgacaatagctaaggtctctcgacaatgagacaatccgcttttta  720

Query:  721  aatatatacatataagagataccatattgtatacatatgcagatacaattacaacttgac  780
             ||||||||||||||||||||||||||||||||||||||||||||||||||||||||||||
Sbjct:  721  aatatatacatataagagataccatattgtatacatatgcagatacaattacaacttgac  780

Query:  781  caaatttattcaatttctccttctctttatatcaataagaaactattcatgatactggac  840
             ||||||||||||||||||||||||||||||||||||||||||||||||||||||||||||
Sbjct:  781  caaatttattcaatttctccttctctttatatcaataagaaactattcatgatactggac  840

Query:  841  cagcctgtttgaatcttgtcccatccacaaatctcccaatatataaataaagaaccttca  900
             ||||||||||||||||||||||||||||||||||||||||||||||||||||||||||||
Sbjct:  841  cagcctgtttgaatcttgtcccatccacaaatctcccaatatataaataaagaaccttca  900

Query:  901  cccgtaaaaccaaaaccatcaacaacttcaaagctttctaagcaagagattgagagaaat  960
             ||||||||||||||||||||||||||||||||||||||||||||||||||||||||||||
Sbjct:  901  cccgtaaaaccaaaaccatcaacaacttcaaagctttctaagcaagagattgagagaaat  960

Query:  961  cggattttctttctaagactcaaaatatctaaaaacaata                      1000
             ||||||||||||||||||||||||||||||||||||||||
Sbjct:  961  cggattttctttctaagactcaaaatatctaaaaacaata                      1000
```

| Promoter Expression Report #204 |
| --- |

Promoter Tested In: *Arabidopsis thaliana*, Wassilewskija (WS) ecotype
Spatial expression summary:
Cotyledon         M hydathode
Primary Root    H epidermis H root hairs
Observed expression pattern:
T1 mature: No expression.
T2 seedling: GFP predominately expressed throughout root epidermal cells. Highest at
GFP expression near hypocotyl root transition zone decreasing toward root tip.
Expected expression pattern:        Shade Induced
Selection Criteria:                          Microarray
Gene:                                              zinc finger (CCCH-type) family protein
GenBank: NM_123793 *Arabidopsis thaliana* zinc finger (CCCH-type) family protein
(At5g44260) mRNA, complete cds gi |30694483|ref|NM_123793.2|[30694483]
Source Promoter Organism:        *Arabidopsis thaliana*, Columbia (Col) ecotype
Vector:                                           pNewbin4-HAP1-GFP
Marker Type:                                GFP-ER
Generation Screened:     XT1 Mature XT2 Seedling ↑T2 Mature ↑T3 Seedling
Inductions completed.

|  |  |  |  | Events Screened/ |  |
| --- | --- | --- | --- | --- | --- |
| Treatment: | Age: | Gen: | Time points: | Response | Response: |
| 1. Far red | 7 days | T2 | 1 Hr | 2/0 | No |
| Far Red$_{730}$ = 525 μW/cm$^2$ |  |  | 24 Hr | 2/0 | No |

Inducible expression summary:
Treatment:                      Time point induced:      Organs induced:   Tissues induced:
1. Far red                         No differences observed.
Far Red$_{730}$ = 525 μW/cm$^2$
T1 Mature Plant Expression    Organs/Tissues screened
Events Screened:    n = 3       Events Expressing:    n = 0
X No GFP Expression Detected
T2 Seedling Expression    Tissues Screened
Events Screened: n = 2            Events Expressing: n = 2
Seedlings expressing/Seedlings screened

-continued

Promoter Expression Report #204

Event-01: 5/6
Event-02: 5/6
GFP Expression Detected

| | |
|---|---|
| ↑ Hypocotyl | ↑epidermis ↑cortex ↑vascular ↑xylem ↑phloem ↑stomata |
| X Cotyledon | ↑mesophyll ↑vascular ↑epidermis ↑margin ↑stomata M hydathode |
| ↑ Rosette Leaf | ↑mesophyll ↑vascular ↑epidermis ↑trichome ↑petiole ↑primordia ↑stomata ↑stipule ↑margin ↑hydathode |
| X Primary Root | H epidermis ↑trichoblast ↑atrichoblast ↑cortex ↑endodermis ↑vascular ↑xylem ↑phloem ↑pericycle ↑quiescent ↑columella ↑root cap H root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Epidermis (Ep) in the seedling | |
| X Hydathode (Hd) in the cotyledons | |

Table 3.  Promoter utility
Trait Area:  Nutrients
Sub-trait Area:  Nitrogen
Utility:  Among other uses this promoter sequence could be useful to modulate tolerance to high nitrogen.
Notes: 1). There are 2 knock-out alleles in the Ceres population and 4 in the Salk population. One of the knock-out alleles has a yellow-green viable phenotype.
Construct:  PT0675
Promoter candidate I.D:  15295952
cDNA I.D:  24418776 (OCKHAM3-CD)
Lines expressing:  PT0675-01, -02

(A) Predicted promoter sequence (1000 bp).

5' CCAGTCGA▼TTGGCCCGAT▼CGGCC NNNNNNNNNNNNNN GGCCTGCA▼GGGCCAGTCA▼CTGG 3'   (SEQ ID NO: 2)

>204.PT0675 predicted   (SEQ ID NO: 70)
ttgtttaacacctcaaacctgttaagactaatcacaatgttcgaagataatgccatttctatatatatttagtatagc atcacacatgcgttctgtgttgcaaagtttactctagagttatcactgagtcatgactcatgatgaccattattatag tattagtacttttaagttttaggtcgagaatatgaagctaatacatgcatgtaatgatgtaaatatgcctaccttaaa aaatatcgaattattcagaaacaatgactcgatatccgtaagaaaccgccagctcctgctgaattgcatgaacctatc ttaatattctttcgccacgaactcttcccttttgtctccttcttataactctacacatcatcatttcttttccactaa ataacttacaatacgtataccttttctttttgtcaatttaaatcaacactaagatatactttaaatacgaatcatt taaatgaatataatgtactaattgtttcagattttatttcctgtttaaaaatatactcatgaactaaaactaattaat aaaatgtggataaattaaagccttttaacaaaaaaaaatgtggataaattaatatcaatatgtttccttttttatttt attttatctatttcaaaaaaataagttattcaatacatatgttgatattttgactattttaatcataatttaaatca attgttgtgttcttaagcaaaatatctaaaaacgaatataaccacgtccaccatagaagcactgcaattttagcattc taaaacatccttgatatttttttgtcaacgtcttattatctttttatctcaaaccatgtatatggatgtatccactaac gcatatatagagacaattaggcatctatcattttatcccacacttatctcttcctatctctctctcattcaaaccc aaataggaaacaaatacacaaaagtataataaaaagtctttctctcatctttcgccacgtagac (B) Sequence verification and confirmation.

>204.PT0675 experimental   (SEQ ID NO: 71)
ttgtttaacacctcaaacctgttaagactaatcacaatgttcgaagataa tgccatttctatatatatttagtatagcatcacacatgcgttctgtgttg caaagtttactctagagttatcactgagtcatgactcatgatgaccatta ttatagtattagtacttttaagttttaggtcgagaatgtgaagctaatac atgcatgtaatgatgtaaatatgcctaccttaaaaaatatcgaattattc agaaacaatgactcgatatccgtaagaaaccgccagctcctgctgaattg catgaacctatcttaatattctttcgccacgaactcttcccttttgtctc cttcttataactctacacatcatcatttcttttccactaaataacttaca atacgtataccttttctttttgtcaatttaaatcaacactaagatata -continued ctttaaatacgaatcatttaaatgaatataatgtactaattgtttcagat tttatttcctgtttaaaaatatactcatgaactaaaactaattaataaaa tgtggataaattaaagccttttaacaaaaaaaaaatgtggataaattaat atcaatatgtttcctttttattttattttatctatttcaaaaaataagt tattcaatacatatgttgatattttgactattttaatcataatttaaat caattgttgtgttcttaagcaaaatatctaaaaacgaatataaccacgtc caccatagaagcactgcaatttagcattctaaaacatccttgatatttt tttgtcaacgtcttattatcttttatctcagaccatgtatatggatgtat ccactaacgcatatatatagagacaattaggcatctatcattttatccca -continued cacttatctcttcctatctctctctcattcaaacccaaataggaaacaaa tacacaaaagtataataaaaagtctttctctcatctttcgccacgtagac

| Sequence (bp) | Mismatch | Predicted/Experimental |
|---|---|---|
| 188 | SNP | a/g |
| 830 | SNP | a/g |

Sequence Q.C. notes:

(C) Predicted vs. Experimental sequence alignment.

```
Score = 1911 bits (994), Expect = 0.0
Identities = 998/1000 (99%)
Strand = Plus/Plus
Query = Predicted (SEQ ID NO: 70)
Subject = Experimental (SEQ ID NO: 71)

Query:   1 ttgtttaacacctcaaacctgttaagactaatcacaatgttcgaagataatgccatttct   60
           ||||||||||||||||||||||||||||||||||||||||||||||||||||||||||||
Sbjct:   1 ttgtttaacacctcaaacctgttaagactaatcacaatgttcgaagataatgccatttct   60

Query:  61 atatatatttagtatagcatcacacatgcgttctgtgttgcaaagtttactctagagtta  120
           ||||||||||||||||||||||||||||||||||||||||||||||||||||||||||||
Sbjct:  61 atatatatttagtatagcatcacacatgcgttctgtgttgcaaagtttactctagagtta  120

Query: 121 tcactgagtcatgactcatgatgaccattattatagtattagtacttttaagttttaggt  180
           ||||||||||||||||||||||||||||||||||||||||||||||||||||||||||||
Sbjct: 121 tcactgagtcatgactcatgatgaccattattatagtattagtacttttaagttttaggt  180

Query: 181 cgagaatatgaagctaatacatgcatgtaatgatgtaaatatgcctaccttaaaaaatat  240
           ||||||| ||||||||||||||||||||||||||||||||||||||||||||||||||||
Sbjct: 181 cgagaatgtgaagctaatacatgcatgtaatgatgtaaatatgcctaccttaaaaaatat  240

Query: 241 cgaattattcagaaacaatgactcgatatccgtaagaaaccgccagctcctgctgaattg  300
           ||||||||||||||||||||||||||||||||||||||||||||||||||||||||||||
Sbjct: 241 cgaattattcagaaacaatgactcgatatccgtaagaaaccgccagctcctgctgaattg  300

Query: 301 catgaacctatcttaatattctttcgccacgaactcttcccttttgtctccttcttataa  360
           ||||||||||||||||||||||||||||||||||||||||||||||||||||||||||||
Sbjct: 301 catgaacctatcttaatattctttcgccacgaactcttcccttttgtctccttcttataa  360

Query: 361 ctctacacatcatcatttcttttccactaaataacttacaatacgtataccttttctttt  420
           ||||||||||||||||||||||||||||||||||||||||||||||||||||||||||||
Sbjct: 361 ctctacacatcatcatttcttttccactaaataacttacaatacgtataccttttctttt  420

Query: 421 tttgtcaatttaaatcaacactaagatatactttaaatacgaatcatttaaatgaatata  480
           ||||||||||||||||||||||||||||||||||||||||||||||||||||||||||||
Sbjct: 421 tttgtcaatttaaatcaacactaagatatactttaaatacgaatcatttaaatgaatata  480

Query: 481 atgtactaattgtttcagattttatttcctgtttaaaaatatactcatgaactaaaacta  540
           ||||||||||||||||||||||||||||||||||||||||||||||||||||||||||||
Sbjct: 481 atgtactaattgtttcagattttatttcctgtttaaaaatatactcatgaactaaaacta  540

Query: 541 attaataaaatgtggataaattaaagccttttaacaaaaaaaaatgtggataaattaat  600
           ||||||||||||||||||||||||||||||||||||||||||||||||||||||||||||
Sbjct: 541 attaataaaatgtggataaattaaagccttttaacaaaaaaaaatgtggataaattaat  600

Query: 601 atcaatatgtttcctttttattttattttatctatttcaaaaaataagttattcaatac  660
           ||||||||||||||||||||||||||||||||||||||||||||||||||||||||||||
Sbjct: 601 atcaatatgtttcctttttattttattttatctatttcaaaaaataagttattcaatac  660

Query: 661 atatgttgatattttgactattttaatcataatttaaatcaattgttgtgttcttaagc  720
           ||||||||||||||||||||||||||||||||||||||||||||||||||||||||||||
Sbjct: 661 atatgttgatattttgactattttaatcataatttaaatcaattgttgtgttcttaagc  720
```

```
Query:  721  aaaatatctaaaaacgaatataaccacgtccaccatagaagcactgcaattttagcattc  780
             ||||||||||||||||||||||||||||||||||||||||||||||||||||||||||||
Sbjct:  721  aaaatatctaaaaacgaatataaccacgtccaccatagaagcactgcaattttagcattc  780

Query:  781  taaaacatccttgatattttttgtcaacgtcttattatcttttatctcaaaccatgtat   840
             |||||||||||||||||||||||||||||||||||||||||||||| |||||||
Sbjct:  781  taaaacatccttgatattttttgtcaacgtcttattatcttttatctcagaccatgtat   840

Query:  841  atggatgtatccactaacgcatatatatagagacaattaggcatctatcattttatccca  900
             ||||||||||||||||||||||||||||||||||||||||||||||||||||||||||||
Sbjct:  841  atggatgtatccactaacgcatatatatagagacaattaggcatctatcattttatccca  900

Query:  901  cacttatctcttcctatctctctcattcaaacccaaataggaaacaaatacacaaaag   960
             ||||||||||||||||||||||||||||||||||||||||||||||||||||||||||
Sbjct:  901  cacttatctcttcctatctctctcattcaaacccaaataggaaacaaatacacaaaag   960

Query:  961  tataataaaaagtctttctctcatctttcgccacgtagac                     1000
             ||||||||||||||||||||||||||||||||||||||||
Sbjct:  961  tataataaaaagtctttctctcatctttcgccacgtagac                     1000
```

---

Promoter Expression Report #205

Promoter Tested In: *Arabidopsis thaliana*, Wassilewskija (WS) ecotype
Spatial expression summary:
Silique          L funiculus H ovule
Ovule            Post-fertilization: L funiculus H outer integument
Hypocotyl        L epidermis
Cotyledon        H epidermis H petiole
Rosette Leaf     H epidermis H petiole
Primary Root     H endodermis
Observed expression pattern:
T1 mature: GFP expression highly specific to second cell layer of the outer integument in developing seed. Also expressed at ovule connective site of funiculus. No expression observed in pre-fertilized ovules.
T2 seedling: GFP exhibits expression in a highly polar fashion in cotyledons and rosette leaves. GFP is expressed proximal-distal on the abaxial surface of the petioles of cotyledons and rosette leaves with respect to the shoot apical meristem. Low GFP expression observed on the adaxial surface of petioles of cotyledons and rosette leaves. GFP expression in epidermal cells of hypocotyl at the root transition zone decreases toward apex. Highly specific expression of GFP in endodermis cells of the root.
Expected expression pattern:       Shade Induced
Selection Criteria:                Ceres expression data
Gene:                              Acyl CoA reductase, putative
GenBank: NM_122155 *Arabidopsis thaliana* acyl CoA reductase, putative/male-sterility protein, putative (At5g22500) mRNA, complete cds gi|30688503|ref|NM_22155.2|[30688503]
Source Promoter Organism:          *Arabidopsis thaliana*, Columbia ecotype
Vector:                            pNewbin4-HAP1-GFP
Marker Type:                       GFP-ER
Generation Screened:    XT1 Mature XT2 Seedling ↑T2 Mature ↑T3 Seedling
Inductions completed.

|  |  |  |  | Events Screened/ |  |
|---|---|---|---|---|---|
| Treatment: | Age: | Gen: | Time points: | Response | Response: |
| 1. Far red | 7 days | T2 | 1 Hr | 2/0 | No |
| Far Red$_{730}$ = 525 μW/cm$^2$ |  |  | 24 Hr | 2/0 | No |

Inducible expression summary:
Treatment:       Time point induced:    Organs induced:        Tissues induced:
1. Far red       No differences observed. Images not shown.
T1 Mature Plant Expression Organs/Tissues screened
Events Screened:   n = 3     Events Expressing:    n = 3
GFP Expression Detected
↑ Flower              ↑pedicel ↑receptacle ↑nectary ↑sepal ↑petal ↑filament ↑anther ↑pollen
                      ↑carpel ↑style ↑papillae ↑vascular ↑epidermis ↑stomata ↑trichome
                      ↑silique
X Silique             ↑stigma ↑style ↑carpel ↑septum ↑placentae L funiculus ↑transmitting tissue
                      ↑vascular ↑epidermis ↑stomata ↑abscission zone H ovule
    X Ovule           Pre-fertilization: ↑primordia ↑inner integument ↑outer integument
                      ↑funiculus ↑embryo sac ↑chalaza ↑micropyle ↑gametophyte
                      Post-fertilization: ↑zygote ↑suspensor ↑ embryo sack L funiculus ↑inner
                      integument H outer integument ↑endothelium ↑seed coat ↑primordia
                      ↑chalaza ↑micropyle ↑early endosperm ↑mature endosperm ↑embryo
    ↑ Embryo          ↑suspensor ↑preglobular ↑globular ↑heart ↑torpedo ↑late ↑mature
                      ↑provascular ↑hypophysis ↑radicle ↑cotyledons ↑hypocotyl
↑ Stem                ↑epidermis ↑cortex ↑vascular ↑xylem ↑phloem ↑pith ↑stomata ↑trichome -continued Promoter Expression Report #205

| | |
|---|---|
| ↑ Leaf | ↑petiole ↑mesophyll ↑vascular ↑epidermis ↑trichome ↑primordia ↑stomata ↑stipule ↑margin |
| ↑ Shoot apical meristem | ↑shoot apical meristem ↑flower primordium |

X Funiculus (Fn) in developing seed and placenta
X Outer integument cell layer 1 (Oi)1 in developing seed
X Outer integument cell layer 2 (Oi)2 in developing seed
X Placenta (Pl) in the placenta
T2 Seedling Expression    Tissues Screened
Events Screened: n = 2        Events Expressing: n = 2
Seedlings expressing/Seedlings screened
Event-01: 2(6)
Event-02: 2(6)
GFP Expression Detected

| | |
|---|---|
| X Hypocotyl | L epidermis ↑cortex ↑vascular ↑xylem ↑phloem ↑stomata |
| X Cotyledon | ↑ mesophyll ↑vascular H epidermis ↑margin H petiole ↑stomata ↑hydathode |
| X Rosette Leaf | ↑ mesophyll ↑vascular H epidermis ↑trichome H petiole ↑primordia ↑stomata ↑stipule ↑margin ↑hydathode |
| X Primary Root | ↑epidermis ↑trichoblast ↑atrichoblast ↑cortex H endodermis ↑vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |

X Abaxial (Ab) in the rosette leaf
X Adaxial (Ad) in the rosette leaf
X Cotyledon (Co) in the rosette leaf
X Endodermis (Eo) in the seedling
X Hypocotyl (Hy) in the seedling
X Petiole (Pt) in the rosette leaf
X Rosette leaf (Rl) in the rosette leaf
X Root (Rt) in the seedling
Promoter utility
Trait Area:         PG&D, nutrients
Sub-trait Area:     Nitrogen use efficiency, seed size
Utility:            Among other uses this promoter sequence could be useful to modulate
seed growth and development, seed dormancy and germination. Also, useful
for enhancement of leaf and root growth, resulting in increased source capacity
and water and nutrient loading. Useful in procedures and technologies aimed
at improving source-sink relationships and seed filling and yield.
Construct:          PT0676
Promoter candidate I.D:   15295958
cDNA I.D:           23658955
Lines expressing:   PT0676-01, -02; Apr. 12, 2004

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3'        (SEQ ID NO: 2)

>205.PT0676 predicted        (SEQ ID NO: 72)
aagatagtacagtttcagtgttttgagaaaaaaagctgaactaaaactaaaatgtttaaggacacaatatttagtttc aattagataattcaacagtttgaacaattttttttttttttttttgaagtcatttatttatacaatgttttaaaacgc attaagcatttaggcagccgacaaacgcctattgtctaactgtaaataggcgcttccacttaggttcatattgcatat ttactatatgtgtatagtgacaaaaaccaatatttctcttattttggatgaaggtatagtagttgttaaatgttcaat ataattaagcattaatgacaaataaaataaaattaatttagttgataaaaagataatcttataaaaagatcgatgaat agatataatggtttactgaattctatagctcttaccttgcacgactatgtcccaaggagaggaagtaccttaactata attctgaacataattttgtctatcttggtgagtattatatgacctaaacccctttaataagaaaaagtataatactggc gtaacgtaataaattaacacaatcataagttgttgacaagcaaaaaaacatacataatttgtttaatgagatatatta gttatagttcttatgtcaaagtacaattatgcctaccaaaattaattaatgatttcaacaggaagtctgagatgatgg gccgacgtgtagttacgtttcttgaattgtgagagatggtatttattatactgaagaaaacattatttactaaataaa -continued ttttcatttcacatcttctgtaatcaatgcgggtagatgaagaagttgttaatacgatggccaaccatatggatctct tttttggcgtttctatatatagtaacctcgactccaaaggcattacgtgactcaataaaatcaagtcttttgtttcct tttatccaaaaaaaaaaaaagtcttgtgtttctcttaggttggttgagaatcatttcatttca (B) Sequence verification and confirmation.

(SEQ ID NO: 73)
>205.PT0676 experimental
aagatagtacagtttcagtgttttgagaaaaaaagctgaactaaaactaa aatgtttaaggacacaatatttagtttcaattagataattcaacagtttg aacaattttttttttttttttttgaagtcatttatttatacaatgtttta aaacgcattaagcatttaggcagccgacaaacgcctattgtctaactgta aataggcgcttccacttaggttcatattgcatatttactatatgtgtata gtgacaaaaccaatatttctcttattttggatgaaggtatagtagttgt taaatgttcaatataattaagcattaatgacaaataaaataaaattaatt tagttgataaaagataatcttataaaaagatcgatgaatagatataatg gtttactgaattctatagctcttaccttgcacgactatgtcccaaggaga ggaagtaccttaactataattctgaacataattttgtctatcttggtgag tattatatgacctaaacccttttaataagaaaaagtataatactggcgtaa cgtaataaattaacacaatcataagttgttgacaagcaaaaaaacataca -continued
taatttgtttaatgagatatattagttatagttcttatgtcaaagtacaa ttatgcctaccaaaattaattaatgatttcaacaggaagtctgagatgat gggccgacgtgtagttacgtttcttgaattgtgagagatggtatttatta tactgaagaaaacattatttactaaataaattttcatttcacatcttctg taatcaatgcgggtagatgaagaagttgttaatacgatggccaaccatat ggatctcttttttggcgtttctatatatagtaacctcgactccaaaggca ttacgtgactcaataaaatcaagtcttttgtttccttttatccaaaaaaa aaaaaagtcttgtgtttctcttaggttggttgagaatcatttcatttca (C) Predicted vs. Experimental sequence alignment.

| Sequence (bp) | Mismatch | Predicted/Experimental |
|---|---|---|
| 1–1000 | | |
| Sequence Q.C. notes: | | |

```
(Query: SEQ ID NO: 72)
(Subject: SEQ ID NO: 73)
Score = 1917 bits (997), Expect = 0.0
Identities = 999/1000 (99%)
Strand = Plus/Plus Query:   1 aagatagtacagtttcagtgttttgagaaaaaaagctgaactaaaactaaaatgttaag   60
           ||||||||||||||||||||||||||||||||||||||||||||||||||||||||||||
Sbjct:   1 aagatagtacagtttcagtgttttgagaaaaaaagctgaactaaaactaaaatgttaag   60

Query:  61 gacacaatatttagtttcaattagataattcaacagtttgaacaattttttttttttttt  120
           ||||||||||||||||||||||||||||||||||||||||||||||||||||||||||||
Sbjct:  61 gacacaatatttagtttcaattagataattcaacagtttgaacaattttttttttttttt  120

Query: 121 tttgaagtcatttatttatacaatgttttaaaacgcattaagcatttaggcagccgacaa  180
           ||||||||||||||||||||||||||||||||||||||||||||||||||||||||||||
Sbjct: 121 tttgaagtcatttatttatacaatgttttaaaacgcattaagcatttaggcagccgacaa  180

Query: 181 acgcctattgtctaactgtaaataggcgcttccacttaggttcatattgcatatttacta  240
           ||||||||||||||||||||||||||||||||||||||||||||||||||||||||||||
Sbjct: 181 acgcctattgtctaactgtaaataggcgcttccacttaggttcatattgcatatttacta  240

Query: 241 tatgtgtatagtgacaaaaccaatatttctcttattttggatgaaggtatagtagttgt  300
           ||||||||||||||||||||||||||||||||||||||||||||||||||||||||||||
Sbjct: 241 tatgtgtatagtgacaaaaccaatatttctcttattttggatgaaggtatagtagttgt  300

Query: 301 taaatgttcaatataattaagcattaatgacaaataaaataaaattaatttagttgataa  360
           ||||||||||||||||||||||||||||||||||||||||||||||||||||||||||||
Sbjct: 301 taaatgttcaatataattaagcattaatgacaaataaaataaaattaatttagttgataa  360

Query: 361 aaagataatcttataaaaagatcgatgaatagatataatggtttactgaattctatagct  420
           ||||||||||||||||||||||||||||||||||||||||||||||||||||||||||||
Sbjct: 361 aaagataatcttataaaaagatcgatgaatagatataatggtttactgaattctatagct  420
```

-continued

```
Query: 421  cttaccttgcacgactatgtcccaaggagaggaagtaccttaactataattctgaacata  480
            ||||||||||||||||||||||||||||||||||||||||||||||||||||||||||||
Sbjct: 421  cttaccttgcacgactatgtcccaaggagaggaagtaccttaactataattctgaacata  480

Query: 481  attttgtctatcttggtgagtattatatgacctaaacccttttaataagaaaaagtataat  540
            ||||||||||||||||||||||||||||||||||||||||||||||||||||||||||||
Sbjct: 481  attttgtctatcttggtgagtattatatgacctaaacccttttaataagaaaaagtataat  540

Query: 541  actggcgtaacgtaataaattaacacaatcataagttgttgacaagcaaaaaacataca   600
            ||||||||||||||||||||||||||||||||||||||||||||||||||||||||||||
Sbjct: 541  actggcgtaacgtaataaattaacacaatcataagttgttgacaagcaaaaaacataca   600

Query: 601  taatttgtttaatgagatatattagttatagttcttatgtcaaagtacaattatgcctac  660
            ||||||||||||||||||||||||||||||||||||||||||||||||||||||||||||
Sbjct: 601  taatttgtttaatgagatatattagttatagttcttatgtcaaagtacaattatgcctac  660

Query: 661  caaaattaattaatgatttcaacaggaagtctgagatgatgggccgacgtgtagttacgt  720
            ||||||||||||||||||||||||||||||||||||||||||||||||||||||||||||
Sbjct: 661  caaaattaattaatgatttcaacaggaagtctgagatgatgggccgacgtgtagttacgt  720

Query: 721  ttcttgaattgtgagagatggtatttattatactgaagaaaacattatttactaaataaa  780
            ||||||||||||||||||||||||||||||||||||||||||||||||||||||||||||
Sbjct: 721  ttcttgaattgtgagagatggtatttattatactgaagaaaacattatttactaaataaa  780

Query: 781  ttttcatttcacatcttctgtaatcaatgcgggtagatgaagaagttgttaatacgatgg  840
            ||||||||||||||||||||||||||||||||||||||||||||||||||||||||||||
Sbjct: 781  ttttcatttcacatcttctgtaatcaatgcgggtagatgaagaagttgttaatacgatgg  840

Query: 841  ccaaccatatggatctcttttttggcgtttctatatatagtaacctcgactccaaaggca  900
            ||||||||||||||||||||||||||||||||||||||||||||||||||||||||||||
Sbjct: 841  ccaaccatatggatctcttttttggcgtttctatatatagtaacctcgactccaaaggca  900

Query: 901  ttacgtgactcaataaaatcaagtcttttgtttccttttatccaaaaaaaaaaaaagtc   960
            ||||||||||||||||||||||||||||||||||||||||||||||||||||||||||||
Sbjct: 901  ttacgtgactcaataaaatcaagtcttttgtttccttttatccaaaaaaaaaaaaagtc   960

Query: 961  ttgtgtttctcttaggttggttgagaatcatttcatttca                      1000
            ||||||||||||||||||||||||||||||||||||||||
Sbjct: 961  ttgtgtttctcttaggttggttgagaatcatttcatttca                      1000
```

Promoter Expression Report #206
Promoter Tested In: *Arabidopsis thaliana*, Wassilewskija (WS) ecotype
Spatial expression summary:
Hypocotyl          H vascular
Cotyledon          L epidermis
Rosette Leaf       L vascular
Primary Root    H vascular H root cap
Observed expression pattern:
T1 mature: No expression observed.
T2 seedling: High GFP expression in vasculature of root and hypocotyl decreasing toward shoot and root apices. High GFP expression in cells of the root cap. Low epidermal expression in cotyledons.
Expected expression pattern:      Shade Inducible
Selection Criteria:                              Microarray
Gene: Auxin-responsive protein/indoleacetic acid-induced protein 1 (IAA1)
GenBank: NM_117536 *Arabidopsis thaliana* auxin-responsive protein/indoleacetic acid-induced protein 1 (IAA1) (At4g14560) mRNA, complete cds gi|30682899|ref| NM_117536.
Source Promoter Organism:      *Arabidopsis thaliana*, Columbia (Col) ecotype
Vector:                                 pNewbin4-HAP1-GFP
Marker Type:                        GFP-ER
Generation Screened:    XT1 Mature XT2 Seedling ↑T2 Mature ↑T3 Seedling
Inductions completed.

|  |  |  |  | Events Screened/ |  |
|---|---|---|---|---|---|
| Treatment: | Age: | Gen: | Time points: | Response | Response: |
| 1. Far red | 7 days | T2 | 1 Hr | 5/2 | Yes |
| Far Red$_{730}$ = 525 μW/cm$^2$ |  |  | 24 Hr | 5/2 | Yes |

Inducible expression summary:
| Treatment: | Time point induced: | Organs induced: | Tissues induced: |
|---|---|---|---|
| 1. Far red | 1 Hr, 24 Hr | Cotyledon | Vascualture, Epidermis |
|  |  | Rosette Leaf | Vascualture, Epidermis |
|  |  | Primary Root | Vascualture, Root Cap |
|  |  | Lateral root | Lateral root cap |
| T1 Mature Plant Expression |  | Organs/Tissues screened |  |

-continued

| | |
|---|---|
| Events Screened: n = 3 | Events Expressing: n = 0 |
| X No GFP Expression Detected | |
| T2 Seedling Expression | Tissues Screened |
| Events Screened: n = 2 | Events Expressing: n = 2 |
| Seedlings expressing/Seedlings screened | |
| Event-01: 5(6) | |
| Event-04: 4(6) | |
| GFP Expression Detected | |
| X Hypocotyl | ↑epidermis ↑cortex H vascular ↑xylem ↑phloem ↑stomata |
| X Cotyledon | ↑mesophyll ↑vascular L epidermis ↑margin ↑stomata ↑hydathode |
| X Rosette Leaf | ↑mesophyll L vascular ↑epidermis ↑trichome ↑petiole ↑primordia ↑stomata ↑stipule ↑margin ↑hydathode |
| X Primary Root | ↑epidermis ↑trichoblast ↑atrichoblast ↑cortex ↑endodermis H vascular ↑xylem ↑phloem ↑pericycle ↑quiescent ↑columella H root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Epidermis (Ep) in the cotyledons | |
| X Hypocotyl (Hy) in the root | |
| X Root cap (Rc) in the root | |
| X Vasculature (Vs) in the seedling, hypocotyl, and root | |
| Promoter utility | |
| Trait Area: | Nutrients |
| Sub-trait Area: | Nitrogen transport |
| Utility: | Among other uses this promoter sequence could be useful to modulate nitrogen transport. |
| Construct: | PT0680 |
| Promoter candidate I.D: | 15295973 |
| cDNA I.D: | 23535379 (13617391) |
| Lines expressing: | PT0680-01, -04 |

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3'    (SEQ ID NO: 2)

>206.PT0680 predicted    (SEQ ID NO: 74)

aaaatgttatttgagacagcatatcacatggccttaccatacttcctgcatccattattccattaagaacactcttca ccctcatccacatgcatctccctcccaatttatttactattgatcataattgtacaaacctatacttacaatttata tatgtgtctacgagaaaataaataatattttacagtgttttgtctattattttgttctatagtttcttgcaaacaaaa cattacttttcacgcaaaaactgtcgaaatatttataaaaggaaattgttaattcttcgatacaaattgaccattaat atttgatcatctattctagacatctactctaccatataccaaaccttacacaaaaatgaaatattttcatgaaaact accccacaactggggtgatcgaaaagcttgatctatatgatcaacatgtccaacactagtttcattttttctactat gatatccgatgatccaatctgaactatacaaaatgtatctagatattttcttgaatcaatccgaataacgaatagttg caaaacataaacctagcgtgatcgtgtggtagaaggacgaaggtcgagaagttctcttactcttatgattttctcttt actcatttgaccgtaagagaaagaaacggctaggatctcgcgtacgcaactggcggagacaaatcaggaccgttgaaa ataagaaagaagccgcgtccaaaatctttgtgtcccacctttgtcccttgcctctaacttgcctcctcatgctcccc gacaacgtcataattcatatctctctctctctcgttaacccaatttcaaagcatctttccttatataaatctctc tctctccctcaccattacacaacacacacaagcattttcaaggatatcaaatcacaatcccaagaagagcaataacaa gagaagaagaagtagttcaagaattaaggaagagagcttctccgttaaagtatagtgagagaat (B) Sequence verification and confirmation.

```
                                        (SEQ ID NO: 75)
>206.PT0680 experimental
aaaatgttatttgagacagcatatcacatggccttaccatacttcctgca tccattattccattaagaacactcttcaccctcatccacatgcatctccc tccccaatttatttactattgatcataattgtacaagcctatacttacaa tttatatatgtgtctacgagaaaataaataatattttacagtgttttgtc tattattttgttctatagcttcttgcaaacaagacattacttttcacgca aaaactgtcgaaatatttataaaaggaaattgttaattcttcgatacaaa ttgaccattaatatttgatcatctattctagacatctactctaccatata ccaaacctttacacaaaaatgaaatattttcatgaaaactacoccacaac tgggtgatcgaaaagcttgatctatatgatcaacatgtccaacactag tttcattttttctactatgatatccgatgatccaatctgaactatacaaa atgtatctagatattttcttgaatcaatccgaataacgaatagttgcaaa acataaacctagcgtgatcgtgtggtagaaggacgaaggtcgagaagttc tcttactcttatgatgttctctttactcatttgaccgtaagagaaagaaa
```

```
-continued
cggctaggatctcgcgtacgcaactggcggagacaaatcaggaccgttga aaataagaaagaagccgcgtccaaaatctttgtgtcccacctttgtcccc ttgcctctaacttgcctcctcatgctccccgacaacgtcataattcatat ctctctctctctcgttaaccctaatttcaaagcatctttccttatata aatctctctctctccctcaccattacacaacacacaagcattttcaag gatatcaaatcacaatcccaagaagagcaataacaagagaagaagaagta gttcaagaattaaggaagagagcttctccgttaaagtatagtgagagaat
```

| Sequence (bp) | Mismatch | Predicted/Experimental |
|---|---|---|
| 137 | SNP | a/g |
| 219 | SNP | t/c |
| 233 | SNP | a/g |
| 616 | SNP | t/g |

Sequence Q.C. notes:

(C) Predicted vs. Experimental sequence alignment.

```
Query = Predicted (SEQ ID NO: 74)
Subject = Experimental (SEQ ID NO: 75)
Score = 1900 bits (988), Expect = 0.0
Identities = 996/1000 (99%)
Strand = Plus/Plus Query:   1 aaaatgttatttgagacagcatatcacatggccttaccatacttcctgcatccattattc   60
           ||||||||||||||||||||||||||||||||||||||||||||||||||||||||||||
Sbjct:   1 aaaatgttatttgagacagcatatcacatggccttaccatacttcctgcatccattattc   60

Query:  61 cattaagaacactcttcaccctcatccacatgcatctccctccccaatttatttactatt  120
           ||||||||||||||||||||||||||||||||||||||||||||||||||||||||||||
Sbjct:  61 cattaagaacactcttcaccctcatccacatgcatctccctccccaatttatttactatt  120

Query: 121 gatcataattgtacaaacctatacttacaatttatatatgtgtctacgagaaaataaata  180
           |||||||||||||||||  |||||||||||||||||||||||||||||||||||||||||
Sbjct: 121 gatcataattgtacaagcctatacttacaatttatatatgtgtctacgagaaaataaata  180

Query: 181 atattttacagtgttttgtctattattttgttctatagtttcttgcaaacaaaacattac  240
           |||||||||||||||||||||||||||||||||||| ||||||||||||| |||||||||
Sbjct: 181 atattttacagtgttttgtctattattttgttctatagcttcttgcaaacaagacattac  240

Query: 241 ttttcacgcaaaaactgtcgaaatatttataaaggaaattgttaattcttcgatacaaa  300
           ||||||||||||||||||||||||||||||||||||||||||||||||||||||||||||
Sbjct: 241 ttttcacgcaaaaactgtcgaaatatttataaaaggaaattgttaattcttcgatacaaa  300

Query: 301 ttgaccattaatatttgatcatctattctagacatctactctaccatataccaaaccttt  360
           ||||||||||||||||||||||||||||||||||||||||||||||||||||||||||||
Sbjct: 301 ttgaccattaatatttgatcatctattctagacatctactctaccatataccaaaccttt  360

Query: 361 acacaaaaatgaaatattttcatgaaaactaccccacaactggggtgatcgaaaaagctt  420
           ||||||||||||||||||||||||||||||||||||||||||||||||||||||||||||
Sbjct: 361 acacaaaaatgaaatattttcatgaaaactaccccacaactggggtgatcgaaaaagctt  420

Query: 421 gatctatatgatcaacatgtccaacactagtttcattttttctactatgatatccgatga  480
           ||||||||||||||||||||||||||||||||||||||||||||||||||||||||||||
Sbjct: 421 gatctatatgatcaacatgtccaacactagtttcattttttctactatgatatccgatga  480

Query: 481 tccaatctgaactatacaaaatgtatctagatattttcttgaatcaatccgaataacgaa  540
           ||||||||||||||||||||||||||||||||||||||||||||||||||||||||||||
Sbjct: 481 tccaatctgaactatacaaaatgtatctagatattttcttgaatcaatccgaataacgaa  540

Query: 541 tagttgcaaaacataaacctagcgtgatcgtgtggtagaaggacgaaggtcgagaagttc  600
           ||||||||||||||||||||||||||||||||||||||||||||||||||||||||||||
Sbjct: 541 tagttgcaaaacataaacctagcgtgatcgtgtggtagaaggacgaaggtcgagaagttc  600
```

-continued

```
Query:  601  tcttactcttatgattttctctttactcatttgaccgtaagagaaagaaacggctaggat  660
             |||||||||||||| |||||||||||||||||||||||||||||||||||||||||||||
Sbjct:  601  tcttactcttatgatgttctctttactcatttgaccgtaagagaaagaaacggctaggat  660

Query:  661  ctcgcgtacgcaactggcggagacaaatcaggaccgttgaaaataagaaagaagccgcgt  720
             ||||||||||||||||||||||||||||||||||||||||||||||||||||||||||||
Sbjct:  661  ctcgcgtacgcaactggcggagacaaatcaggaccgttgaaaataagaaagaagccgcgt  720

Query:  721  ccaaaatctttgtgtcccacctttgtcccttgcctctaacttgcctcctcatgctcccc   780
             ||||||||||||||||||||||||||||||||||||||||||||||||||||||||||||
Sbjct:  721  ccaaaatctttgtgtcccacctttgtcccttgcctctaacttgcctcctcatgctcccc   780

Query:  781  gacaacgtcataattcatatctctctctctctcgttaaccctaatttcaaagcatctt    840
             ||||||||||||||||||||||||||||||||||||||||||||||||||||||||||||
Sbjct:  781  gacaacgtcataattcatatctctctctctctcgttaaccctaatttcaaagcatctt    840

Query:  841  tccttatataaatctctctctctccctcaccattacaacacacacaagcattttcaag    900
             ||||||||||||||||||||||||||||||||||||||||||||||||||||||||||||
Sbjct:  841  tccttatataaatctctctctctccctcaccattacaacacacacaagcattttcaag    900

Query:  901  gatatcaaatcacaatcccaagaagagcaataacaagagaagaagaagtagttcaagaat  960
             ||||||||||||||||||||||||||||||||||||||||||||||||||||||||||||
Sbjct:  901  gatatcaaatcacaatcccaagaagagcaataacaagagaagaagaagtagttcaagaat  960

Query:  961  taaggaagagagcttctccgttaaagtatagtgagagaat                      1000
             ||||||||||||||||||||||||||||||||||||||||
Sbjct:  901  taaggaagagagcttctccgttaaagtatagtgagagaat                      1000
```

Promoter Expression Report #208
Promoter Tested In: *Arabidopsis thaliana*, Wassilewskija (WS) ecotype
Spatial expression summary:
Flower         H pollen
Ovule          Pre-fertilization: H gametophyte
Embryo        H torpedo H late H mature H root meristem H shoot meristem
Cotyledon     H epidermis
Rosette Leaf   H epidermis H trichome H petiole
Primary Root  H epidermis H cortex H quiescent L root cap
Lateral root   H epidermis
Observed expression pattern:
T1 mature: GFP expressed in female gametophyte of developing ovules, pollen and in shoot and root apical meristems in torpedo through mature stage embryos. GFP also detected in suspensor cells of developing embryos. In mature embryos, GFP expression in the quiescent center can be clearly distinguished from root cap.
T2 Seedling: Predominantly expressed in the epidermis of petioles and rosette leaves. In the lower root, GFP expression in the epidermis appears to coincide with position of lateral root formation. At the root tip, GFP expression in the quiescent center can be clearly distinguished from root cap.
Expected expression pattern:    Shade inducible
Selection Criteria:          Microarray
Gene: FAD-binding domain-containing protein/cytokinin oxidase family protein
GenBank: NM_106199 *Arabidopsis thaliana* FAD-binding domain-containing protein/cytokinin oxidase family protein (At1g75450) mRNA, complete cds gi
Source Promoter Organism:    *Arabidopsis thaliana*, Columbia (Col) ecotype
Vector:                      pNewbin4-HAP1-GFP
Marker Type:           GFP-ER
Generation Screened:   XT1 Mature XT2 Seedling ↑T2 Mature ↑T3 Seedling
Inductions completed.

| Treatment: | Age: | Gen: | Time points: | Events Screened/ Response | Response: |
|---|---|---|---|---|---|
| 1. Far red | 7 days | T2 | 1 Hr | 5/1 | Yes |
| Far Red$_{730}$ = 525 µW/cm$^2$ | | | 24 Hr | 5/3 | Yes |

Inducible expression summary:

| Treatment: | Time point induced: | Organs induced: | Tissues induced: |
|---|---|---|---|
| 1. Far red | 1 Hr | Rosette leaf, | Epidermis |
|  |  | Petiole | Epidermis |
|  | 24 Hr | Cotyledons | Epidermis |
|  |  | Rosette leaf | Epidermis |
|  |  | Petiole | Epidermis |

T1 Mature Plant Expression    Organs/Tissues screened
Events Screened:    n = 6    Events Expressing:    n = 2
  GFP Expression Detected
X Flower              ↑pedicel ↑receptacle ↑nectary ↑sepal ↑petal ↑filament ↑anther H pollen
                      ↑carpel ↑style ↑papillae ↑vascular ↑epidermis ↑stomata ↑trichome
                      ↑silique

| | |
|---|---|
| ↑ Silique | ↑stigma ↑style ↑carpel ↑septum ↑placentae ↑transmitting tissue ↑vascular ↑epidermis ↑stomata ↑abscission zone ↑ovule |
| X Ovule | Pre-fertilization: ↑primordia ↑inner integument ↑outer integument ↑embryo sac ↑funiculus ↑chalaza ↑micropyle H gametophyte |
| X Embryo | Post-fertilization: ↑zygote ↑suspensor ↑embryo sack ↑funiculus ↑inner integument ↑outer integument ↑endothelium ↑seed coat ↑primordia ↑chalaza ↑micropyle ↑early endosperm ↑mature endosperm ↑embryo ↑suspensor ↑preglobular ↑globular ↑heart H torpedo H late H mature ↑provascular ↑hypophysis ↑radicle ↑cotyledons ↑hypocotyl H root meristem H shoot meristem |
| ↑ Stem | ↑epidermis ↑cortex ↑vascular ↑xylem ↑phloem ↑pith ↑stomata ↑trichome |
| ↑ Leaf | ↑petiole ↑mesophyll ↑vascular ↑epidermis ↑trichome ↑primordia ↑stomata ↑stipule ↑margin |
| ↑ Shoot apical meristem | ↑shoot apical meristem ↑flower primordium |
| X Female gametophyte (Fmg) in the ovule | |
| X Pollen (Po) in the ovule | |
| X Quiescent center (Qc) in the embryo | |
| X Shoot apical meristem (SAM) in the embryo | |
| X Suspensor (Su) in the ovule | |
| X Root apical meristem (RAM) in the embryo | |
| X Root cap (Rc) in the embryo | |
| T2 Seedling Expression | Tissues Screened |
| Events Screened:  n = 2 | Events Expressing: n = 2 |
| Seedlings expressing/Seedlings screened | |
| Event-01: 4/6 | |
| Event-03: 2/6 | |
| GFP Expression Detected | |
| ↑ Hypocotyl | ↑epidermis ↑cortex ↑vascular ↑xylem ↑phloem ↑stomata |
| X Cotyledon | ↑mesophyll ↑vascular H epidermis ↑margin ↑stomata ↑hydathode |
| X Rosette Leaf | ↑mesophyll ↑vascular H epidermis H trichome H petiole ↑primordia ↑stomata ↑stipule ↑margin ↑hydathode |
| X Primary Root | H epidermis ↑trichoblast ↑atrichoblast H cortex ↑endodermis ↑vascular ↑xylem ↑phloem ↑pericycle H quiescent ↑columella L root cap ↑root hairs |
| X Lateral root | H epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Cortex (Cr) in the root | |
| X Epidermis (Ep) in the cotyledon, rosette leaf, and the root | |
| X Lateral root (Lr) in the root | |
| X Petiole (Pt) in the rosette leaf | |
| X Quiescent center (Qc) in the root | |
| X Rosette leaf (Rl) | |
| X Root cap (Rc) in the root | |
| Promoter utility | |
| Trait Area: | PG&D, water use efficiency, source |
| Sub-trait Area: | Drought, heat, yield, shade avoidance, growing rate |
| Utility: | Among other uses this promoter sequence could be useful to modulate seed size, drought tolerance, yield, and growth rate. Useful to drive genes to repress shade avoidance responses - reduction of petiole elongation and early flowering. |
| Construct: | PT0682 |
| Promoter candidate I.D: | 15295985 |
| cDNA I.D: | 23530913 |
| Lines expressing: | PT0682-01, PT0682-03 |

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3'  (SEQ ID NO: 2)

>208.PT0682 predicted  (SEQ ID NO: 76)
cactacacacgtgtgacctcatcctctcccacgtgaatatccacgtggcgttcttccgttccgtttctcccatccctc ccatgcctctcccatgactctatttatcccaatcctctcttccttttcattaatttatcagttaaaattcctcttttt tcctagtagtatttggagttttcatatcaaaaagtttagactaaccctaaaaacattgatagaaaaacttatcatttt aaacgttcttggggaccaatcaaaatggttaattgtctagtgcctgttcttgattcttcagacatggttgcaaagtc catagtcaaatcaaggttatatgtagcttcaacactgataacacgtttattaacaaaaccatatcaaaatggttgttt tttgcattttcagtcttgacgtatacactgccatttttgaattagtcaaatcgttacgtagttggtctacgatgtctc gctgaaacaaatacatacgtgtgtatatacactatgcaagtagtatagttaacatcataattgaccctaaggaaaaaa -continued
gttaatgtaaacagtgacacgtagatatcacacggttctttttggttttgttaaagatgaacttgttaataaagaa tatgacgtgatcttctccggtacaactctttgtcctataaatagagaactcttgtcttcatattctcgacacacat ataaacgcacaaactcgttaaatttgtacgaatataattttttttaaaacactcgttataatatattaaagtttcacc caaaccgaaaaagagagaatctgtgcatgttgctcagaaaatcttcaaagcgtaatctgggcttacgttagctctca cgaaccccaaggatcttctatatatgttttttcatttccccataaaatctttcattatctaaaaaatattattatcg tatctttttcttctatatattcttcctcctcaatcttgattcttgtttcttgagtattctttg (B) Sequence verification and confirmation.

(SEQ ID NO: 77)
>208.PT0682 experimental
cactaaacacgtgtgacctcatcctctcccacgtgaatatccacgtggcg ttcttccgttccgtttctcccatccctcccatgcctctccccatgactct atttatcccaatcctctcttcctttcattaatttatcagttaaaattcct cttttttcctagtagtatttggagttttcatatcaaaaagtttagactaa ccctaaaaacattgatagaaaaacttatcattttaaacgttcttggggac caatcaaatggttaattgtctagtgcctgttcttgattcttcagacatg gttgcaaaagtccatagtcaaatcaaggttatatgtagcttcaacactga taacacgtttattaacaaaccatatcaaaatggttgtttttttgcattttc agtcttgacgtatacactgccattttgaattagtcaaatcgttacgtag ttggtctacgatgtctcgctgaaacaaatacatacgtgtgtatatacact atgcaagtagtatagttaacatcataattgaccctaaggaaaaagttaat gtaaacagtgacacgtagatatcacacggttcttttttggttttgttaa agatgaacttgttaataaagaatatgacgtgatcttctccggtacaactc tttgtcctataaatagagaactcttgtcttcatattctcgacacacat ataaacgcacaaactcgttaaatttgtacgaatataattttttttaaaac actcgttataatatattaaagtttcacccaaaccgaaaaagagagaatc tgtgcatgttgctcagaaaatcttcaaagcgtaatctgggcttacgttag ctctcacgaaccccaaggatcttctatatatgttttttcatttccccat aaaatctttcattatctaaaaaatattattatcgtatctttttcttcta tatattcttcctcctcaatcttgattcttgtttcttgagtattctttg

| Sequence (bp) | Mismatch | Predicted/Experimental |
|---|---|---|
| 6 | SNP | c/a |
| 370 | SNP | a/— |
| 547 | SNP | a/— |

Sequence Q.C. notes:

(C) Predicted vs. Experimental sequence alignment.

```
Query = Predicted (SEQ ID NO: 76)
Subject = Experimental (SEQ ID NO: 77)
Score = 1886 bits (981), Expect = 0.0
Identities = 997/1000 (99%), Gaps = 2/1000 (0%)
Strand = Plus/Plus Query:   1 cactacacacgtgtgacctcatcctctcccacgtgaatatccacgtggcgttcttccgtt   60
           |||||  |||||||||||||||||||||||||||||||||||||||||||||||||||||
Sbjct:   1 cactaaacacgtgtgacctcatcctctcccacgtgaatatccacgtggcgttcttccgtt   60

Query:  61 ccgtttctcccatccctcccatgcctctccccatgactctatttatcccaatcctctctt  120
           ||||||||||||||||||||||||||||||||||||||||||||||||||||||||||||
Sbjct:  61 ccgtttctcccatccctcccatgcctctccccatgactctatttatcccaatcctctctt  120

Query: 121 cctttcattaatttatcagttaaaattcctcttttttcctagtagtatttggagttttca  180
           ||||||||||||||||||||||||||||||||||||||||||||||||||||||||||||
Sbjct: 121 cctttcattaatttatcagttaaaattcctcttttttcctagtagtatttggagttttca  180

Query: 181 tatcaaaaagtttagactaaccctaaaaacattgatagaaaaacttatcattttaaacgt  240
           ||||||||||||||||||||||||||||||||||||||||||||||||||||||||||||
Sbjct: 181 tatcaaaaagtttagactaaccctaaaaacattgatagaaaaacttatcattttaaacgt  240

Query: 241 tcttggggaccaatcaaatggttaattgtctagtgcctgttcttgattcttcagacatg  300
           ||||||||||||||||||||||||||||||||||||||||||||||||||||||||||||
Sbjct: 241 tcttggggaccaatcaaatggttaattgtctagtgcctgttcttgattcttcagacatg  300

Query: 301 gttgcaaaagtccatagtcaaatcaaggttatatgtagcttcaacactgataacacgttt  360
           ||||||||||||||||||||||||||||||||||||||||||||||||||||||||||||
Sbjct: 301 gttgcaaaagtccatagtcaaatcaaggttatatgtagcttcaacactgataacacgttt  360
```

```
-continued

Query:  361  attaacaaaaccatatcaaaatggttgtttttgcattttcagtcttgacgtatacactg  420
             ||||||||| |||||||||||||||||||||||||||||||||||||||||||||||||
Sbjct:  361  attaacaaa-ccatatcaaaatggttgtttttgcattttcagtcttgacgtatacactg  419

Query:  421  ccattttgaattagtcaaatcgttacgtagttggtctacgatgtctcgctgaaacaaat  480
             |||||||||||||||||||||||||||||||||||||||||||||||||||||||||||
Sbjct:  420  ccattttgaattagtcaaatcgttacgtagttggtctacgatgtctcgctgaaacaaat  479

Query:  481  acatacgtgtgtatatacactatgcaagtagtatagttaacatcataattgaccctaagg  540
             ||||||||||||||||||||||||||||||||||||||||||||||||||||||||||||
Sbjct:  480  acatacgtgtgtatatacactatgcaagtagtatagttaacatcataattgaccctaagg  539

Query:  541  aaaaagttaatgtaaacagtgacacgtagatatcacacggttctttttggttttttgtt  600
             |||||  |||||||||||||||||||||||||||||||| |||||||||||||||||||
Sbjct:  540  aaaaa-gttaatgtaaacagtgacacgtagatatcacaggttctttttggttttttgtt  598

Query:  601  aaagatgaacttgttaataaagaatatgacgtgatcttctccggtacaactctttgtcct  660
             ||||||||||||||||||||||||||||||||||||||||||||||||||||||||||||
Sbjct:  599  aaagatgaacttgttaataaagaatatgacgtgatcttctccggtacaactctttgtcct  658

Query:  661  ataaatagagaactcttgtcttcatattctcgacacacacatataaacgcacaaactcgt  720
             ||||||||||||||||||||||||||||||||||||||||||||||||||||||||||||
Sbjct:  659  ataaatagagaactcttgtcttcatattctcgacacacacatataaacgcacaaactcgt  718

Query:  721  taaatttgtacgaatataattttttttaaaacactcgttataatatattaaagtttcacc  780
             ||||||||||||||||||||||||||||||||||||||||||||||||||||||||||||
Sbjct:  719  taaatttgtacgaatataattttttttaaaacactcgttataatatattaaagtttcacc  778

Query:  781  caaaccgaaaaagagagaatctgtgcatgttgctcagaaaatcttcaaagcgtaatctg  840
             ||||||||||||||||||||||||||||||||||||||||||||||||||||||||||
Sbjct:  779  caaaccgaaaaagagagaatctgtgcatgttgctcagaaaatcttcaaagcgtaatctg  838

Query:  841  ggcttacgttagctctcacgaaccccaaggatcttctatatatgttttttcatttcccc  900
             ||||||||||||||||||||||||||||||||||||||||||||||||||||||||||
Sbjct:  839  ggcttacgttagctctcacgaaccccaaggatcttctatatatgttttttcatttcccc  898

Query:  901  ataaaatctttcattatctaaaaaatattattatcgtatctttttcttctatatattct  960
             ||||||||||||||||||||||||||||||||||||||||||||||||||||||||||
Sbjct:  899  ataaaatctttcattatctaaaaaatattattatcgtatctttttcttctatatattct  958

Query:  961  tcctcctcaatcttgattcttgtttcttgagtattctttg                      1000
             ||||||||||||||||||||||||||||||||||||||||
Sbjct:  959  tcctcctcaatcttgattcttgtttcttgagtattctttg                      998
```

Promoter Expression Report #209
Promoter Tested In: *Arabidopsis thaliana*, Wassilewskija (WS) ecotype
Spatial expression summary:
Primary Root          H epidermis H cortex H trichoblast H atrichoblast
                      H root hairs
Observed expression pattern:
T1 mature: No expression observed.
T2 seedling: Root specific GFP expression. GFP expressed in root hair and non-root hair epidermal cells and cortex.
Expected expression pattern:    Shade induced
Selection Criteria:             Microarray
Gene:                           Cytochrome P450, CYP96A5
GenBank: NM_127760 *Arabidopsis thaliana* cytochrome P450, putative
(At2g21910) mRNA, complete cds gi|18399829|ref|NM_127760.1|[18399829]
Source Promoter Organism:       *Arabidopsis thaliana*, Columbia (Col) ecotype
Vector:                         pNewbin4-HAP1-GFP
Marker Type:                    GFP-ER
Generation Screened:    XT1 Mature XT2 Seedling ↑T2 Mature ↑T3 Seedling
Inductions completed.
                                              Events Screened/
Treatment:              Age:    Gen:  Time points:   Response        Response:
1. Far red              7 days  T2    1 Hr           5/1             Yes
Far Red$_{730}$ = 525 μW/cm$^2$       24 Hr          5/5             Yes
Inducible expression summary:
Treatment:         Time point induced:   Organs induced:    Tissues induced:
1. Far red              1 Hr             Cotyledons         Epidermis
                        24 Hr            Cotyledons         Epidermis
                                         Rosette leaf       Epidermis
                                         Petioles           Epidermis
T1 Mature Plant Expression       Organs/Tissues screened -continued

| | |
|---|---|
| Events Screened: n = 3 | Events Expressing: n = 0 |
| X No GFP Expression Detected | |
| T2 Seedling Expression | Tissues Screened |
| Events Screened: n = 2 | Events Expressing: n = 2 |
| Seedlings expressing/Seedlings screened | |
| Event-01: 5/6 | |
| Event-02: 5/6 | |
| GFP Expression Detected | |
| ↑ Hypocotyl | ↑epidermis ↑cortex ↑vascular ↑xylem ↑phloem ↑stomata |
| ↑ Cotyledon | ↑mesophyll ↑vascular ↑epidermis ↑margin ↑stomata ↑hydathode |
| ↑ Rosette Leaf | ↑mesophyll ↑vascular ↑epidermis ↑trichome ↑petiole ↑primordia ↑stomata ↑stipule ↑margin ↑hydathode |
| X Primary Root | H epidermis H trichoblast H atrichoblast H cortex ↑endodermis ↑vascular ↑xylem ↑phloem ↑pericycle ↑quiescent ↑columella ↑root cap H root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑shoot apical meristem |
| X Cortex (Cr) in the root | |
| X Epidermis (Ep) in the root | |
| X Root hair (Rh) in the root | |
| Promoter utility | |
| Trait Area: | Nutrients, PG&D |
| Sub-trait Area: | Nitrogen use efficiency, shade avoidance, plant size |
| Utility: Among other uses this promoter sequence could be useful to modulate nitrogen use efficiency, plant size, and shade avoidance. Root expression can be used to modify root architecture and tissue specific location of proteins. Expression in root cortex can be used to improve nitrogen transport to the phloem and xylem. Shade expression could be used to express negative regulators of shade response, e.g., inhibition of petiole elongation. | |
| Construct: | PT0683 |
| Promoter candidate I.D: | 15295991 |
| cDNA I.D: | 23499869 |
| Lines expressing: | PT0683-01, PT0683-02 |

(A) Predicted promoter sequence (1000 bp).

5' CCAGTCGA▼TTGGCCCGAT▼CGGCC NNNNNNNNNNNNNN GGCCTGCA▼GGGCCAGTGCA▼CTGG 3'     (SEQ ID NO: 2)

>209.PT0683 predicted     (SEQ ID NO: 78)

gattgaatgatgagtgtgcacccttgtattactaataaaaaatttagcaacagttataagctaacgtcatccatgagt cattcattagattcactatttgcgttctcaaaaatcgaattgttaaaatttgagaagctctaatatacgagtcaatga gatgtggcaaaagcatgtccttgaccataaaatttcgagggtcaactcattagataaggacaagaatcaaccaattg aaggcgtcttctataacaagtttctttattactaatattaaagtccaatggggtgaggggagaagaacttaaataaa aggaaataattggtaagtgaataaaatctaaatacgatactagatgattgatttgtgctagtgcatggtattagatca gatatgtgttactattcgaattcaaattggcatattccatgttgttgataagaaaattgtagaagtgtaaaagctgag ttactatattcaaactagtggtttacataaagtgagacaacaactgtttcacaaaaatgactataaaatagtaagtag tattaggtcaattgattttaaaattttaatcaaattcaaatttgtgatataatcaaatttgtttatagaaaatgttaa gaaatcaattttggcagaactaattcagtgagaaacaatcatttacaaaaacaattttaacattatttaacagtaaga tttgacatttaacccgttcgtgtgaacccatcatatctaacatggctctacccatgacgcctccatgccatggacaat tttgacagatcagaagttctgaacgtggacgaggtaagaacaccatgatgatacgattggagttagttatgtcgccac cgacatcactgccaatctcattaataaaagtggtactaaatctctaatctctattaactataaatataacaaagaacc aaaagaaagtttcttatctctcttatctttcataatttccaagaaacacaaacctttctacta (B) Sequence verification and confirmation.

(SEQ ID NO: 79)
```
>209.PT0683 experimental
gattgaatgatgagtgtgcacccttgtattactaataaaaaatttagcaa cagttataagctaacgtcatccatgagtcattcattagattcactatttg cgttctcaaaaatcgaattgttaaaatttgagaagctctaatatacgagt caatgagatgtggcaaaagcatgtccttgaccataaaatttcgaggggtc aactcattagataaggacaagaatcaaccaattgaaggcgtcttctataa caagtttctttattactaatattaaagtccaatggggtgaggggagaag aacttaaataaaaggaaataattggtaagtgaataaaaatctaaatacgat actagatgattgatttgtgctagtgcatggtattagatcagatatgtgtt actattcgaattcaaattggcatattccatgttgttgataagaaaattgt agaagtgtaaaagctgagttactatattcaaactagtggtttacataaag tgagacaacaactgtttcacaaaaatgactataaaatagtaagtagtatt aggtcaattgatttttaaaattttaatcaaattcaaatttgtgatataatc
```

-continued
```
aaatttgtttatagaaaatgttaagaaatcaattttggcagaactaattc agtgagaaacaatcatttacaaaaacaattttaacattatttaacagtaa gatttgacatttaacccgttcgtgtgaacccatcatatctaacatggctc tacccatgacgcctccatgccatggacaattttgacagatcagaagttct gaacgtggacgaggtaagaacaccatgatgatacgattggagttagttat gtcgccaccgacatcactgccaatctcattaataaaagtggtactaaatc tctaatctctattaactataaatataacaaagaaccaaaagaaagtttct tatctctcttatctttcataatttccaagaaacacaaaccttttctacta
```

| Sequence (bp) | Mismatch | Predicted/Experimental |
|---|---|---|
| 427 | SNP | t/c |

Sequence Q.C. notes:

(C) Predicted vs. Experimental sequence alignment.

```
Query = Predicted (SEQ ID NO: 78)
Subject = Experimental (SEQ ID NO: 79)
Score = 1917 bits (997), Expect = 0.0
Identities = 999/1000 (99%)
Strand = Plus/Plus Query:   1 gattgaatgatgagtgtgcacccttgtattactaataaaaaatttagcaacagttataag   60
           ||||||||||||||||||||||||||||||||||||||||||||||||||||||||||||
Sbjct:   1 gattgaatgatgagtgtgcacccttgtattactaataaaaaatttagcaacagttataag   60

Query:  61 ctaacgtcatccatgagtcattcattagattcactatttgcgttctcaaaaatcgaattg  120
           ||||||||||||||||||||||||||||||||||||||||||||||||||||||||||||
Sbjct:  61 ctaacgtcatccatgagtcattcattagattcactatttgcgttctcaaaaatcgaattg  120

Query: 121 ttaaaatttgagaagctctaatatacgagtcaatgagatgtggcaaaagcatgtccttga  180
           ||||||||||||||||||||||||||||||||||||||||||||||||||||||||||||
Sbjct: 121 ttaaaatttgagaagctctaatatacgagtcaatgagatgtggcaaaagcatgtccttga  180

Query: 181 ccataaaatttcgagggtcaactcattagataaggacaagaatcaaccaattgaaggcg  240
           ||||||||||||||||||||||||||||||||||||||||||||||||||||||||||||
Sbjct: 181 ccataaaatttcgagggtcaactcattagataaggacaagaatcaaccaattgaaggcg  240

Query: 241 tcttctataacaagtttctttattactaatattaaagtccaatggggtgaggggagaag  300
           ||||||||||||||||||||||||||||||||||||||||||||||||||||||||||||
Sbjct: 241 tcttctataacaagtttctttattactaatattaaagtccaatggggtgaggggagaag  300

Query: 301 aacttaaataaaaggaaataattggtaagtgaataaaaatctaaatacgatactagatgat  360
           ||||||||||||||||||||||||||||||||||||||||||||||||||||||||||||
Sbjct: 301 aacttaaataaaaggaaataattggtaagtgaataaaaatctaaatacgatactagatgat  360

Query: 361 tgatttgtgctagtgcatggtattagatcagatatgtgttactattcgaattcaaattgg  420
           ||||||||||||||||||||||||||||||||||||||||||||||||||||||||||||
Sbjct: 361 tgatttgtgctagtgcatggtattagatcagatatgtgttactattcgaattcaaattgg  420

Query: 421 catatttcatgttgttgataagaaaattgtagaagtgtaaaagctgagttactatattca  480
           ||||| ||||||||||||||||||||||||||||||||||||||||||||||||||||||
Sbjct: 421 catattccatgttgttgataagaaaattgtagaagtgtaaaagctgagttactatattca  480

Query: 481 aactagtggtttacataaagtgagacaacaactgtttcacaaaaatgactataaaatagt  540
           ||||||||||||||||||||||||||||||||||||||||||||||||||||||||||||
Sbjct: 481 aactagtggtttacataaagtgagacaacaactgtttcacaaaaatgactataaaatagt  540

Query: 541 aagtagtattaggtcaattgatttttaaaattttaatcaaattcaaatttgtgatataatc  600
           ||||||||||||||||||||||||||||||||||||||||||||||||||||||||||||
Sbjct: 541 aagtagtattaggtcaattgatttttaaaattttaatcaaattcaaatttgtgatataatc  600
```

-continued

```
Query:  601  aaatttgtttatagaaaatgttaagaaatcaattttggcagaactaattcagtgagaaac  660
             ||||||||||||||||||||||||||||||||||||||||||||||||||||||||||||
Sbjct:  601  aaatttgtttatagaaaatgttaagaaatcaattttggcagaactaattcagtgagaaac  660

Query:  661  aatcatttacaaaaacaattttaacattatttaacagtaagatttgacatttaacccgtt  720
             ||||||||||||||||||||||||||||||||||||||||||||||||||||||||||||
Sbjct:  661  aatcatttacaaaaacaattttaacattatttaacagtaagatttgacatttaacccgtt  720

Query:  721  cgtgtgaacccatcatatctaacatggctctacccatgacgcctccatgccatggacaat  780
             ||||||||||||||||||||||||||||||||||||||||||||||||||||||||||||
Sbjct:  721  cgtgtgaacccatcatatctaacatggctctacccatgacgcctccatgccatggacaat  780

Query:  781  tttgacagatcagaagttctgaacgtggacgaggtaagaacaccatgatgatacgattgg  840
             ||||||||||||||||||||||||||||||||||||||||||||||||||||||||||||
Sbjct:  781  tttgacagatcagaagttctgaacgtggacgaggtaagaacaccatgatgatacgattgg  840

Query:  841  agttagttatgtcgccaccgacatcactgccaatctcattaataaaagtggtactaaatc  900
             ||||||||||||||||||||||||||||||||||||||||||||||||||||||||||||
Sbjct:  841  agttagttatgtcgccaccgacatcactgccaatctcattaataaaagtggtactaaatc  900

Query:  901  tctaatctctattaactataaatataacaaagaaccaaaagaaagtttcttatctctctt  960
             ||||||||||||||||||||||||||||||||||||||||||||||||||||||||||||
Sbjct:  901  tctaatctctattaactataaatataacaaagaaccaaaagaaagtttcttatctctctt  960

Query:  961  atctttcataatttccaagaaacacaaaccttttctacta           1000
             ||||||||||||||||||||||||||||||||||||||||
Sbjct:  961  atctttcataatttccaagaaacacaaaccttttctacta           1000
```

Promoter Expression Report #233
Promoter Tested In: *Arabidopsis thaliana*, WS ecotype
Spatial expression summary:
Cotyledon             L epidermis
Observed expression pattern:
T1 mature: No expression observed.
T2 seedling: Weak epidermal expression in cotyledons.
Expected expression pattern:     Shade Induced
Selection Criteria:            Microarray data
Gene:                             expressed protein
GenBank: NM_124668 *Arabidopsis thaliana* expressed protein (At5g52900) mRNA, complete cds gi|30696256|ref|NM_124668.2|[30696256]
Source Promoter Organism:     *Arabidopsis thaliana* WS
Vector:                         pNewbin4-HAP1-GFP
Marker Type:                 GFP-ER
Generation Screened:    XT1 Mature XT2 Seedling ↑T2 Mature ↑T3 Seedling
Inductions completed.

| Treatment: | Age: | Gen: | Time points: | Events Screened/Response | Response: |
|---|---|---|---|---|---|
| 1. Far red | 7 days | T2 | 1 Hr | 6/0 | No |
| Far Red$_{730}$ = 525 μW/cm$^2$ | | | 4 Hr | 6/0 | No |
| | | | 24 Hr | 6/0 | No |

Inducible expression summary:
Treatment:          Time point induced:      Organs induced:      Tissues induced:
T1 Mature Plant Expression      Organs/Tissues screened
Events Screened:     n = 3      Events Expressing:     n = 0
X No GFP Expression Detected
T2 Seedling Expression      Tissues Screened
Events Screened: n = 3      Events Expressing: n = 2
Seedlings expressing/Seedlings screened
Event-01: 1/6
Event-03: 0/6
Event-06: 2/6
GFP Expression Detected

| | |
|---|---|
| ↑ Hypocotyl | ↑epidermis ↑cortex ↑vascular ↑xylem ↑phloem ↑stomata |
| X Cotyledon | ↑mesophyll ↑vascular L epidermis ↑margin ↑stomata ↑hydathode |
| ↑ Rosette Leaf | ↑mesophyll ↑vascular ↑epidermis ↑trichome ↑petiole ↑primordia ↑stomata ↑stipule ↑margin ↑hydathode |
| ↑ Primary Root | ↑epidermis ↑trichoblast ↑atrichoblast ↑cortex ↑endodermis ↑vascular ↑xylem ↑phloem ↑pericycle ↑quiescent ↑columella ↑root cap ↑root hairs |
| ↑ Lateral root | ↑epidermis ↑trichoblast ↑atrichoblast ↑cortex ↑endodermis ↑initials ↑flanking cells ↑vascular ↑lateral root cap |
| ↑ Shoot apical meristem | ↑Shoot apical meristem |
| Construct: | PT0687 |

-continued

| Promoter candidate I.D: | 15296009 |
|---|---|
| cDNA I.D: | 23457674 |
| Lines expressing: | PT0687-01, -06 |

(A) Predicted promoter sequence (1000 bp).

5' CCAGTCGA▼TTGGCCCGAT▼CGGCC (nucletides 1–23 of SEQ ID NO: 2)

(SEQ ID NO: 56)
caacaaacattcccttggagatttgagagattcatatcattaaatgcact tctcaatatacggagtattactaattaaaaccttatttcgagttctctca aacgtaacccatgcaaaaatggccccagagataagactttgatgagtctc cacgtcactttctgatttcggcttttgtccctaatctttcgacaacatt cgtctcgcaccccgacatttcccgggacctctgtctctcccctctcttt ctcctctcctctcccatttctcaacttttttccttattcacgaaatagac ttttttattttagttttcttttctcccatttgtaactcgtggtccttct tcatttgtattaatgctctggaaattttcttcttaaaacgttatacagct atttttgcttttcctatacatattcgtttcatagttgtgttttctttgt ctatcaaaacaattagttccatgagatatgtgtcaatacttaacatgcat cgtcttttctgatttgtgataactctcaaacaaattaaaataatcat gctctaggagaggagataacgtcattcatatcatgatcttcctaattaaa atataattatgttgccaccgggaatataattaaaataacccctatattcga aaagaaaagagaaaacaaaaactaaaaaaaaaaaggaaaggagtgaaggc aacagcacataatgagaggttagtatgggctcacaaactcttatgtttct tttcttttcttttttccctttccaattattaatatctattgtttcttacc aaactaaccacatatatatttatatattaccgttattaaattaaaataaa attatgtgtatatgtccctctctatatataaacactgaaacatatgttcc caattcaaaaaattgttttgtctcaaacaaatttctctgcacacactcaa caacatatcccataacaaaaaaagctattaaaaaaaagagaagcagcc (nucletides 38–60 of SEQ ID NO: 2)

GGCCTGCA▼GGGCCAGTGCA▼

CTGG 3'

(B) Sequence verification and confirmation.

| Sequence (bp) | Mismatch | Predicted/Experimental |
|---|---|---|
| Sequence Q.C. notes: | | |

(C) Predicted vs. Experimental sequence alignment.

```
Query = Predicted (SEQ ID NO: 56)
Subject = Experimental (SEQ ID NO: 56)
Score = 1923 bits (1000), Expect = 0.0
Identities = 1000/1000 (100%)
Strand = Plus/Plus Query:    1 caacaaacattcccttggagatttgagagattcatatcattaaatgcacttctcaatata   60
            ||||||||||||||||||||||||||||||||||||||||||||||||||||||||||||
Sbjct:   45 caacaaacattcccttggagatttgagagattcatatcattaaatgcacttctcaatata  104

Query:   61 cggagtattactaattaaaaccttatttcgagttctctcaaacgtaacccatgcaaaaat  120
            ||||||||||||||||||||||||||||||||||||||||||||||||||||||||||||
Sbjct:  105 cggagtattactaattaaaaccttatttcgagttctctcaaacgtaacccatgcaaaaat  164

Query:  121 ggccccagagataagactttgatgagtctccacgtcactttctgatttcggcttttgtcc  180
            ||||||||||||||||||||||||||||||||||||||||||||||||||||||||||||
Sbjct:  165 ggccccagagataagactttgatgagtctccacgtcactttctgatttcggcttttgtcc  224

Query:  181 cctaatctttcgacaacattcgtctcgcaccccgacatttcccgggacctctgtctctcc  240
            ||||||||||||||||||||||||||||||||||||||||||||||||||||||||||||
Sbjct:  225 cctaatctttcgacaacattcgtctcgcaccccgacatttcccgggacctctgtctctcc  284

Query:  241 ccctctctttctcctctcctctcccatttctcaacttttttccttattcacgaaatagac  300
            ||||||||||||||||||||||||||||||||||||||||||||||||||||||||||||
Sbjct:  285 ccctctctttctcctctcctctcccatttctcaacttttttccttcattcacgaaatagac  344

Query:  301 ttttttattttagttttcttttctcccatttgtaactcgtggtccttcttcatttgtat  360
            ||||||||||||||||||||||||||||||||||||||||||||||||||||||||||||
Sbjct:  345 ttttttattttagttttcttttctcccatttgtaactcgtggtccttcttcatttgtat  404
```

```
-continued
Query:    361 taatgctctggaaattttcttcttaaaacgttatacagctattttttgcttttttcctatac  420
              ||||||||||||||||||||||||||||||||||||||||||||||||||||||||||||
Sbjct:    405 taatgctctggaaattttcttcttaaaacgttatacagctattttttgcttttttcctatac  464

Query:    421 atattcgtttcatagttgtgttttctttgtctatcaaaacaattagttccatgagatatg  480
              ||||||||||||||||||||||||||||||||||||||||||||||||||||||||||||
Sbjct:    465 atattcgtttcatagttgtgttttctttgtctatcaaaacaattagttccatgagatatg  524

Query:    481 tgtcaatacttaacatgcatcgtctttttctgatttgtggataactctaaacaaatta  540
              ||||||||||||||||||||||||||||||||||||||||||||||||||||||||||||
Sbjct:    525 tgtcaatacttaacatgcatcgtctttttctgatttgtggataactctaaacaaatta  584

Query:    541 aaataatcatgctctaggagaggagataacgtcattcatatcatgatcttcctaattaaa  600
              ||||||||||||||||||||||||||||||||||||||||||||||||||||||||||||
Sbjct:    585 aaataatcatgctctaggagaggagataacgtcattcatatcatgatcttcctaattaaa  644

Query:    601 atataattatgttgccaccgggaatataattaaaataaccctatattcgaaaagaaaaga  660
              ||||||||||||||||||||||||||||||||||||||||||||||||||||||||||||
Sbjct:    645 atataattatgttgccaccgggaatataattaaaataaccctatattcgaaaagaaaaga  704

Query:    661 gaaacaaaaactaaaaaaaaaaggaaaggagtgaaggcaacagcacataatgagaggt  720
              ||||||||||||||||||||||||||||||||||||||||||||||||||||||||||||
Sbjct:    705 gaaacaaaaactaaaaaaaaaaggaaaggagtgaaggcaacagcacataatgagaggt  764

Query:    721 tagtatgggctcacaaactcttatgtttctttcttttcttttttcccttttccaattatt  721
              ||||||||||||||||||||||||||||||||||||||||||||||||||||||||||||
Sbjct:    765 tagtatgggctcacaaactcttatgtttctttcttttcttttttcccttttccaattatt  824

Query:    781 aatatctattgtttcttaccaaactaaccacatatatatttatatattaccgttattaaa  840
              ||||||||||||||||||||||||||||||||||||||||||||||||||||||||||||
Sbjct:    825 aatatctattgtttcttaccaaactaaccacatatatatttatatattaccgttattaaa  884

Query:    841 ttaaaataaaattatgtgtatatgtccctctctatatataaacactgaaacatatgttcc  900
              ||||||||||||||||||||||||||||||||||||||||||||||||||||||||||||
Sbjct:    885 ttaaaataaaattatgtgtatatgtccctctctatatataaacactfaaacatatgttcc  944

Query:    901 caattcaaaaaattgttttgtctcaaacaaatttctctgcacacactcaacaacatatcc  960
              ||||||||||||||||||||||||||||||||||||||||||||||||||||||||||||
Sbjct:    945 caattcaaaaaattgttttgtctcaaacaaatttctctgcacacactcaacaacatatcc  1004

Query:    961 cataacaaaaaaagctattaaaaaaaaagagaagcagcc                       1000
              |||||||||||||||||||||||||||||||||||||||
Sbjct:   1005 cataacaaaaaaagctattaaaaaaaaagagaagcagcc                       1044
```

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. An isolated nucleic acid molecule consisting of the nucleotide sequence set forth in SEQ ID NO: 56 which acts as a plant promoter.

2. A polynucleotide comprising the plant promoter according to claim 1 operatively linked to a heterologous sequence.

3. The polynucleotide according to claim 2 wherein the heterologous sequence encodes a detectable product.

4. A vector comprising the polynucleotide according to claim 2.

5. A host cell stably transformed with the polynucleotide according to claim 2.

6. A host cell stably transformed with the vector according to claim 4.

7. A transformed plant cell comprising a plant promoter consisting of the nucleotide sequence according to claim 1, operatively linked to a heterologous sequence.

8. The plant cell of claim 7, wherein the plant cell is a monocot plant cell.

9. The plant cell of claim 7, wherein the plant cell is a dicot plant cell.

10. A transgenic plant comprising a genome that includes a plant promoter consisting of the nucleotide sequence set forth in SEQ ID NO: 56, operatively linked to a heterologous sequence.

11. The transgenic plant of claim 10, wherein the plant is selected from the group consisting of canola, crambe, mustard, castor bean, sesame, cottonseed, linseed, maize, soybean, *Arabidopsis, Phaseolus*, peanut, alfalfa, wheat, rice, oat, sorghum, rapeseed, rye, tritordeum, millet, fescue, perennial, ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee, dioscorea and a monocot plant.

12. A seed from the plant of claim 10, wherein said seed contains said plant promoter operatively linked to said heterologous sequence.

13. A method of producing a transformed plant cell, the method comprising introducing into a plant cell a plant promoter consisting of the nucleotide sequence set forth in SEQ ID NO: 56, whereby said plant promoter is operatively linked to a heterologous sequence in said transformed plant cell.

14. A method of producing a transgenic plant, the method comprising: introducing into a plant cell the plant promoter according to claim 1, whereby said plant promoter is operatively linked to a heterologous sequence in said transformed plant cell and cultivating the cell to generate a plant.

15. A DNA construct comprising the promoter DNA sequence set forth in SEQ ID NO: 56; a structural DNA sequence; and a 3' non-translated region that functions in plants to cause the addition of polyadenylated nucleotides to the 3' end of the RNA sequence; wherein the structural DNA sequence is operably linked to the promoter and the 3' non-translated region, and the promoter DNA sequence is heterologous with respect to the structural DNA sequence.

16. A transgenic crop plant comprising the DNA construct of claim 15.

17. A method of expressing a structural DNA sequence in a plant, the method comprising: (1) providing a DNA construct comprising a promoter that is SEQ ID NO: 56; a structural DNA sequence; and a 3' non-translated region that functions to cause the addition of polyadenylated nucleotides to the 3' end of the RNA sequence; wherein the structural DNA sequence is operably linked to the promoter and the 3' non-translated region, and the promoter is heterologous with respect to the structural DNA sequence; (2) introducing the DNA construct into a plant cell; and (3) regenerating the plant cell to produce a plant such that the structural DNA sequence is expressed in the plant.

18. A transformed plant comprising the plant promoter according to claim 1 operatively linked to a heterologous sequence, wherein said transformed plant having increased expression of said heterologous sequence when the transformed plant is grown under shade conditions compared to a wild-type plant of the same species cultivated under the same conditions.

19. A seed of the plant according to claim 18, wherein said seed contains the plant promoter of SEQ ID NO: 56 operatively linked to said heterologous sequence.

20. A method of producing a transformed plant having increased expression of a heterologous sequence when the transformed plant is grown under shade conditions compared to a wild-type plant of the same species cultivated under the same conditions, which comprises introducing the plant promoter according to claim 1 operatively linked to the heterologous sequence into a plant cell to increase expression of the heterologous sequence in said plant cell and regenerating a plant from said plant cell.

* * * * *